United States Patent
Burge et al.

(10) Patent No.: US 11,572,560 B2
(45) Date of Patent: Feb. 7, 2023

(54) SPLICING-DEPENDENT TRANSCRIPTIONAL GENE SILENCING OR ACTIVATION

(71) Applicant: Massachusetts Institute of Technology, Cambridge, MA (US)

(72) Inventors: Christopher B. Burge, Belmont, MA (US); Ana Fiszbein, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 229 days.

(21) Appl. No.: 16/530,149

(22) Filed: Aug. 2, 2019

(65) Prior Publication Data

US 2020/0109400 A1    Apr. 9, 2020

Related U.S. Application Data

(60) Provisional application No. 62/740,881, filed on Oct. 3, 2018.

(51) Int. Cl.
  *C07H 21/04*  (2006.01)
  *C12N 15/113* (2010.01)

(52) U.S. Cl.
  CPC ........ *C12N 15/113* (2013.01); *C12N 2310/11* (2013.01)

(58) Field of Classification Search
  None
  See application file for complete search history.

(56) References Cited

U.S. PATENT DOCUMENTS

2006/0275294 A1   12/2006   Omoigui

FOREIGN PATENT DOCUMENTS

WO   WO 2015/091525 A1   6/2015
WO   WO 2016/149659 A2   9/2016

OTHER PUBLICATIONS

PCT/US2019/044936, Oct. 31, 2019, International Search Report and Written Opinion.

International Search Report and Written Opinion dated Oct. 31, 2019 for Application No. PCT/US2019/044936.
Agarwal et al., Enhancement of Transcription by a Splicing-Competent Intron Is Dependent on Promoter Directionality. PLoS Genet. May 6, 2016;12(5):e1006047, 20 pages, doi: 10.1371/journal.pgen.1006047. eCollection May 2016.
Brown et al., Isolation and characterization of the 5' flanking region of the mouse c-Harvey-ras gene. Mol Carcinog. 1988;1(3):161-70.
Damgaard et al., A 5' splice site enhances the recruitment of basal transcription initiation factors in vivo. Mol Cell. Feb. 1, 2008;29(2):271-8. doi: 10.1016/j.molcel.2007.11.035.
Das et al., SR proteins function in coupling RNAP II transcription to pre-mRNA splicing. Mol Cell. Jun. 22, 2007;26(6):867-81.
Derti et al., A quantitative atlas of polyadenylation in five mammals. Genome Res. Jun. 2012;22(6):1173-83. doi: 10.1101/gr.132563.111. Epub Mar. 27, 2012.
Du et al., Progress toward therapy with antisense-mediated splicing modulation. Curr Opin Mol Therap. Apr. 2009;11(2):116-23.
Fiszbein et al., Exon-mediated activation of transcription starts. bioRxiv. Mar. 1, 2019:1-45. doi: 10.1101/565184.
Gallegos et al., Intron DNA Sequences Can Be More Important Than the Proximal Promoter in Determining the Site of Transcript Initiation. Plant Cell. Apr. 2017;29(4):843-853. doi: 10.1105/tpc.17.00020. Epub Apr. 3, 2017.
Gonzalez-Cadavid et al., Organization of the human myostatin gene and expression in healthy men and HIV-infected men with muscle wasting. PNAS USA. Dec. 1998;95:14938-43.
Gracheva et al., Ganglion-specific splicing of TRPV1 underlies infrared sensation in vampire bats. Nature. Aug. 3, 2011;476(7358):88-91. doi: 10.1038/nature10245.
Gunderson et al., U1 snRNP Inhibits Pre-mRNA Polyadenylation through a Direct Interaction between U1 70K and Poly(A) Polymerase. Mol Cell. Jan. 1998;1(2):255-64.
Hua et al., Antisense-mediated exon inclusion. Methods Mol Biol. 2012;867:307-23.
Liang et al., Analysis of changes in transcription start site distribution by a classification approach. Gene. 2014;537:29-40.
Sorek et al., Minimal conditions for exonisation of intronic sequences: 5' splice site formation in alu exons. Mol Cell. Apr. 23, 2004;14:221-31.

*Primary Examiner* — Kimberly Chong
(74) *Attorney, Agent, or Firm* — Wolf, Greenfield & Sacks, P.C.

(57) ABSTRACT

Disclosed herein are methods for inhibiting or activating the transcription of a gene of interest, or inhibiting or activating the transcription of specific mRNA isoforms of a gene by using antisense oligonucleotides and/or small molecules. Also described herein are methods for activating transcription from a promoter and increasing overall gene expression by creating of a new splice site in a gene of a cell.

14 Claims, 55 Drawing Sheets
Specification includes a Sequence Listing.

FIG. 18A

| | | |
|---|---|---|
| (SEQ ID NO: 3) | mm | atgtggatgaagtgagaagaactctatgccgtgggagcggagcgca-ccgtggtggt... |
| (SEQ ID NO: 4) | m | ttgtggatgaagtgagaagaactctatccctcggagcggagcgcacaagtggtggtgac |
| (SEQ ID NO: 5) | m + mm 3'ss | ttgtggatgaagtgagaagaactctatccctcggagcggagcgcacaagtggtggtgac |
| (SEQ ID NO: 6) | 5' RACE clon A | ---------------------------------------------------------tgac |
| (SEQ ID NO: 7) | 5' RACE clon B | -------------------------------------cggagcgcacaagtggtggtgac |
| | | * ** |

| | | |
|---|---|---|
| | mm | cagcgtggcgagcttagctgaaagcggctcccgccacacttggccgggccagagcctg |
| | m | cagcgtggcgagcttagctgaaagcggctcccgccacacttggccgggccagagcctg |
| | m + mm 3'ss | cagcgtggcgagcttagctgaaagcggctcccgccacacttggccgggccagagcctg |
| | 5' RACE clon A | cagcgtggcgagcttagctgaaagcggctcccgccacacttggccgggccagagcctg |
| | 5' RACE clon B | cagcgtggcgagcttagctgaaagcggctcccgccacacttggccgggccagagcctg |
| | | ************************************* *** ***** * |

| | | |
|---|---|---|
| | mm | ggtattgggaatacttcctgaagacagctggtccacccctggaagtccctgccaaagca |
| | m | ggtattgggaatacttcctgaagacagctggtccacccctggaagtccctgccaaagca |
| | m + mm 3'ss | ggtattgggaatacttcctgaagacagctggtccacccctggaagtccctgccaaagca |
| | 5' RACE clon A | ggtattgggaatacttcctgaagacagctggtccacccctggaagtccctgccaaagca |
| | 5' RACE clon B | ggtattgggaatacttcctgaagacagctggtccacccctggaagtccctgccaaagca |
| | | * * *********** **** ***** ****** ************ |

FIG. 18D

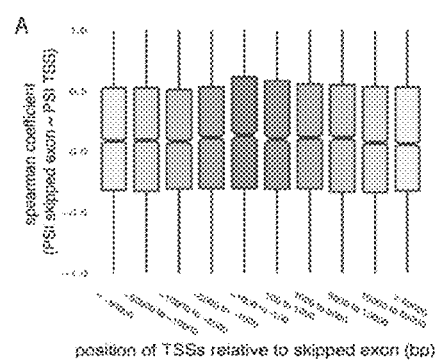

FIG. 19A

SEQUENCE LISTING

<160> NUMBER OF SEQ ID NOS: 7

<210> SEQ ID NO 1
<211> LENGTH: 473
<212> TYPE: DNA
<213> ORGANISM: Mus musculus

<400> SEQUENCE: 1
ggacgagcgg cgcggagaaa agcgccggcc catgggccaa cgccgggtcg cctaggtgag    60
cgtgccgagg cgacaactgc agacctgcca ggtgggtgct gtcgggaggc gcagcgagat   120

```
cggcgcgcat tggaggtttt ggagcccggg actccaacct caccgcccca tcccgtgagt    180
ggtaaccagc gtggcgagct tagctgaaag cggctcccgc ccacacttgg ccaggctcag    240
aggtgactca aactttgatc ctttcttgct ccatgctagc ctttcggata agtctagacc    300
agagacaatg tacttgattg ggttccctat cctttctcag gacgctgagc ctgggagttt    360
cctgaagaca tctggcccca cttcggaagt gtcctgccaa agcaagtgct aagacaggca    420
ggtcccatag gagcagacct ggctgagcag gtgactctct ctactcaggg gtt           473
```

```
<210> SEQ ID NO 2
<211> LENGTH: 476
<212> TYPE: DNA
<213> ORGANISM: Rattus norvegicus

<400> SEQUENCE: 2
ggacgtgcgg gctccgagaa aagcgctggc ccacgggcca acgccgggtc gcctaggtga     60
gcgtgccgag gcgacagctg ccgacctgcc aggtgggtgc tgtcccgaag cgcagcgaga    120
tcggcgccgg tttggaggtt tggagcccgg gacttcaacc tcaccgcccc atcctgtgag    180
tggtgaccag cgtggcgagc ttagctgaaa gcggctcccg cccacacttg gccgggccca    240
gaggtgactc aatctttgat cctttcttgc tccatgctag cttttcggat aagtctagac    300
cagagacaat gtacttgatt gggttcatcc cttctccggg ctccgagcct gggtattggg    360
aatacttcct gaagacagct ggtcccactt cggaagtccc ctgccaaagc aagtgctaag    420
agaggcaggt tccataggag cagacctggc agagcaggtg actgtactca ggggtt        476
```

```
<210> SEQ ID NO 3
<211> LENGTH: 179
<212> TYPE: DNA
<213> ORGANISM: Mus musculus

<400> SEQUENCE: 3
atgtggatga agtgagaaga actctatgcc gtgggagcgg agcgcaccgt ggtggtaacc     60
agcgtggcga gcttagctga aagcggctcc cgcccacact tggccaggct cagaggacgc    120
tgagcctggg agtttcctga agacatctgg ccccacttcg gaagtgtcct gccaaagca     179
```

```
<210> SEQ ID NO 4
<211> LENGTH: 180
<212> TYPE: DNA
<213> ORGANISM: Rattus norvegicus

<400> SEQUENCE: 4
ttgtggatga agtgagaaga acacaatccc tcgggagcgg agcgcacaag tggtggtgac     60
cagcgtggcg agcttagctg aaagcggctc ccgcccacac ttggccgggc ccagagcctg    120
ggtattggga atacttcctg aagacagctg gtcccaccct ggaagtcccc tgccaaagca    180
```

```
<210> SEQ ID NO 5
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 5
ttgtggatga agtgagaaga acacaatccc tcgggagcgg agcgcacaag tggtggtgac     60
cagcgtggcg agcttagctg aaagcggctc ccgcccacac ttggccgggc ccagaggctg    120
ggtattggga atacttcctg aagacagctg gtcccaccct ggaagtcccc tgccaaagca    180
```

```
<210> SEQ ID NO 6
<211> LENGTH: 124
<212> TYPE: DNA
<213> ORGANISM: Artificial Sequence
<220> FEATURE:
<223> OTHER INFORMATION: Synthetic Polynucleotide

<400> SEQUENCE: 6
tgaccagcgt ggcgagctta gctgaaagcg gctcccgccc acacttggcc gggcccagag      60
gctgggtatt gggaatactt cctgaagaca gctggtccca ccctggaagt ccnctgccaa    120
agca                                                                 124

<210> SEQ ID NO 7
<211> LENGTH: 143
<212> TYPE: DNA
<213> ORGANISM: Artificial Sequence
<220> FEATURE:
<223> OTHER INFORMATION: Synthetic Polynucleotide

<400> SEQUENCE: 7
cggagcgcac aagtggtggt gaccagcgtg gcgagcttag ctgaaagcgg ctcccgccca      60
cacttggccg ggcccagagg ctgggtattg ggaatacttc ctgaagacag ctggtcccac    120
cctggaagtc ccctgccaaa gca                                            143
```

SPLICING-DEPENDENT TRANSCRIPTIONAL GENE SILENCING OR ACTIVATION

RELATED APPLICATIONS

This application claims the benefit under 35 U.S.C. § 119(e) of U.S. Provisional Application Ser. No. 62/740,881, filed on Oct. 3, 2018, and entitled "SPLICING-DEPENDENT TRANSCRIPTIONAL GENE SILENCING OR ACTIVATION," which is herein incorporated by reference in its entirety.

GOVERNMENT SUPPORT

This invention was made with government support under Grant No. R01 GM085319 awarded by the National Institutes of Health. The government has certain rights in the invention.

BACKGROUND OF THE INVENTION

The process of transcription yields precursor mRNA (pre-mRNA) transcripts, which, in eukaryotes, typically comprise alternating exons (i.e. coding nucleotide sequences), and introns (i.e. non-coding nucleotide sequences) of the gene. During pre-mRNA processing, introns are excised and the remaining exons are reconnected. This is pre-mRNA splicing to produce mature RNA. The process of pre-mRNA splicing is facilitated by a complex of small nuclear ribonucleoparticles (snRNPs) that form a spliceosome. The mature RNA is then exported out of the nucleus and undergoes translation in the cytoplasm.

SUMMARY OF THE INVENTION

The present disclosure is based, at least in part, on methods for silencing or activating a gene of interest using antisense oligonucleotides (e.g. splice-switching oligonucleotides) or small molecules targeted for an internal exon or a region of the gene around the internal exon. The present disclosure also provides methods for the insertion of a splice site with an exogenous exon, to activate a proximal transcription start site and increase gene expression.

Accordingly, one aspect of the present disclosure provides a method for inhibiting transcription from a transcription start site in a gene of a cell by contacting the cell with an antisense oligonucleotide or small molecule targeted for an internal exon within the gene to inhibit transcription from the transcription start site. In some embodiments, the transcription start site is upstream of the internal exon. In some embodiments, the inhibition of transcription includes a reduction in isoform expression. In some embodiments, the gene has multiple transcription start sites. In some embodiments, the transcription start site has weak intrinsic activity. In some embodiments, the antisense oligonucleotide (ASO) is a morpholino oligonucleotide, a phosphorothioate ASO, a 2'-O-methyl (2'-OMe) ASO, 2'-O-methoxyethyl (2'MOE) ASO, a locked nucleic acid (LNA) ASO, a peptide-conjugated phosphorodiamidate morpholino (PMO) ASO or a Vivo-linked phosphorodiamidate morpholino (VPMO). In some embodiments, the antisense oligonucleotide or small molecule is targeted for the 3' splice site or 5' splice site of the internal exon. In further embodiments, a second antisense oligonucleotide or second small molecule is included. In such cases, the antisense oligonucleotide or small molecule and the second antisense oligonucleotide or second small molecule are targeted for the 3' splice site and the 5' splice site of the internal exon, respectively. In some embodiments, the second antisense oligonucleotide is a morpholino oligonucleotide, a phosphorothioate ASO, a 2'-O-methyl (2'-OMe) ASO, 2'-O-methoxyethyl (2'MOE) ASO, a locked nucleic acid (LNA) ASO, a peptide-conjugated phosphorodiamidate morpholino (PMO) ASO or a Vivo-linked phosphorodiamidate morpholino (VPMO). In some embodiments, the antisense oligonucleotide or small molecule is targeted for a site in the internal exon or around the internal exon. In some embodiments, the antisense oligonucleotide or small molecule inhibits splicing of the internal exon. In some embodiments, the internal exon is within 1 kb from the transcription start site or within 5 kb from the transcription start site. In some embodiments, the internal exon has high intrinsic splicing activity. In some embodiments, the gene is NOTCH2 gene, MEN1 gene, dystrophin gene or p53 gene. In some embodiments, the gene is associated with myotonic dystrophy type I. In some embodiments, the gene is HTT or another gene associated with Huntington's disease. In some embodiments, the gene is an oncogene, for example, c-myc, Ras, STAT3, or bcl-2. In some embodiments, the cell is in a subject and the antisense oligonucleotide or small molecule is administered to the subject. In some embodiments, the methods of the present disclosure include measuring the level of transcription relative to a baseline level. In some embodiments, the targeting for an internal exon is based on the proximity of the internal exon to the transcription start site.

Another aspect of the present disclosure provides a method for activating transcription from a transcription start site in a gene of a cell by contacting the cell with an antisense oligonucleotide or small molecule targeted for a silencing element in the gene. The silencing element can be known or unknown. In some embodiments, the silencing element is an intronic silencing element. In some embodiments, the silencing element is downstream or upstream of a skipped exon. In some embodiments, the silencing element is an exonic silencing element on a skipped exon. In some embodiments, the transcription start site is upstream of the skipped exon. In some embodiments, the antisense oligonucleotide (ASO) is a morpholino oligonucleotide, a phosphorothioate ASO, a 2'-O-methyl (2'-OMe) ASO, 2'-O-methoxyethyl (2'MOE) ASO, a locked nucleic acid (LNA) ASO, a peptide-conjugated phosphorodiamidate morpholino (PMO) ASO or a Vivo-linked phosphorodiamidate morpholino (VPMO). In some embodiments, the skipped exon is within 1 kb from the upstream transcription start site or within 5 kb from the upstream transcription start site. In some embodiments, the upstream transcription start site has weak intrinsic activity. In some embodiments, the skipped exon has high intrinsic splicing activity. In some embodiments, the antisense oligonucleotide or small molecule activates inclusion of the skipped exon. In some embodiments, the gene encodes a therapeutic protein. In some embodiments, the gene is MLH3 gene, dystrophin gene or utropin gene. In some embodiments, the gene is an antioncogene. In some embodiments, the therapeutic protein is p53, pRb, PTEN, pVHL, APC, BRCA1, BRCA2, CD95, ST5, YPEL3, ST7, or ST14. In some embodiments, the cell is in a subject and the antisense oligonucleotide or small molecule is administered to the subject. In further embodiments, the methods of the present disclosure include measuring level of transcription relative to a baseline level. In some embodiments, the targeting for a silencing element is based on the proximity of the skipped exon to the transcription start site. In some embodiments, the antisense oligonucleotide is a splice-switching oligonucleotide.

Another aspect of the present disclosure provides a method for activating transcription from a transcription start site in a gene of a cell by modifying the gene to add a splice site and an exogenous internal exon, and the addition of the splice site and exogenous internal exon are sufficient to promote activation of a proximal transcription start site. In some embodiments, the splice site and exogenous internal exon are added through the use of a vector. The method can also include contacting the cell with an antisense oligonucleotide or a small molecule targeted for a silencing element in the gene. In some embodiments, the antisense oligonucleotide or small molecule activates inclusion of a skipped exon in the gene. In some embodiments, the antisense oligonucleotide (ASO) is a morpholino oligonucleotide, a phosphorothioate ASO, a 2'-O-methyl (2'-OMe) ASO, 2'-O-methoxyethyl (2'MOE) ASO, a locked nucleic acid (LNA) ASO, a peptide-conjugated phosphorodiamidate morpholino (PMO) ASO or a Vivo-linked phosphorodiamidate morpholino (VPMO). In some embodiments, the antisense oligonucleotide is a splice-switching antisense oligonucleotide. In some embodiments, the splice site is a 3' splice site sequence, and has a corresponding 5' splice sequence that is a wild type 5' splice site. In some embodiments, the transcription start site is upstream of the exogenous internal exon. In some embodiments, the transcription start site has weak intrinsic activity. In some embodiments, the exogenous internal exon is within 1 kb from the transcription start site, or within 5 kb from the transcription start site. In some embodiments, the exogenous internal exon has high intrinsic splicing activity. In some embodiments, the gene encodes a therapeutic protein. In some embodiments, the gene is SMN2 gene, dystrophin gene or utropin gene. In some embodiments, the gene is an antioncogene. In some embodiments, the therapeutic protein is p53, pRb, PTEN, pVHL, APC, BRCA1, BRCA2, CD95, ST5, YPEL3, ST7, or ST14. In some embodiments, the cell is in a subject and the splice site and exogenous internal exon is administered to the subject. In some embodiments, the cell is in a subject and the vector is administered to the subject. In some embodiments, the addition of the splice site and exogenous internal exon is based on proximity to the transcription start site.

Another aspect of the present disclosure provides an antisense oligonucleotide that is targeted to and complementary to at least a portion of a silencing element in a gene, wherein the silencing element is an intronic silencing element downstream of a skipped exon and wherein the skipped exon is within 5 kb from an upstream transcription start site. In some embodiments, the antisense oligonucleotide is a morpholino oligonucleotide, a phosphorothioate ASO, a 2'-O-methyl (2'-OMe) ASO, 2'-O-methoxyethyl (2'MOE) ASO, a locked nucleic acid (LNA) ASO, a peptide-conjugated phosphorodiamidate morpholino (PMO) ASO or a Vivo-linked phosphorodiamidate morpholino (VPMO). In some embodiments, the upstream transcription start site has weak intrinsic activity. In some embodiments, the skipped exon has high intrinsic splicing activity. In some embodiments, the antisense oligonucleotide is a splice-switching oligonucleotide. In some embodiments, the skipped exon is within 1 kb from an upstream transcription start site.

Another aspect of the present disclosure provides a modified nucleic acid that has a gene that has a wild type 5' splice site, an exogenous 3' splice site and an exogenous internal exon. A transcription start site is upstream of the exogenous internal exon and the transcription start site has weak intrinsic activity and is within 5 kb from the transcription start site. In some embodiments, the exogenous internal exon has high intrinsic splicing activity. In some embodiments, the transcription start site is within 1 kb from the transcription start site.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings:

FIG. 3A: diagrams showing splicing patterns of the Tsku gene, with skipped exons 2 and 3 (E2.SE and E3.SE), in NIH 3T3 mouse fibroblast cells transfected for 24 hours with 20 uM morpholino SSO oligonucleotides targeting the 3' or 5' splice site or both splice sites of exon 2. Treatment with SSO block the inclusion of E2.SE in both transcripts starting at the distal (TSS-2) and the proximal (TSS-1) promoter. FIG. 3B: a schematic illustration showing the mapping of transcription initiation sites using 5' RACE. Schematic diagrams of 5' RACE products and number of clones obtained for each transcription start site (TSS) in control NIH 3T3 cells (WT) and cells transfected with 20 uM SSO targeting the 3' and the 5' splice sites of E2.SE in Tsku (SSO). Inhibiting the inclusion of the internal exon triggers inactivation of the most proximal upstream promoter. FIG. 3C: charts showing the correlation between fold change in gene expression of mouse and rat and percent spliced in (PSI) values of E2.SE for 9 tissues in Tsku, Spearman correlation coefficient is indicated. NIH 3T3 cells were transfected for 24 hours with 20 uM SSO targeting the 3' or the 5' splice site or both splice sites of the new exon in Tsku and total gene expression levels were assessed by qPCR. Mean±SEM of displayed distributions. Thus, inhibition of splicing significantly reduces overall gene expression.

FIG. 4A: a schematic illustration of hybrid constructs of the rat Tsku gene with the creation of a 3' splice site that promotes the inclusion of a skipped exon. FIG. 4B: diagrams showing splicing patterns of the Tsku gene in HeLa cells transfected with the hybrid constructs. The creation of the 3' splice site (rat+mm 3'ss) or a stronger 3' splice site (rat+strong 3'ss) in the rat sequence promotes the inclusion of a new exon only when maintaining the wild type 5' splice site. FIG. 4C: a schematic illustration of the mapping of transcription initiation sites of Tsku hybrid constructs using 5' RACE. Schematic illustrations of TSS usage and number of clones obtained from NIH 3T3 mouse cells transfected with plasmids expressing the corresponding Tsku mutants. The splicing activation triggers the usage of the most proximal upstream promoter. FIG. 4D: diagrams showing the Luciferase activity of promoter assay vectors in HeLa cells transfected with the hybrid constructs of the Tsku gen. Promoter activities of the corresponding constructs (corrected for transfection efficiency) are presented as fold increase of Renilla Luciferase activity relative to firefly Luciferase activity in the same plasmid. Mean±SD, n=3 independent experiments.

FIG. 8A: Phylogenetic tree representing the main species used for dating evolutionarily new exons and approximate branch lengths in millions of years. The patterns of inclusion/exclusion used to infer mouse-specific new exons (n=1089) and rat-specific new exons (n=1517) are shown. FIG. 8B: a chart showing fold change in gene expression between mouse and rat for mouse control genes with no evolutionarily new exons (black, dotted line), genes with mouse-specific new exons in tissues where inclusion of the new exon is not detected, PSI<0.05 (grey), and genes with new mouse-specific exons in tissues were the exon is included, PSI>0.05 (pink). Statistical significance by Mann-Whitney U test is indicated between genes with mouse-specific new exons in tissues with PSI<0.05 and tissues with PSI>0.05. FIG. 8C: a chart showing fold change in gene expression between mouse and rat in 9 organs (brain, heart, colon, kidney, liver, lung, skeletal muscle, spleen and testes) for genes with mouse-specific new exons, binned by W value of the new exon in each tissue. ** $p<0.0001$ by one-way ANOVA, Tukey post hoc test. FIGS. 8D-8E: charts showing the correlation between fold change in gene expression of mouse and rat and PSI values of the new exon for 9 tissues in Gpr30 (FIG. 8D) and Tsku (FIG. 8E), rho spearman coefficient is indicated (left). NIH3T3 cells were transfected for 24 hours with 20 uM morpholino (MO) targeting the 5' splice site of the new exon in Gpr30 (FIG. 8D) and 20 uM MO targeting the 3' or the 5' or both splice sites of the new exon in Tsku (FIG. 8E). FIG. 8D: (Left) Relationship between fold change in gene expression between mouse and rat and new exon PSI value across 9 tissues for Gper1 gene (FIG. 8D) and (FIG. 8E). (Right) qRT-PCR analysis of fold change in new exon PSI value (middle) and gene expression (right) in nascent RNA metabolically labeled for 10 minutes with 5-ethynyl uridine, following treatment of NIH3T3 cells with MO targeting new exon 5' splice site relative to control treatment. Mean±SEM of displayed distributions, n=3 biological replicates.  $p<0.01$, * $p<0.001$,  $p<0.0001$ by one-way ANOVA, Tukey post hoc test. FIG. 8F: a chart showing the fold change in gene expression between mouse and rat for mouse control genes with no new exons (white), genes with mouse-specific new exons in tissues where inclusion of the new exon is not detected, PSI<0.05 (grey), and genes with new mouse-specific exons in tissues were the exon is included, PSI>0.05 (pink); binned by the number of TSSs per gene in mouse. Increased gene expression values associated with inclusion of new exons are only observed in genes with alternative TSSs (no. of TSS>1). * $p<0.001$ by one-way ANOVA, Tukey post hoc test. FIG. 8G: a chart showing the distribution of the number of TSSs per gene using Start-seq data for all genes expressed in mouse and genes with mouse-specific new exons. TSSs located less than 50 nucleotides apart from each other are clustered as a single TSS. Distributions are significantly different with a p value of $2.2e^{-16}$ by Kolmogorov-Smirnov test. Genes with mouse-specific new exons have increased numbers of TSSs ($p<2.2e-16$ by Kolmogorov-Smirnov test). Genes with mouse-specific new exons are enriched in multiple TSSs. FIG. 8H: a histogram of genes that gained TSSs in mouse (genes with mouse TSS>rat TSS), genes that lost TSSs in mouse (genes with mouse TSS<rat TSS) and genes with same number of TSSs in both species (genes with mouse TSS=rat TSS) for all genes expressed in mouse and genes with mouse-specific new exons. Statistical significance indicated by asterisks corresponds to one-way ANOVA, Tukey post hoc test. * $p<0.001$ by one-way ANOVA, Tukey post hoc test. FIG. 8I: Relationship between fold change in gene expression between mouse and rat and new exon PSI value across 9 tissues for Tsku gene. (Right) qRT-PCR analysis of fold change in new exon PSI value (middle) and gene expression (right) in nascent RNA metabolically labeled for 10 minutes with 5-ethynyl uridine, following treatment of NIH3T3 cells with MO targeting new exon 5' splice site relative to control treatment. Mean±SEM of displayed distributions, n=3 biological replicates.  p<0.01, * p<0.001, **p<0.0001 by one-way ANOV A, Tukey post hoc test.

FIG. 9A: a chart showing gene expression levels in mouse for mouse control genes with no evolutionarily new exons (light grey), genes with mouse-specific new exons in tissues where inclusion of the new exon is not detected, PSI<0.05 (grey), and genes with new mouse-specific exons in tissues were the exon is included, PSI>0.05 (pink). While the fold change in gene expression between mouse and rat is significantly different between genes with mouse-specific new exons in tissues with PSI<0.05 and in tissues with PSI>0.05 (see FIG. 8B), gene expression levels in mouse is not. FIG. 9B: a schematic representation of the technique used to label nascent RNA with 4-ethynyl uridine and pool down the nascent RNA with the click-it method. FIG. 9C: charts showing the fold change in nascent RNA levels of Gpr30 (left panel) and Tsku (right panel) in NIH3T3 cells measured by qPCR in RNA metabolically labeled for 10 minutes with 4 ethynyl uridine and relativized using GAPDH, HPRT and HSPCB as housekeeping. Previous to the nascent RNA labelling, NIH3T3 cells were transfected for 24 hours with 20 uM morpholino (MO) targeting the 5' splice site of the new exon in Gpr30 (left panel) and 20 uM MO targeting both the 3' and the 5' splice sites of the new exon in Tsku (right panel). Mean±SEM of displayed distributions. Statistical significance indicated by asterisks corresponds to one-way ANOVA, Tukey post hoc test.

FIG. 10A: a chart showing the distribution of the number of TSSs per gene using RNA-seq data across multiple species and multiple tissues, for all genes expressed in mouse and genes with mouse-specific new exons. Distributions are significantly different by Kolmogorov-Smirnov test. FIG. 10B: charts showing the density distribution of gene expression levels in the mouse brain in control genes with no evolutionarily new exons (light grey) and genes with mouse-specific new exons (dark red), before (left panel) and after (right panel) balance the distribution of gene expression levels in both the control genes and the genes with new exons using the MatchIt package in R. Now with the same distribution of gene expression in both groups (right panel) the dependence between the treatment variable and the other covariates is minimized. FIG. 10C: Distribution of the number of TSSs per gene in the mouse brain using RNA-seq data, for all genes expressed in mouse and genes with mouse-specific new exons, after matching the distribution of gene expression levels between the two groups using the MatchIt package in R. Distributions remain significantly different by Kolmogorov-Smirnov test after matching the gene expression levels between the groups, demonstrating that, independent of gene expression, genes with mouse-specific new exons are enriched in multiple TSSs. FIG. 10D: a chart showing the distribution of the number of H3K4me3 peaks per gene using H3K4me3 ChIP-seq data for all genes expressed in mouse (grey) and genes with mouse-specific new exons (dark red). Distributions are significantly different by Kolmogorov-Smirnov test. Genes with mouse-specific new exons are enriched in H3K4me3 peaks. FIG. 10E: a chart showing the distribution of the number of TSSs per gene using Start-seq data for all genes expressed in mouse and genes with mouse-specific new exons. Distributions are significantly different by Kolmogorov-Smirnov test. Genes with mouse-specific new exons are enriched in multiple TSSs.

FIG. 11A: a chart showing the distribution of the number of TSSs per gene for all genes expressed in rat (light grey) and genes with rat-specific new exons (green). Distributions are significantly different by Kolmogorov-Smirnov test. Genes with rat-specific new exons are enriched in multiple TSSs. FIG. 11B: a histogram showing the proportion of genes with fewer TSSs in mouse (genes w/ mouse TSS<rat TSS), genes with the same number of TSSs in both species (genes w/ mouse TSSs=rat TSS), and genes that have more TSSs in mouse, for all genes expressed in both species (gray) and for genes with rat specific new exons (green). Statistical significance indicated by asterisks corresponds to one-way ANOVA, Tukey post hoc test (NS=not significant).

FIG. 12A: a chart showing the fold change in the number of TSSs used per gene between tissues where mouse-specific exons are included (PSI>0.05) and excluded (PSI<0.05), for mouse and for the same tissues in rat. Evolutionary gain of internal exons and of transcription start sites are associated, only in those tissues where the new exons are included. FIG. 12B: a chart showing the distribution of PSI values of new exons binned by the number of TSSs used in the same gene, for 9 tissues pooled together in mouse. FIG. 12C: a chart showing the distribution of PSI values of mouse-specific new exons for genes with only 1 TSS or 2 TSSs used in the same gene, for 9 tissues plotted separately in mouse. FIG. 12D: a chart showing the ratio between number of TSSs used in mouse and in rat for genes with mouse-specific evolutionarily new exons, binned by location of the exon within the gene. Increased number of TSS is associated with new exons located in the 5'UTR. FIG. 12E: charts showing the density distribution of gene expression levels in the mouse brain in genes with less or same number of TSSs used in mouse (light grey) and genes with more TSSs used in mouse (dark red) than rat, before (left panel) and after (right panel) balance the distribution of gene expression levels in both groups. FIG. 12F: charts showing the distribution of the fold change in gene expression levels between mouse and rat for genes with less or same number of TSSs used in mouse than rat (white) and genes with more TSSs used in mouse than rat (brown), before (left panel) and after (right panel) balance the distribution of gene expression levels in mouse for both groups. Evolutionarily change in gene expression remain significantly different when balancing gene expression levels in mouse for both groups, demonstrating that independently of gene expression levels in one species, genes gaining TSSs in mouse have increased gene expression levels compared to rat.

FIG. 13A: Fold change in the number of TSSs used per gene between mouse and rat for 9 tissues, for mouse control genes with no new exons (white), genes with mouse-specific new exons in tissues where inclusion of the new exon is not detected, PSI<0.05 (grey), and genes with new mouse-specific exons in tissues were the exon is included, PSI>0.05 (pink). Evolutionary gain of internal exons and of transcription start sites are associated. FIG. 13B: Fold change in gene expression between mouse and rat for genes that lost TSSs in mouse (white), genes with same number of TSSs in both species (grey) and genes that gained TSSs in mouse (brown). Gain of TSSs is associated with increased gene expression. *** p<0.001 by one-way ANOVA, Tukey post hoc test. FIG. 13C: a chart showing a histogram of TSS locations in mouse (pink) and rat (grey) in all 9 tissues for genes with mouse-specific new exons, centered on start of mouse new exon or homologous genomic position in rat. In mouse the 0 is set for the start coordinate of the new exon while in rat the position of TSSs of homologues genes with mouse-specific new exons are plot relative to the homologue start coordinate in rat of the mouse-specific new exon. Inset zooms in on locations within 1 kb of new exon. Distributions were smoothed with kernel density estimation by ggplot2 with default parameters. FIGS. 13D-13E: Spearman correlations between the usage of a particular TSS and the PSI value of the new exon across multiple tissues for all TSSs used in genes with mouse-specific new exons, binned by their relative position to the new exon with negative numbers for TSSs located upstream of the new exon and positive numbers for TSSs located downstream of the new exon (FIG. 13D), or in base pairs (FIG. 13E). FIG. 13E: Spearman correlations between TSS PSI and new exon PSI across mouse tissues, for TSSs binned by position relative to mouse-specific exon. FIG. 13F: Difference in expression (in units of fragments per kilobase of exon per million mapped reads, FPKM) in mouse tissues for transcripts including TSSs in tissues where new exon is moderately or highly included (PSI>0.2) versus tissues where new exon is excluded (PSI<0.05), grouped by TSS location relative to new exon.

FIG. 14A: a chart showing TSSs positioning relative to the start coordinate of the new exon in 0 in genes with mouse-specific new exons, for all TSSs used in 9 tissues in mouse. FIG. 14B: a chart showing the comparison of distributions of TSS positions within 5 kb upstream and downstream of new exons between mouse (dark red) and rat (grey) for genes with mouse-specific new exons in all 9 tissues. The 0 position is at the start coordinate of the mouse-specific new exon (mouse) or at the location homologous to this position (rat). Distributions were smoothed with Kernel density estimation. FIG. 14C: a chart showing spearman correlations between the usage of a particular TSS and gene expression levels of the same gene across multiple tissues for all TSSs used in genes with mouse-specific new exons, binned by their relative position to the new exon in base pairs.

FIG. 15A: a chart showing the fold change in inclusion levels of the mouse-specific new exon in Stoml1 gene measured by qPCR of nascent RNA in wild type CAD cells and CRISPR-cas cells with mutations in the 5' splice site of the new exon in blue. Mean±SEM of displayed distributions. Statistical significance indicated by asterisks corresponds to one-way ANOVA, Tukey post hoc test. FIG. 15B: diagrams showing RNAPII profile in Stoml1 gene in CAD cells determined by ChIP assay followed by qPCR with the regions indicated in the top panel. Values of two independent immunoprecipitations relativized to input and the mean value for control IgG antibody are shown for each region. Wild type cells in grey and CRISPR-cas cells with mutations in the 5' splice site of the new exon in dark red. FIG. 15C: diagrams showing a schematic illustration of the Gatad2b gene showing the exon-intron organization in mouse and rat (top) including the alternative last exons (ALE). Also included are charts showing fold change in RNA levels of Gatad2b in NIH3T3 cells measured by qPCR relativized using GAPDH, HPRT and HSPCB as housekeeping, for wild type cells in white and cells transfected for 24 hours with 20 uM morpholino (MO) targeting the 5' splice site of the new exon in Gatad2b in dark red. Mean±SEM of displayed distributions, n=3 independent experiments. The treatment with MO mostly affected transcripts starting in TSS−1 shown by a decrease in inclusion levels that are not compensated by exclusion levels.

FIG. 16A: Fold change in nascent sense (top) and antisense (bottom) RNA levels of Stoml1 in CAD cells measured by qRT-PCR of RNA metabolically labeled for 10 minutes with 5-ethynyl uridine and normalized using housekeeping genes Gapdh, Hprt and Hspcb. Wild type cells in white and CRISPR-Cas cells with mutations in the 5' splice site of the new exon in blue. Mean±SEM of displayed distributions, n=3 independent experiments. A schematic diagram of Stoml1 exon-intron organization is shown at top. FIG. 16B: a chart showing the H-3K4me3 profiles in Stoml1 gene in CAD cells determined by ChIP assay followed by qPCR with the regions indicated in the top panel. Values of two independent immunoprecipitations normalized to input and the mean value for control IgG antibody are shown for each region. Wild type cells (grey) and cells with CRISPR/ cas-mediated mutations in the 5' splice site of the new exon (blue) are shown. FIG. 16C: a schematic illustration of mapping of transcription initiation sites using 5' RACE. Schematic illustrations of 5' RACE products and quantity of clones obtained for each TSSs in wild type (control) NIH3T3 mouse cells (WT) and cells transfected with 20 uM MO targeting the 3' and the 5' splice sites of the new exon in Tsku (MO), n=2 biological replicates. FIG. 16D: a chart showing the H3K4me3 profile in Tsku gene in NIH3T3 cells determined by ChIP assay followed by qPCR with the regions indicated in FIG. 16C. Values of two independent immunoprecipitations relativized to input and the mean value for control IgG antibody are shown for each region. Wild type (control) cells in grey and MO treated cells targeting the 3' and the 5' splice sites of the new exon in blue. FIG. 16E: diagrams showing the Luciferase activity of promoter assay vectors in HeLa cells transfected with the hybrid constructs of the Tsku gen (right). Promoter activities of the corresponding constructs (corrected for transfection efficiency) are presented as fold increase of renilla Luciferase activity relative to firefly Luciferase activity in the same plasmid. Mean±SD, n=3 independent experiments. FIG. 16F: a schematic illustration of mapping of transcription initiation sites of Tsku hybrid constructs using 5' RACE. Schematic illustrations of TSS usage and quantity of clones obtained in NIH3T3 mouse cells transfected with plasmids expressing the corresponding Tsku mutants. FIG. 16G: Model in which creation of a splice site during evolution triggers inclusion of a new internal exon which activates use of an upstream cryptic TSS. In the model, exon recognition by the splicing machinery (SM) in transcripts from the distal promoter activates TSS(s) located proximal and upstream of the exon. Transcripts initiating from the proximal promoter also include the exon, further boosting activity of this promoter.

FIG. 17A: diagrams showing Tsku mouse-specific new exon and skipped exon inclusion and exclusion patternsin NIH3T3 cells (isoform expression for Tsku gene in NIH3T3 cells, measured by RT-PCR) transfected for 24 hours with 20 uM morpholino (MO) targeting the 3' or the 5' or both splice sites of the new exon, for transcripts starting at TSS−2 (upper panel) or at TSS−1 (low panel). FIGS. 17B-17C: charts showing the GTF2F1 (FIG. 17B) and the RNAPII (FIG. 17C) profiles in Tsku gene in CAD cells determined by ChIP assay followed by qPCR with the regions indicated in the top panel. Values of two independent immunoprecipitations relativized to input and the mean value for control IgG antibody are shown for each region. NIH3T3 cells transfected for 24 hours with 20 uM MO control or MO targeting both 3' and 5' splice sites of the new exon. Wild type (WT)=control. FIG. 17D: diagrams showing the fold change in inclusion and exclusion levels of the mouse-specific new exon in Tsku gene and antisense levels from both TSSs measured by isoform-specific qPCRs. Exclusion levels are measured from both alternative first exons to either the following skipped exon or constitutive exon downstream the mouse-specific new exon. NIH3T3 cells were transfected with control MO or MO targeting the 3' or the 5' or both splice sites of the new exon. A decrease in the inclusion level of transcripts starting at TSS−2 is compensated by an increase in the exclusion levels, while total level of transcripts starting at TSS−1 is impaired by the MO. Mean±SEM of displayed distributions. n=3 biological replicates. Statistical significance indicated by asterisks corresponds to one-way ANOVA, Tukey post hoc test. FIG. 17E: charts showing the fold change in total antisense levels from both TSSs in Tsku gene measured by qPCR of nascent RNA in wild type NIH3T3 cells and MO treated cells. Mean±SEM of displayed distributions. Statistical significance indicated by asterisks corresponds to one-way ANOVA, Tukey post hoc test. n=3 biological replicates.

Figure 18A:
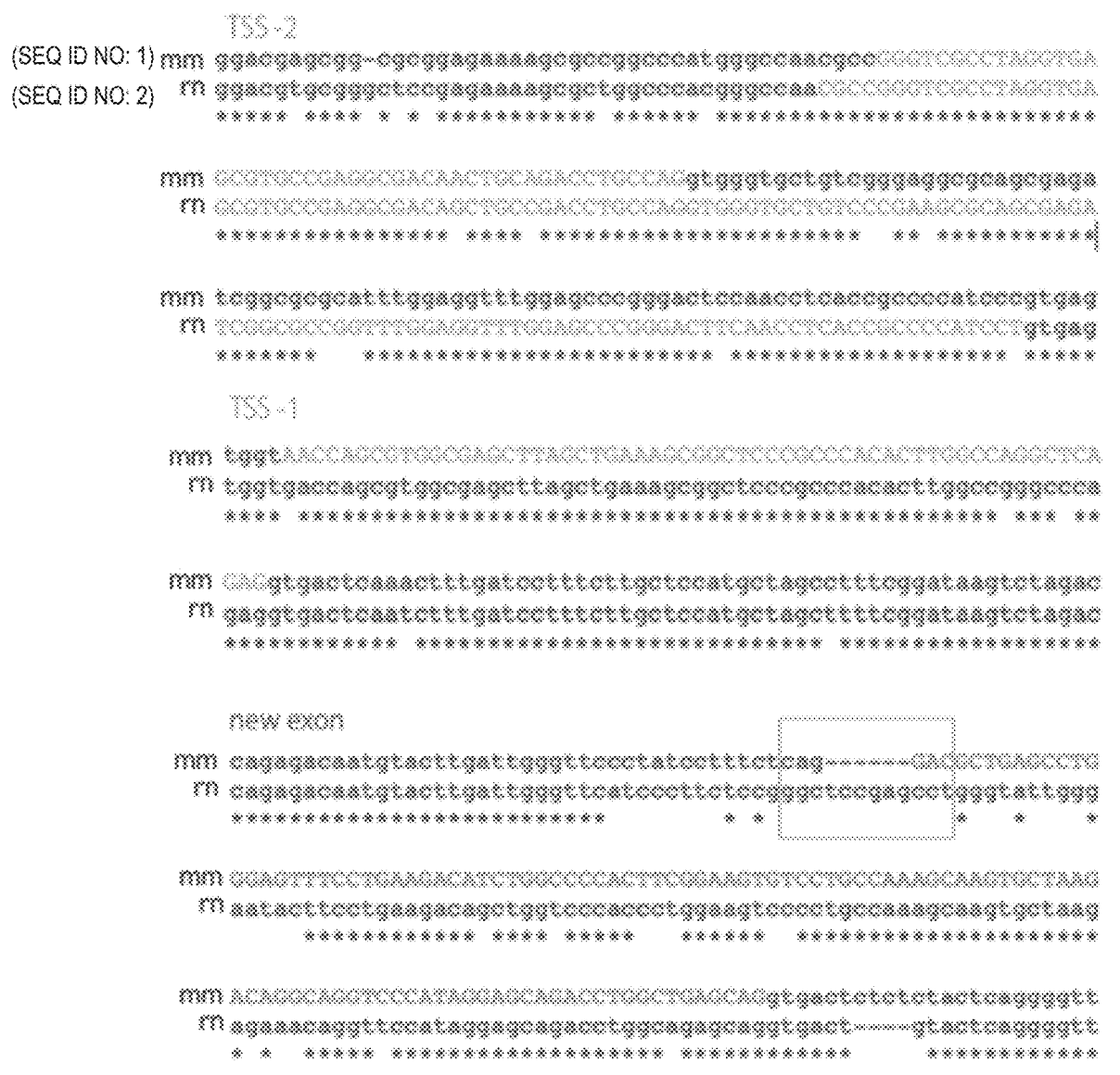

FIGS. 18A-18D include diagrams showing the inclusion of a species-specific new exon enhances gene expression by activating a TSS. FIG. 18A: alignments and identity between mouse (mm) (SEQ ID NO: 1) and rat (rn) (SEQ ID NO: 2) of the DNA sequence of TSS−2, TSS−1 and mouse-specific new exon in the Tsku gene. FIGS. 18B-18C: diagrams showing splicing patterns of the Tsku gen in HeLa cells transfected with the hybrid constructs (FIG. 16E). Total inclusion levels of the mouse-specific new exon in (FIG. 18B) and inclusion/exclusion levels from both TSS−2 and TSS−1 in (FIG. 18C). The creation of the mouse 3' splice site (m+mm 3'ss) or a stronger 3' splice site (rn+strong 3'ss) of the mouse-specific new exon in the rat sequence promotes the inclusion of the mouse-specific new exon in the rat context only when maintaining the wild type 5' splice site (but not in the mm 3'ss+mut 5'ss construct). FIG. 18D: Sequence of 5' end of Tsku transcripts generated by 5' RACE in HeLa cells transfected with rat Tsku constructs with the 3' splice site of the mouse-specific new exon (5' race clone ("clon") A, clone B) aligned to the mouse sequence (mm) and the rat sequence (rn). For 80% of the sequenced transcripts, the 5' end mapped 1 bp upstream of the position of mouse TSS−1 (clone A), while in the remainder the 5' end mapped 19 bp upstream of (clone B) (SEQ ID NOS: 3-7 from top to bottom as seen in FIG. 18D).

FIGS. 19A-19G include charts showing that strong skipped exons favor weak TSSs. FIG. 19A: Spearman correlations between TSS PSI (n=49,911) and skipped exon PSE (SE, n=13,491) in the same gene across mouse tissues for all expressed TSSs in genes with SEs, binned by genomic position relative to the SE. FIG. 19B: charts showing the comparison of distributions of TSS positioning in 9 tissues between genes with mouse-specific new exons (blue) and genes with SEs in mouse (grey). Position 0 is set to the start coordinate of the new exon/skipped exon. Distributions were smoothed with Kernel density estimation. FIG. 19C: a chart showing the distribution of the PSI values of mouse-specific new exons (blue) and SE (grey) in mouse. FIG. 19D: a chart showing the distribution of PSI values of mouse-specific new exons binned by the position of the next upstream TSS used in the same gene. FIG. 19E: a chart showing the distribution of 5' splice site score values of mouse-specific new exons, binned by the relative position to the next upstream TSS used in the same gene in base pairs. 5' splice site scores were calculated using MaxEntScan (Yeo and Burge, 2004). FIG. 19F: a chart showing the distribution of the PSI values of first exons associated with TSSs in genes with mouse-specific new exons (blue) and in genes with SEs in mouse (grey). FIG. 19G: a chart showing the Distribution of PSI values of first exons associated with TSSs in genes with mouse-specific new exons, binned by their relative position to the new exon in base pairs.

FIG. 20A: Expression of alternative first exons (AFE) for all TSSs in genes with mouse-specific new exons in tissues where the new exon is included (PSI>0.05), binned by position relative to the new exon. FIGS. 20B-20C: charts showing the spearman correlations between the usage of TSS and the PSI value of the skipped exon (SE) in the same gene across multiple tissues for proximal and upstream TSSs (within 1 kb upstream the SE) used in genes with SEs in mouse, binned by quartiles of mean PSI values of the TSSs (FIG. 20B) and binned by quartiles of mean SE PSI (FIG. 20C). FIG. 20D: diagrams of exon-intron organization of mouse Zfp672 gene. analysis of expression of Zfp672 in NIH3T3 cells normalized to expression of housekeeping genes Hprt and Hspcb. Data for control cells and cells treated with MO targeting the indicated splice sites (E4.CE and E6.CE). E5.SE is not included in NIH3T3 cells. Inclusion levels of the skipped exons, as well as levels of exon-excluding transcripts from the alternative TSSs (TSS−3, TSS−2, TSS−1) and total gene expression are shown. Scores of 5' splice sites of skipped exons and first exons are listed in bits. Mean±SEM of displayed distributions for n=3 independent experiments. FIG. 20E: a histogram and density of the distribution of the number of TSS with significant difference in expression levels associated with depletion of 250 RBPs. Histogram and density of the distribution of the number of genes with significant changes in promoter usage associated with depletion of 67 splicing factors (upper panel). Mean between two cell lines (HepG2 and K562) is plot for each RBP. FIG. 20F: a schematic illustration of a model showing that the creation of a splice site (ss) during evolution promotes the gain of an evolutionarily new internal exon. In a potential intermediate state, the new exon recruits splicing factors (SF) that co-associate with transcription factors creating a high concentration of RNAPII and core transcription complex that, in turn, activate weak TSSs located proximal and upstream of the splicing event. As a steady state in the derived locus, transcripts start alternatively from multiple TSSs and inclusion of the new exon is coordinated with usage of the most proximal and upstream TSS. This evolutionary shift amplifies the combinatorial possibilities of produced transcripts and greatly expands the modes of gene expression regulation. FIG. 20G: Heat map showing the median Spearman correlation between TSS PSI and SE PSI in the same gene across mouse tissues for SEs with at least one TSS located upstream, in four groups, according to whether the mean TSS PSI (across tissues) and the mean SE PSI were greater than or less than the corresponding median values (across all TSSs and SEs analyzed).

FIG. 22A: a histogram of the distribution of the number of genes with significant changes in promoter usage associated with depletion of 250 RNA binding proteins (RBP), binned by the gene ontology categories of RBPs. Mean±SEM between all RBPs in each gene ontology category for two cell lines (HepG2 and K562) is plot. FIG. 22B: a histogram and density of the distribution of the number of TSS with significant difference in expression levels associated with depletion of 67 splicing factors. Mean between two cell lines (HepG2 and K562) is plot for each splicing factor.

FIG. 23A: Distribution of the number of polyadenylation sites used per gene located 2 kb upstream/downstream of a control set of mouse genes with skipped exons (grey, sePCPA) and genes with mouse-specific new exons (pink, nePCPA). sePCPA and nePCPA are defined in the Example section. FIG. 23B: Distribution of the number of polyadenylation sites used 2 kb upstream/downstream of new exons per gene in tissues where new exon is excluded (PSI<0.05, grey) or included (PSI>0.05, pink), for genes with new exons and at least one nePCPA. Distributions are not significantly different by Kolmogorov-Smirnov test. FIG. 23C: Distribution of the number of polyadenylation sites used 2 kb upstream/downstream of new exons per gene in tissues new exon is excluded (PSI<0.05, grey) and tissues with inclusion of new exons (PSI>0.05, pink) for all genes with new exons. Distributions are not significantly different by Kolmogorov-Smirnov test. FIG. 23D: Scatter plot showing the relationship between the number of nePCPA sites and the fold change in gene expression levels between mouse and rat. These variables are not significantly associated by Spearman correlation test. Polyadenylation sites for 5 tissues in mouse were analyzed using polyA-seq data (Derti et al., 2012).

FIGS. 24A-24B: Difference in TSS usage based on PSI value (FIG. 24A) and FPKM (FIG. 24B) in tissues with high versus low inclusion of skipped exons (SE), in the same gene across multiple tissues for proximal and upstream TSSs (within 1 kb upstream the SE) used in genes with SEs in mouse, binned by quartiles of PSI values of the TSSs. FIG. 24C: Difference between TSS PSI values in tissues with high versus low inclusion of skipped exons (SE), for all weak TSSs (bottom quartile) used in genes with skipped exons in mouse, binned by their position relative to the SE.

FIG. 25A: Gene Ontology analysis of 1777 mouse genes with the strongest EMATS potential. Fold enrichments shown for the most significant categories with asterisk indicating adjusted p-values and color indicating relation to neuron development. FIG. 25B: Histogram of number of genes with significant changes in alternative first exon usage following depletion of 67 splicing factors. Mean number between two cell lines (HepG2 and K562) is plotted for each RBP (top ten splicing factors with greatest number of changes shown in red). FIG. 25C: PPI network for the top 10 splicing factors from (FIG. 25B), colored by Gene Ontology category. Nodes represent proteins and edges represent PPIs. Node and label size are proportional to protein connectivity. The 10 selected splicing factors in red primarily interact with other 65 proteins, generating a network with 75 nodes and 424 edges, a diameter of 5, an average weighted degree of 6.1, an average clustering coefficient of 0.39 and an average path length of 2.1. PPI data are from STRING database (Szklarczyk et al., 2015) (using experimentally determined, database annotated, homology-based, gene fusion and automated text mining interactions). Networks were built using Gephi (http://gephi.org). FIG. 25D: (above) Venn diagram showing the overlap between genes with significant changes in gene expression (GE), alternative splicing of SEs and relative usage of TSSs following knockdown of PTBP1 in human HepG2 cells. (below) Venn diagram showing the overlap between genes with changes in GE, SE and TSSs following knockdown of PTBP1, for human genes with EMATS organization. The overlap is 1.7-fold above background expectation (p<1.6e−20). FIG. 25E: Model for the role of EMATS in dynamic gene expression programs. Growth factor or other stimuli activate transcription factors (TF) and splicing factors (SF). TFs influence gene expression by direct effects on transcription (tx) and indirectly by regulating levels of SFs. Effects of SFs on splicing contribute to gene expression programs by EMATS. In genes with EMATS structure, splicing machinery (SM) or SFs recruit GTFs or RNAPII to activate weak TSS(s) proximal and upstream of the exon. FIG. 25F: Histogram and smoothed density of number of TSSs with significant expression change following depletion of each of 250 RNA binding protein genes. Mean two cell lines (HepG2 and K562) is plotted for each RBP. Distribution of the number of genes with significant changes in promoter usage associated with depletion of 250 RBPs, binned by Gene Ontology Biological Process categories of RBPs. Mean±SEM between all RBPs in each GO category for two cell lines (HepG2 and K562) is plotted. FIG. 25G: Number of genes with significant difference in promoter usage associated with depletion of 67 splicing factors (SF). The right line indicates the cutoff for the top ten splicing factors driving the largest changes in promoter usage, while the left line indicates the cutoff for bottom ten control splicing factors driving the fewest changes in promoter usage. FIG. 25H: Protein interaction network for 10 control splicing factors driving the fewest changes in promoter usage. The control 10 splicing factors in red primarily interact with 88 other proteins, generating a network with 98 nodes and 410 edges, a diameter of 3, an average weighted degree of 4.29, an average clustering coefficient of 0.43 and an average path length of 1.32. Nodes represent proteins and links represent the interactions among them. Node size and label size is proportional to the protein connectivity (number of interactions a protein establishes with others). Protein interaction data were collected from STRING (Szklarczyk et al., 2015)

and networks were built using Gephi (http://gephi.org). FIG. 25I: Exon-intron organization of human BMF gene. RNA-seq analysis of expression of BMF in HepG2 cells following PTBP1 knockdown normalized to expression of control cells. Inclusion levels of the skipped exon, as well as levels of relative usage of the alternative TSSs (TSS–2, TSS–1) and total gene expression are shown. Mean±SEM of displayed distributions for n=2 replicates.

DETAILED DESCRIPTION OF THE INVENTION

Figure 1:
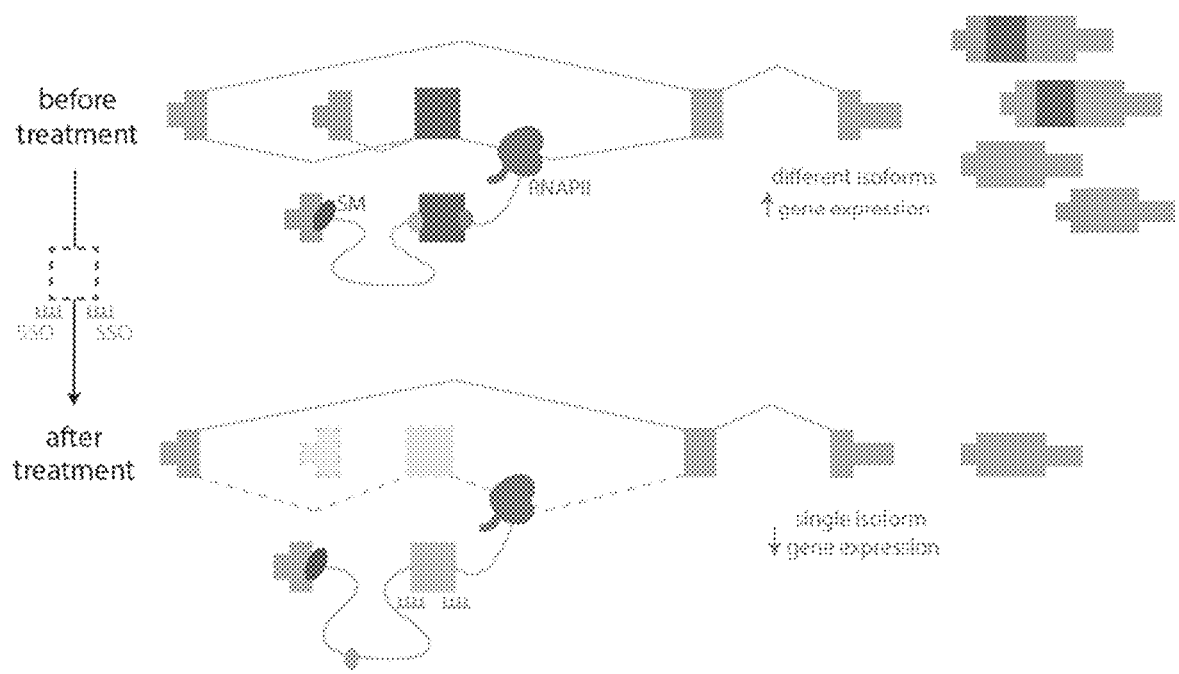
FIG. 1 includes a schematic illustration of the general approach for inhibition of transcription of a gene or isoform by modulating splicing with an SSO. Treatment with a SSO targeted to the 3' or the 5' splice site sequence of a skipped exon inhibits recognition of the exon by the splicing machinery (SM). The resulting "skipping" of the exon by the SM inhibits the most proximal upstream promoter, inhibiting transcription of associated mRNA isoforms and downregulation expression of the gene.

RNA splicing is a frequently regulated process that varies between tissues and species. Although 95% of multi-exon human genes undergo alternative splicing, transcript isoform differences across human tissues are heavily driven by alternative transcription start and termination sites, which are present in more than half of human genes. The processing of RNA transcripts from mammalian genes often occurs nearby in time and space to their synthesis, creating opportunities for functional connections between transcription and splicing. Several links between splicing and transcription are known, and both transcription rate and chromatin structure can influence splicing outcomes in some cases. Early studies suggest that both spliceosome assembly and catalysis of splicing occur in a co-transcriptional manner and it has been recently shown that splicing, transcription initiation, and termination can be coordinated. Splicing can impact transcription elongation rates and in yeast the presence of an intron can generate a transcriptional checkpoint that is associated with pre-spliceosome formation. Furthermore, recruitment of the spliceosome complex can stimulate transcription initiation by enhancing preinitiation complex assembly, and inhibition of splicing can reduce levels of histone 3 lysine 4 trimethyl (H3K4me3), a chromatin mark associated with active transcription. There is evidence that adding an intron to an otherwise intron-less gene often boosts gene expression in plants, animals, and fungi; the mechanisms are not fully understood but impacts on transcription, nuclear export, mRNA stability, and/or translation have been noted.

A key player in coordinating transcription with splicing is RNA polymerase II (RNAPII) itself, as post-translational modifications of its C-terminal domain create a binding platform for splicing factors (recruitment model) and affect the rate of transcription elongation (kinetic model). Several components of the splicing machinery associate with RNA polymerase II (RNAPII) and other transcription machinery. The U1 and U2 small nuclear ribonucleoprotein particles (snRNPs) associate with general transcription factors (GTFs) GTF2H, GTF2F, and the carboxy-terminal domain (CTD) of RNAPII. In addition to its role in splicing, U1 snRNP acts as a general repressor of proximal downstream premature cleavage and polyadenylation (PCPA) sites. The relative depletion of U1 snRNP binding sites upstream in the antisense orientation from promoters (relative to their presence in the downstream sense direction) contributes to frequent termination of antisense transcripts at PCPA sites, resulting in short unstable transcripts. Direct regulation of splicing on transcription initiation sites has not been shown.

In aspects of the invention, an analysis of evolutionarily new exons has suggested that splicing may influence promoter usage, and direct perturbations of splicing by antisense and genetic methods confirmed this link. It has been demonstrated, according to the invention, that splicing impacts gene expression by regulating the usage of alternative transcription start sites (TSSs) and an unanticipated role for exons in the activation of nearby TSSs has been identified.

Figure 2:
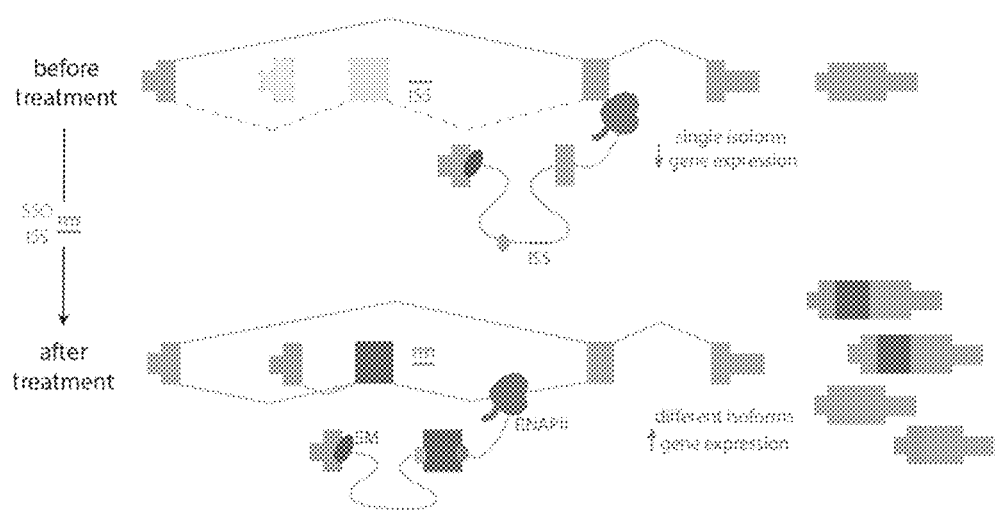
FIG. 2 includes a schematic illustration of the general approach for activation of gene expression and isoform specific activation. Treatment with a SSO targeted to an intronic splicing silencer (ISS) downstream of a skipped exon promotes exon recognition by the splicing machinery (SM). The resulting inclusion of the exon activates the proximal upstream promoter, increasing transcription of associated isoforms and enhancing gene expression.

The present disclosure provides methods for inhibiting or activating the transcription of a gene of interest, or for inhibiting or activating the transcription of specific mRNA isoforms of a gene. The results herein found that inhibition of the splicing of an internal exon with antisense oligonucleotides (ASOs) inhibits transcription from promoters, particularly promoters located nearby and upstream of the exon, and suppresses overall expression of the gene. Furthermore, it was found that the activation of a splice site that enhances the splicing of an internal exon results in an increase in transcription from nearby upstream promoters. As used herein, the term "internal exon" refers to any exon other than the first or last exon of the gene (i.e. an exon flanked by introns). This approach may be used in a therapeutic context to inhibit the expression of a gene or of specific mRNA isoforms of a gene that is mutated, amplified, or overexpressed in a particular disease (FIG. 1). In addition, the approach can be used to boost transcription and expression of a gene or of specific mRNA isoforms of a gene whose increased expression would be protective from a particular disease (FIG. 2). There are numerous examples of genes whose up- or down-regulation would be therapeutic in cancer, neurodegenerative disease and so on.

An essential step in the expression of most human genes, pre-mRNA splicing is the process of intron removal and exon ligation. In human genes that contain introns, splicing is carried out by the spliceosome which recognizes specific sequences in the pre-mRNA including, but not limited to, the 5' splice site and the 3' splice site located at the 5' and 3' ends of each intron, respectively.

ASOs that block access of the splicing machinery to splice sites (or block certain other sites in the pre-mRNA) can shift splicing to exclude ("skip") the targeted exon from the mature mRNA. Herein, such ASOs are referred to as "inhibitory splice-switching antisense oligonucleotides (SSOs)". Other ASOs targeting different parts of the pre-mRNA can shift splicing to increase inclusion of the targeted exon. Herein, such ASOs are referred to as "activating SSOs". The present disclosure teaches that ASOs that inhibit splicing of internal exons (shift splicing to skip the targeted internal exon) can also inhibit transcription from nearby promoters, especially the most proximal promoter located upstream of the exon, and reduce total gene expression. As used herein, the term "upstream" refers to the 3' to 5' direction on a nucleotide sequence and the term "downstream" refers to the 5' to 3' direction on a nucleotide sequence. As used herein, the term "skipped exon" refers to an exon that has been excluded ("skipped") from the mature mRNA.

Figure 3A:
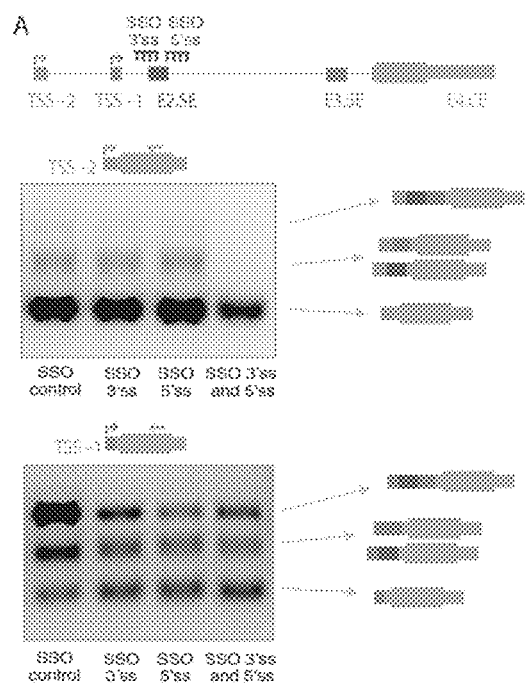
FIGS. 3A-3C include diagrams showing splicing-dependent inhibition of gene expression and transcription from proximal promoter.
Figure 3B:
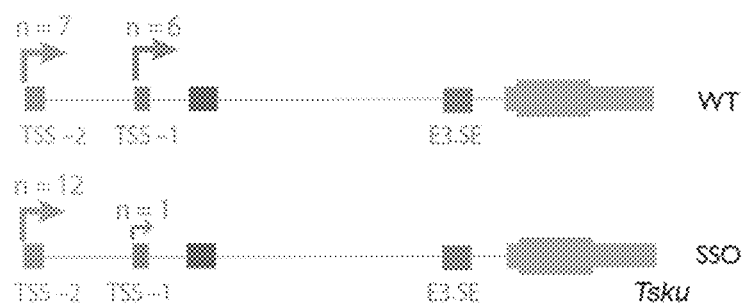
Figure 3C:
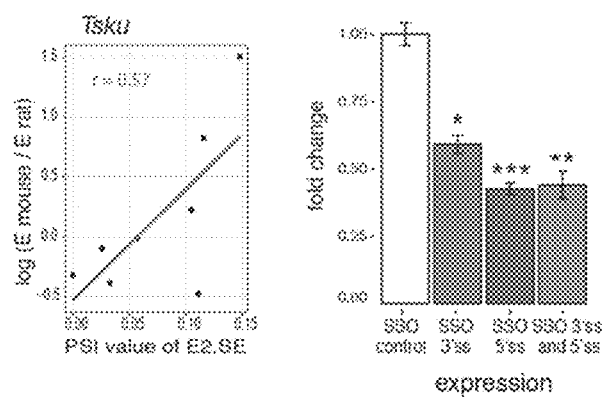
Figure 4A:
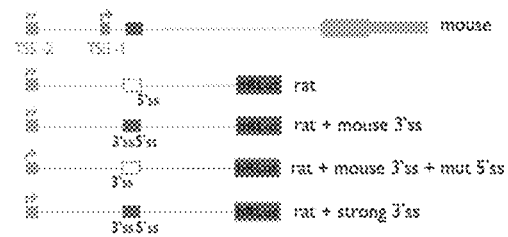
FIGS. 4A-4D include diagrams showing splicing-dependent activation of a proximal promoter and enhancement of gene expression.
Figure 4B:
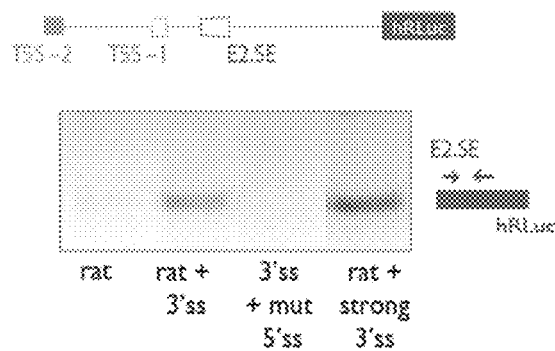
Figure 4C:
Figure 4D:
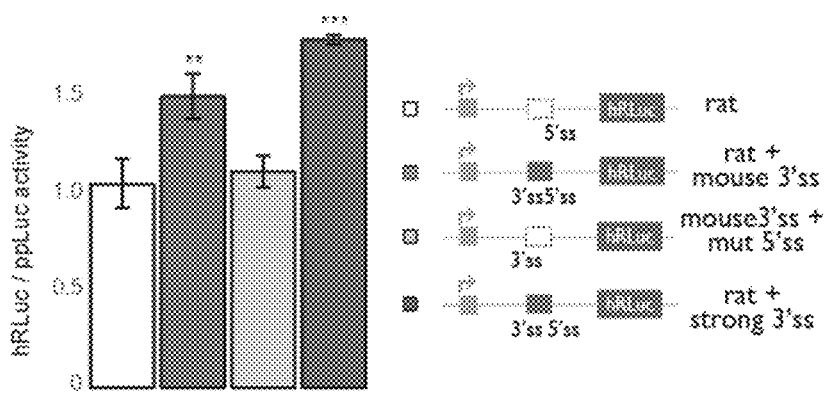

In some embodiments, the methods of the present disclosure show shifting splicing by transfection of ASOs and/or small molecules. Within hours after transfection, the ASOs targeting the splice site sequence of a given exon shift splicing, inhibiting inclusion of the internal exon. The splicing inhibition triggers the inactivation of the most proximal upstream promoter and reduces overall gene expression in cis (FIG. 3).

The ASOs and/or small molecules may target any site in and around an exon whose splicing is to be modulated. These sites may or may not be intronic or exonic enhancer or activator elements or splicing silencer elements. The skilled artisan can identify different oligonucleotides targeting sites in the exon and in the few hundred bases upstream and downstream of the exon, independent of any known splicing regulatory elements based on the guidance provided herein, and then assess by qRT-PCR or other means to identify useful ASOs.

In some embodiments, the methods of the present disclosure involve contacting cells with an ASO (e.g., SSO) and/or small molecule targeted for either the 3' splice site or the 5' splice site. The ASO or small molecule then binds to the respective site. In some embodiments, the methods of the present disclosure include contacting cells with a combination of two types of ASOs or small molecules, whereby one type of ASO or small molecule targets and binds to the 3' splice site, while the other type of ASO or small molecule targets and binds to the 5' splice site.

Thus, in some embodiments, an oligonucleotide may be used that comprises multiple regions of complementarity with a target exon sequence, such that at one region the oligonucleotide hybridizes at or near the 5' end of the target exon sequence and at another region it hybridizes at or near the 3' end of the target exon sequence, thereby modulating splicing activity. In some embodiments, when an oligonucleotide hybridizes both at or near the 5' end and the 3' end of the target exon sequence secondary structure of the target nucleic acid may be effected.

In some embodiments, the methods of the present disclosure include inhibiting an upstream promoter with mutations that block the 3' or the 5' splice site of an internal exon located downstream of the promoter.

Typically, on pre-mRNA transcripts, there are exonic splicing enhancers, which are sequences that promote the splicing of an associated exon when bound to a splicing factor. An SSO targeted for an exonic splicing enhancer (i.e. an inhibitory SSO) blocks the binding of a splicing factor to the exonic splicing enhancer and thus inhibits splicing of that exon, which leads to exclusion of the exon from the mature mRNA (i.e. exon skipping). There are also intronic splicing enhancers, which are located on introns and promote the splicing of a proximal exon. SSOs targeting intronic splicing enhancers can also lead to exon skipping. Typical pre-mRNA sequences can have intronic splicing silencers (ISS), which are sequences on introns that inhibit the splicing of a proximal exon. This proximal exon can be the exon immediately upstream of the ISS or immediately downstream of the ISS. SSOs targeted for the ISS (i.e. activating SSOs) counteract the silencing effect, which activates the splicing of the proximal exon and allows its inclusion in the mature mRNA sequence. To a similar end, an SSO can target an exonic splicing silencer. Herein, the present disclosure shows that the use of activating SSOs can increase the transcription from an upstream proximal promoter and increase the overall gene expression. These intronic and exonic silencers and enhancers are described in Lee and Rio, *Annu. Rev. Biochem.* 84: 291-323, 2015, the relevant disclosures of which are herein incorporated by reference for the purpose and subject matter referenced herein.

Thus, in some aspects, the present disclosure relates to the use of oligonucleotides such as ASOs. ASOs are nucleotide sequences that bind to target sequences on pre-mRNA via Watson-Crick base-pairing. SSOs are a type of ASO associated with splicing and are short modified nucleic acid sequences that bind to regions on the pre-mRNA, thus precluding the interaction between splicing machinery and the bound region of the pre-mRNA transcript. SSOs can be are approximately 15-30 nucleotides long. In some embodiments of the present disclosure, the SSO can be 5, 7, 9, 11, 13, 15, 16, 17, 18, 19, 20, 21, 22, 23, 24, 25, 26, 27, 28, 29, 30, 32, 34, 36, 38, or 40 nucleotides long. The uses and applications of SSOs disclosed herein can also apply to other types of ASOs.

In some embodiments, the region of complementarity of an oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a target. In some embodiments, the region of complementarity is complementary with at least 8 consecutive nucleotides of a target.

Complementary, as the term is used in the art, refers to the capacity for precise pairing between two nucleotides. For example, if a nucleotide at a certain position of an oligonucleotide is capable of hydrogen bonding with a nucleotide at a corresponding position of a target RNA, then the nucleotide of the oligonucleotide and the nucleotide of the target RNA are complementary to each other at that position. The oligonucleotide and target RNA are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the oligonucleotide and target nucleic acid. For example, if a base at one position of an oligonucleotide is capable of hydrogen bonding with a base at the corresponding position of a target, then the bases are considered to be complementary to each other at that position. 100% complementarity is not required.

An oligonucleotide may be at least 80% complementary to (optionally one of at least 85%, 90%, 91%, 92%, 93%, 94%, 95%, 96%, 97%, 98%, 99% or 100% complementary to) the consecutive nucleotides of a target. In some embodiments an oligonucleotide may contain 1, 2 or 3 base mismatches compared to the portion of the consecutive nucleotides of the target. In some embodiments an oligonucleotide may have up to 3 mismatches over 15 bases, or up to 2 mismatches over 10 bases.

In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80 or more nucleotides in length. In some embodiments, the oligonucleotide is 8 to 50, 10 to 30, 15 to 30 or 8 to 80 nucleotides in length.

Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, it has been found that oligonucleotides disclosed herein may increase or decrease expression of a target RNA by at least about 50% (i.e. 150% of normal or 1.5 fold), or by about 2 fold to about 5 fold. In some embodiments, expression may be increased or decreased by at least about 15 fold, 20 fold, 30 fold, 40 fold, 50 fold or 100 fold, or any range between any of the foregoing numbers. In some embodiments, increased expression has been shown to correlate to increased protein expression. Similarly, in some embodiments, decreased expression positively correlates with decreased protein levels.

It is understood that any reference to uses of oligonucleotides or other molecules throughout the description contemplates use of the oligonucleotides or other molecules in preparation of a pharmaceutical composition or medicament for use in the treatment of condition or a disease associated with decreased levels or activity of a protein.

In some embodiments, for the 5' end, oligonucleotides may be used that are fully/partly complementary to 10-60 nts of the target exon sequence 5' end. In some embodiments, all nucleotides of an oligonucleotide may be complementary to the 5' end of a target exon sequence, with or without few nucleotide overhangs that may or may not be complementary to a sequence immediately adjacent to the 5' end of the target exon sequence. In some embodiments, for the 3' end, oligonucleotides may be fully or partly complementary to 10-60 nts of the target exon sequence 3' end. In some embodiments, all nucleotides of an oligonucleotide may be complementary to the 3' end of a target exon sequence, with or without few nucleotide overhangs that may or may not be complementary to a sequence immediately adjacent to the 3' end of the target exon sequence.

In some embodiments, the oligonucleotide comprises a region of complementarity that is complementary with the target exon sequence (e.g., with at least 5 contiguous nucleotides) at a position that begins within 100 nucleotides, within 50 nucleotides, within 30 nucleotides, within 20 nucleotides, within 10 nucleotides or within 5 nucleotides of the 5'-end and/or 3'-end of the target exon sequence. In some embodiments, an oligonucleotide comprises a region of complementarity that is complementary with the target exon sequence (e.g., with at least 5 contiguous nucleotides of the target exon sequence) at a position that begins at the 5'-end and/or 3'-end of the target exon sequence.

In some embodiments, oligonucleotides are provided with chemistries suitable for delivery, hybridization and stability within cells to target splicing. Furthermore, in some embodiments, oligonucleotide chemistries are provided that are useful for controlling the pharmacokinetics, biodistribution, bioavailability and/or efficacy of the oligonucleotides. Accordingly, oligonucleotides described herein may be modified, e.g., comprise a modified sugar moiety, a modified internucleoside linkage, a modified nucleotide and/or combinations thereof. Any of the oligonucleotides disclosed herein may be linked to one or more other oligonucleotides disclosed herein by a linker, e.g., a cleavable linker.

In some embodiments, the ASO is a morpholino oligonucleotide. Morpholino SSOs are a type of antisense oligonucleotide in which the DNA bases are attached to a backbone of methylenemorpholine rings linked through phosphorodiamidate groups. Non-limiting examples of other SSOs that can be applied to the methods of the present disclosure include phosphorothioate oligos, 2'-O-methyl (2'-OMe) oligos and 2'-O-methoxyethyl (2'MOE) oligos. Oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O— N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

Any of the modified chemistries or formats of oligonucleotides described herein can be combined with each other, and that one, two, three, four, five, or more different types of modifications can be included within the same molecule.

In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotides can comprise any combination of the modifications disclosed herein. Examples of these ASOs are provided in Havens and Hastings, *Nucleic Acids Research* 44(14): 6549-6563, 2016, the relevant disclosures of which are herein incorporated by reference for the purpose and subject matter referenced herein.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group.

The 3' position of the oligonucleotide may have a 3' thiophosphate. The oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end. The oligonucleotide may also be Vivo-linked (e.g., Vivo-linked phosphorodiamidate morpholino (VPMO)).

Preferably an oligonucleotide comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Cuff. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

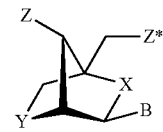

where X and Y are independently selected among the groups —O—,
—S—, —N(H)—, N(R)—, —$CH_2$— or —CH— (if part of a double bond),
—$CH_2$—O—, —$CH_2$—S—, —$CH_2$—N(H)—, —$CH_2$—N(R)—, —$CH_2$—$CH_2$— or —$CH_2$—CH— (if part of a double bond),
—CH=CH—, where R is selected from hydrogen and $C_{1-4}$-alkyl; Z and Z* are independently selected among an internucleoside linkage, a terminal group or a protecting group; B constitutes a natural or non-natural nucleotide base moiety; and the asymmetric groups may be found in either orientation.

One or more substituted sugar moieties can also be included, e.g., one of the following at the 2' position: OH, SH, SCH$_3$, F, OCN, OCH$_3$, OCH$_3$ O(CH$_2$)n CH$_3$, O(CH$_2$)n NH$_2$ or O(CH$_2$)n CH$_3$ where n is from 1 to about 10; C$_1$ to C$_{10}$ lower alkyl, alkoxyalkoxy, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$ CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)](Martin et al, Helv. Chim. Acta, 1995, 78, 486). Other preferred modifications include 2'-methoxy (2'-O—CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

In some embodiments, an oligonucleotide comprises phosphorothioate internucleotide linkages. In some embodiments, an oligonucleotide comprises phosphorothioate internucleotide linkages between at least two nucleotides. In some embodiments, an oligonucleotide comprises phosphorothioate internucleotide linkages between all nucleotides.

It should be appreciated that an oligonucleotide can have any combination of modifications as described herein.

The methods described herein may also be used to modulate transcription via shifting splicing with small molecules or peptides. Small molecules can be used to shift splicing to regulate transcription from a promoter or regulate expression levels of a gene. Non-liming examples of such small molecules are provided in Palacino et al., *Nat. Cherm. Biol.* 11(7):511-7, 2015, the relevant disclosures of which are herein incorporated by reference for the purpose and subject matter referenced herein.

Non-limiting examples of small molecules that can be used to shift or alter splicing include antitumor drugs that inhibit splicing, for example, isoginkgetin, pladienolide B, herboxidiene (GEX1A), spliceostatin A (SSA), and Meayamycin; small molecules that inhibit cdc-2-like-kinases (Clk); benzopyridoindole and pyridocarbazole derivatives; molecules that bind the SF3B spliceosomal complex; for example, pladienolide B (E7107); sudemycins; histone deacetylase inhibitors, for example, sodium butyrate; C6 pyridinium ceramide, suberoylanilide hydroxamic acid (SAHA), LBH589, M344, Phenylbutyrate (PB), trichostatin A (TSA) and valproic acid (VPA); kinetin (6-furfurylaminopurine); cardiotonic steroids, for example, digoxin, lanatoside C, digitoxigenin, and ouabain; tyrphostines, for example tyrphostin 9, tyrphostin AG879; nucleotide analogues, for example, 5-lodotubercidin; benzopyranes, for example, rottlerin; sesquiterpenes, for example, gossypol; pyrazines (amilorides), for example, 3,5-diamino-6-chloro-N-(diaminomethylene) pyrazinecarboxamide monohydrochloride and 2',4'-dichlorobenzamil; Na+/H+ exchange inhibitor, for example, 5-(N-ethyl-N-isopropyl)-amiloride (EIPA); aclarubicin; tetracycline derivatives, for example, PTK-SMA1; polyphenols, for example, curcumin, (−))-epigallocatechin gallate (EGCG), and resveratrol; ribonucleotide reductase inhibitor, for example, hydroxyurea (HU); protein phosphatase inhibitor, for example, sodium vanadate; pseudocantharidins; and beta2-adrenoceptor agonists, for example, salbutamol.

Also disclosed herein are methods whereby the creation of a new splice site activates a new promoter and boosts overall gene expression in cis. The creation of a splice site is sufficient to promote the inclusion of an internal exon in a vector, and increase gene expression levels by activating the usage of a cryptic promoter located proximal and upstream (FIG. 4). In some embodiments of the present disclosure, the splice site is a 3' splice site. In some embodiments of the present disclosure, the splice site is a 5' splice site. Effects on gene expression and promoter-specific inhibition and activation are greatest when: (i) the nearest promoter is located within 1 kb upstream of the targeted exon; (ii) a large change in the splicing of the targeted exon is induced; and (iii) the proximal upstream promoter has relatively weak intrinsic activity.

In some embodiments, the methods, ASOs or small molecules of the present disclosure, can be used to activate transcription from a transcription start site in a gene in a cell by modifying the gene to add a splice site, as described herein, and an exogenous internal exon. As used herein, the term "exogenous" includes, but is not limited to, an internal exons from a different species or an internal exon from a different subject.

As used herein, the terms "transcription start site" and "promoter" are used interchangeably. Herein, a transcription start site (TSS) refers to an initiation site for transcription. It is the site at which RNA polymerase begins synthesis. In some embodiments of the present disclosure, there is one TSS. In some embodiments of the present disclosure there can be multiple transcription start sites within a gene (also referred to as alternative TSSs herein).

Methods for identifying transcript start sites are known in the art and may be used in selecting oligonucleotides that specifically bind to these regions for modifying splicing. In some embodiments, 5' end and/or 3-end oligonucleotides may be designed by identifying 5' start sites using Cap analysis gene expression (CAGE). Appropriate methods are disclosed, for example, in Ozsolak et al. Comprehensive Polyadenylation Site Maps in Yeast and Human Reveal Pervasive Alternative Polyadenylation. *Cell. Volume* 143, Issue 6, 2010, Pages 1018-1029; Shiraki, T, et al., Cap analysis gene expression for high-throughput analysis of transcriptional starting point and identification of promoter usage. *Proc Natl Acad Sci USA*. 100 (26): 15776-81. 2003-12-23; and Zhao, X, et al., (2011). Systematic Clustering of Transcription Start Site Landscapes. PLoS ONE (Public Library of Science) 6 (8): e23409, the contents of each of which are incorporated herein by reference. Other appropriate methods for identifying transcript start sites may also be used, including, for example, RNA-Paired-end tags (PET) (See, e.g., Ruan X, Ruan Y. Methods Mol Biol. 2012; 809:535-62); use of standard EST databases; RACE combined with microarray or sequencing, PAS-Seq (See, e.g., Peter J. Shepard, et al., RNA. 2011 April; 17(4): 761-772); and 3P-Seq (See, e.g., Calvin H. Jan, Nature. 2011 Jan. 6; 469(7328): 97-101; and others.

Disclosed herein, are methods for regulating (i.e. increasing or decreasing) transcription from a transcription start site, by contacting cells with an ASO or small molecule targeted for an internal exon. In some embodiments, the transcription start site is the first (i.e. closest or most proximal) transcription start site upstream of the internal exon. Herein, this is referred to as a proximal transcription start site or proximal upstream transcription start site. In some embodiments, the distance between the regulated TSS (or the most proximal TSS) and the internal exon within the gene is less than 1 kb (kilo base pair). In some embodiments, the distance between the regulated TSS (or the most proximal TSS) and the internal exon is approximately 0.1, 0.2, 0.3, 0.4, 0.5, 0.6, 0.7, 0.8, 0.9, 1.0, 1.1 or 1.2 kb. In some embodiments, the distance between the regulated TSS (or the most proximal TSS) and the internal exon is less than 5 kb. For example, the distance can be 1.5, 2, 2.5, 3, 3.5, 4, 4.5 or 5 kb. In some embodiments, the distance between the regulated TSS (or the most proximal TSS) and the internal exon is more than 5 kb. One of ordinary skill in the art appreciates that in the context of a pre-mRNA transcript, this distance would be described in nucleotides rather than base pairs.

As used herein, the term "intrinsic activity" either refers to a promoter (or TSS) or an exon. In the context of a TSS, the intrinsic activity refers to the intrinsic transcriptional activity or "strength" of the TSS as described elsewhere herein (Example section). Weak and strong promoters can also be identified based on affinity for RNA polymerase. In the context of exons, the intrinsic activity refers to the intrinsic splicing activity or strength of an exon (or skipped exon) as described elsewhere herein (Example section). Exons and their proximal and upstream TSSs were binned into four categories from weak to strong based on their percent splice in (PSI) value, which can be defined as the fraction of mRNA representing the inclusion isoforms. The method used for determining PSI is disclosed in Katz et al., *Nat. Methods* 7(12): 1009-1015, 2010, the relevant disclosures of which are herein incorporated by reference for the purpose and subject matter referenced herein.

As used herein, the terms "targeting," "targeted for" or "targeted to" refer to a multistep process. First, the sequence on the gene (e.g., gene of interest) that the ASO or small molecule should be specific for is selected; this sequence is referred to as the target sequence. The target sequence can be the 3' splice, the 5' splice site on the internal exon, the sequence of an exonic splicing enhancer or an exonic splicing silencer on the internal exon, or an intronic splicing enhancer or an intronic splicing silencer near the internal exon of interest. Thereafter, an ASO or small molecule is synthesized with a sequence that is complementary to the target sequence. In some embodiments, the ASO is synthesized with 100% complementarity to the target sequence. In some embodiments, the ASO has less than 100% complementarity to the target sequence (e.g., 99%, 95%, 90%, 85%, 80%, etc.), but has a sufficient degree of complementarity to minimize non-specific binding of the ASO to non-target sequences, under conditions under which binding occurs (e.g., physiological conditions in in vivo cases). The second step in the process of targeting is the binding (i.e. hybridization) of the ASO or small molecule to the target sequence. As described elsewhere herein, the type of binding between the complementary nucleotides of the ASO and its target sequence is base pair binding (e.g., Watson-Crick base pair binding).

Methods of synthesizing ASOs that are specific for target sequence and/or that have modified backbones are known in the art. Synthesis of specific ASOs with modified backbones is taught in U.S. Pat. Nos. 5,378,825 and 5,541,307, the relevant disclosures of which are herein incorporated by reference for the purpose and subject matter referenced herein. Synthesis of ASOs having morpholino backbone structures are taught in U.S. Pat. No. 5,034,506, the relevant disclosures of which are herein incorporated by reference for the purpose and subject matter referenced herein.

Figure 5:
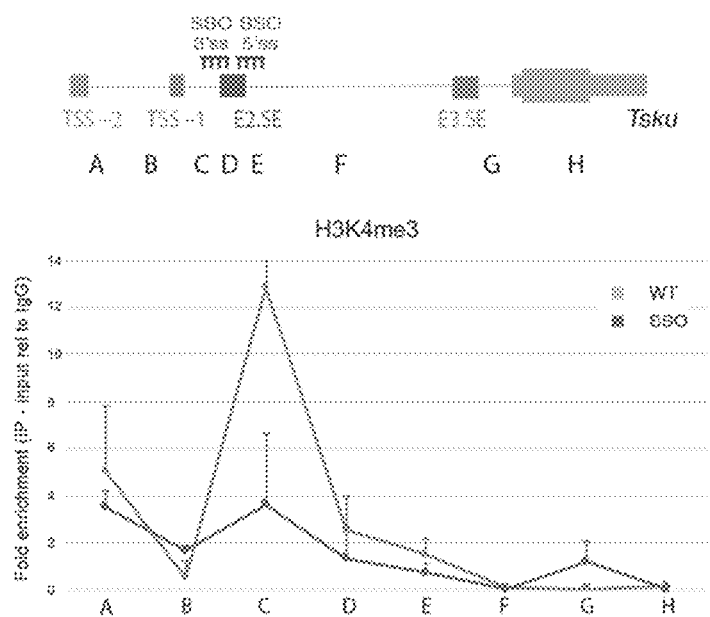
FIG. 5 includes diagrams showing splicing-dependent chromatin changes in proximal promoters. H3K4me3 profile of the Tsku gene in NIH3T3 cells determined by ChIP assay followed by qPCR with the regions indicated in the top panel. Values of two independent immunoprecipitations relativized to input and the mean value for control IgG antibody are shown for each region. Control cells in grey and MO treated cells targeting the 3' and the 5' splice sites of the E2.SE in blue.

There are alternative approaches in the art, such as RNA interference (RNAi) approaches in which oligos base-pair with complementary target mRNA have been used to down-regulate specific genes post-transcriptionally. Moreover, shifting splicing by ASOs for its own sake, or using changes in splicing to alter gene expression by producing isoforms that will have increased or reduced mRNA stability (e.g., via nonsense-mediated mRNA decay (NMD)) has been proposed (herein referred to as "conventional ASO applications"). The novelty of the approach in the present disclosure is the possibility to regulate transcription itself, so that production of transcripts is reduced or increased rather than their stability. With this technology, the co-transcriptional alteration in splicing may not trigger NMD, but it modulates transcription and isoform-specific mRNA synthesis. This distinction could be of particular use in cases where: (i) it is critical to inhibit the mRNA synthesis because the transcripts are not degraded efficiently (e.g., in triplet repeat diseases such as myotonic dystrophy type 1, Huntington's disease, etc.); or (ii) the mRNA naturally has a very short half-life (e.g., the c-myc oncogene), making further reduction in half-life challenging or impossible. The above conventional ASO applications act only as long as the ASO is in the cell. However, with the methods of the present disclosure, changes to chromatin in nearby promoters are observed following transfection of SSOs that target internal exons, suggesting that the disclosed method may result in long-lasting changes in expression, even after the SSO is no longer present in the cell (FIG. 5).

Classical RNAi or ASO designs work efficiently for some genes, but other genes only give modest responses or are refractory to the technology. Since splicing is crucial for the expression of 94% of human genes, the methods disclosed herein can be used in cases where classical RNAi or conventional ASO approaches are not effective or do not achieve sufficient repression of expression. In addition, expression of more than 54% of human genes is controlled by alternative promoters whose regulation can be crucial for cell differentiation and development. Mis-regulation of the usage of alternative promoters is linked to various diseases. Disclosed herein is the first technology that, by impacting splicing, controls the usage of alternative promoters to enhance or inhibit specific sites of transcription initiation.

In some embodiments, delivery of an ASO or small molecule to a cell as described herein results in an increase in expression of a target RNA that is at least 5%, 10%, 20%, 30%, 40%, 50%, 60%, 70%, 80%, 90%, 100%, 200% or more greater than a level of expression of the target RNA in a control cell to which the ASO or small molecule has not been delivered.

Another aspect of the invention provides methods of treating a disease or condition associated with low levels of a particular RNA in a subject. Accordingly, in some embodiments, methods are provided that comprise administering to a subject (e.g. a human) a composition comprising an oligonucleotide, peptide, and/or small molecule as described herein to increase mRNA transcription in cells of the subject for purposes of increasing protein levels. In some embodiments, the increase in protein levels is at least 5%, 10%, 20%, 30%, 40%, 50%, 60%, 70%, 80%, 90%, 100%, 200%, or more, higher than the amount of a protein in the subject before administering. In some embodiments, methods are provided that comprise administering to a subject (e.g., a human) a composition comprising an oligonucleotide, peptide, and/or small molecule as described herein to increase transcription of non-coding RNAs in cells of the subject for purposes of increasing activity of those non-coding RNAs.

As described above, the methods disclosed herein can be used to alter expression levels and inhibit or activate specific promoters of a gene of interest. For example, cancer develops as a consequence of the accumulation of driver somatic alterations that change gene expression programs and isoform levels. With this technology, while an SSO inactivating the splicing of an internal exon of an over-expressed oncogene could be used to inhibit its expression, a SSO activating the splicing of a tumor suppressor gene can be used to boost its transcription. Furthermore, by inhibition/activation of specific promoters triggered by splicing inhibition/activation, the disclosed design can impact where transcription of a gene starts. Cancer-related genes that represent interesting potential targets include oncogenes and anti-oncogenes (e.g., the p53 gene, TP53). As used herein, the term "anti-oncogene" refers to a tumor suppressor gene. These are negative regulators of cell division that protect the cell from the uncontrolled cell growth that is characteristic of cancer. Non-limiting example of tumor suppressor genes that can be targeted using the methods disclosed herein include pRb, PTEN, pVHL, APC, CD95, ST5, YPEL3, ST7, and ST14. Non-limiting examples of antioncogenes that can be targeted using the antisense oligonucleotides (e.g., splice-switching antisense oligonucleotides), small molecules or methods of the present disclosure include APC, IL2, TNFAIP3, ARHGEF12, JAK2, TP53 (p53), ATM, MAP2K4, TSC1, BCL11B, MDM4, TSC2, BLM, MEN1, VHL, BMPRIA, MLH1, WRN, BRCA1, MSH2, WT1, BRCA2, NF1, CARS, NF2, CBFA2T3, NOTCH1, CDH1, NPM1, CDH11, NR4A3, CDK6, NUP98, CDKN2C, PALB2, CEBPA, PML, CHEK2, PTEN, CREB1, RBI, CREBBP, RUNX1, CYLD, SDHB, DDX5, SDHD, EXT1, SMARCA4, EXT2, SMARCB1, FBXW7, SOCS1, FH, STK11, FLT3, SUFU, FOXP1, SUZ12, GPC3, SYK, IDH1, and TCF3.

As used herein, the term "oncogene" refers to a gene that promotes cancer. They can first manifest as proto-oncogenes, which are normal genes that predispose a cell to cancer in the event of their mutation or upregulation. These oncogenes can also inhibit apoptosis, leaving the uncontrolled cell growth that is characteristic of cancer unchecked.

Non-limiting examples of oncogenes that can be targeted using the antisense oligonucleotides (e.g., splice-switching antisense oligonucleotides), small molecules or methods of the present disclosure include ABL1, EVI1, MYC, ABL2, EWSR1, MYCL1, AKT1, FEV, MYCN, AKT2, FGFR1, NCOA4, ATFI, FGFR1OP, NFKB2, BCL11A, FGFR2, NRAS, BCL2, FUS, NTRK1, BCL3, GOLGA5, NUP214, BCL6, GOPC, PAX8, BCR, HMGA1, PDGFB, BRAF, HMGA2, PIK3CA, CARD 11, HRAS, PIM1, CBLB, IRF4, PLAGI, CBLC, JUN, PPARG, CCND1, KIT, PTPN11, CCND2, KRAS, RAF1, CCND3, LCK, REL, CDX2, LMO2, RET, CTNNB1, MAF, ROS1, DDB2, MAFB, SMO, DDIT3, MAML2, SS18, DDX6, MDM2, TCLIA, DEK, MET, TET2, EGFR, MITF, TFG, ELK4, MLL, TLX1, ERBB2, MPL, TPR, ETV4, MYB, USP6, and ETV6.

Figure 6:
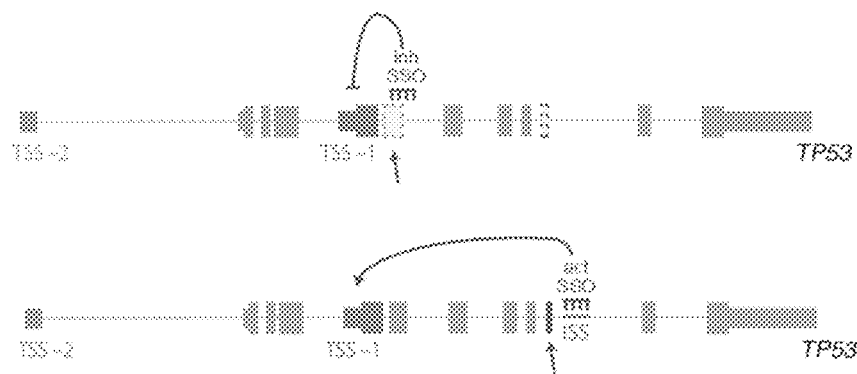
FIG. 6 includes a schematic illustration of potential applications to alter TP53 expression based on gene structure of the human TP53 gene locus. Inhibitory and activating SSO could be used to modulate expression levels of p53. Generally speaking, it may be desirable to increase expression of p53 in cancers. However, different isoforms have somewhat different activities, so isoform-specific regulation may also be of interest. In the top panel, an inhibitory SSO (inh SSO) targeted to the constitutive exon located 100 nucleotides downstream of the proximal promoter could be introduced to inhibit splicing of the exon and trigger the inactivation of the proximal promoter. In the bottom panel, an activating SSO (act SSO) targeting a silencing element of the skipped exon located 1600 nucleotides downstream (e.g., an ISS) can be used to activate the inclusion levels of an alternative exon (pink) and potentially activate use of the proximal promoter.

An inhibitory SSO targeted to the nearest downstream exon can be used to inhibit transcription from the proximal promoter and downregulate overall gene expression, while an activating SSO targeted to a further downstream skipped exon can be used to activate transcription from the proximal promoter and enhance overall gene expression (FIG. 6).

In some embodiments, the methods of the present disclosure can be used to treat a tumor by upregulating the expression of p53 in the tumor tissue, when it has been shown that p53 expression is low (p53 deficient). This may trigger p53-mediated apoptosis to combat the progression of the cancer. In some embodiments, where p53 is mutated and results in the translation of truncated and/or dysfunctional proteins, the methods of the present disclosure can be used to inhibit the expression of p53. In some embodiments, p53 mutations are gain of function mutations that yield proteins that actively contribute to the progression of the cancer. In such cases, inhibitory SSOs can be used to reduce transcription of the p53 gene.

Figure 7:
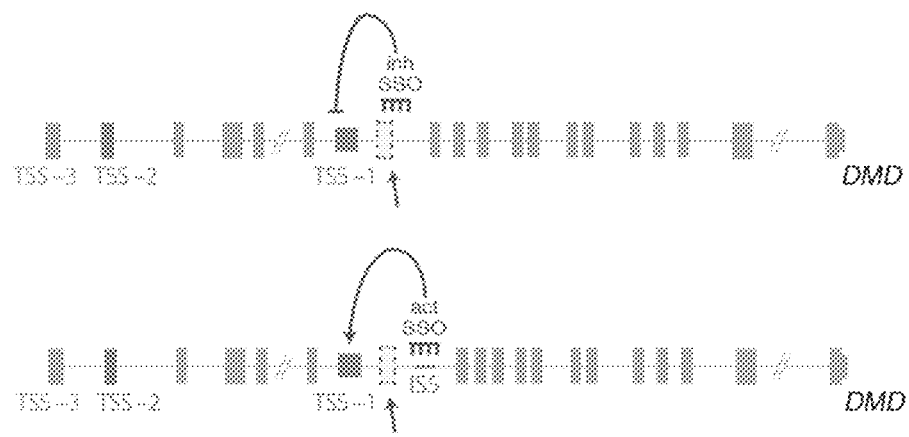
FIG. 7 includes a schematic illustration of potential applications to alter expression of dystrophin based on the gene structure of the human DMD gene locus. Inhibitory and activating SSO could be used to modulate expression levels of the Duchenne muscular dystrophy gene. In Duchenne muscular dystrophy, for therapeutic purposes it is generally desirable to increase expression. But particular isoforms may have different functions, so for completeness applications for both inhibition and activation of expression are shown. In the top panel, an inhibitory SSO (inh SSO) targeted to the skipped exon located 4000 nucleotides downstream of the proximal promoter can be transfected to inhibit splicing of the exon and trigger the inactivation of the proximal promoter. In the bottom panel, an activating SSO (act SSO) targeting a silencing element of the same skipped exon (e.g., an ISS) can be used to activate the inclusion levels of the exon and trigger the activation of the proximal promoter.

In addition, the methods of the present disclosure can be used to regulate transcription levels of other genes with potential therapeutic benefits, including dystrophin, which is associated with Duchenne muscular dystrophy. Duchenne muscular dystrophy is an X-linked recessive disorder caused by mutations in the dystrophin gene (DMD), which is the largest gene in the human genome, containing 79 exons. Methods used for the treatment of Duchenne muscular dystrophy are provided in Nowak et al., *EMBO Rep.* 5(9): 872-876, 2004. Approximately 70% of DMD cases can be attributed to deletions of exons in the dystrophin gene that shift the mRNA reading frame. This has adverse effects on pre-mRNA processing. One such effect is the presence of premature termination codons that lead to translation of truncated dysfunctional dystrophin protein. Skipping exons can correct the reading frame. Examples of exons that can be targeted by inhibitory SSOs are provided in Havens and Hastings, *Nucleic Acids Research* 44(14): 6549-6563, 2016, the relevant disclosures of which are herein incorporated by reference for the purpose and subject matter referenced herein. As disclosed herein, once the correct isoform can be translated using SSO targeting and correction of the mRNA reading frame, an activating SSO can be used to increase gene express of the desired dystrophin isoform(s). Alternatively, an activating SSO can be used to increase gene expression of a gene or isoform of a gene that can compensate for a defective protein (e.g. utropin in DMD cases). An inhibitory or an activating SSO targeted to the nearest downstream exon could potentially be used to inhibit or boost transcription from the proximal promoter and regulate overall gene expression (FIG. 7).

In some embodiments of the present disclosure, it may be desirable to down-regulate the NOTCH2 gene in Alagille syndrome (AGS). One potential target is the non-coding exon 2 of NOTCH2, which is located 2 kb from a promoter. ASOs (e.g., SSOs) or small molecules that inhibit inclusion of this exon can be used to inhibit expression of the gene.

Multiple endocrine neoplasia type 1 (MEN1) is a hereditary condition associated with tumors of the endocrine glands. In some embodiments of the present disclosure, it may be desirable to down-regulate the MEN1 gene. One potential target is the non-coding exon 2 of MEN1, which is located 200 nucleotides from a promoter. ASOs (e.g., SSOs) or small molecules that inhibit inclusion of this exon can be used to inhibit expression of the gene.

Reduce MLH3 expression have been associated with cancer, hypertension and diabetes mellitus. To up-regulate the MLH3 gene, one potential target is to the alternative exon 2, which is located 3.5 KB from a promoter. ASOs (e.g., SSOs) or small molecules that boost (i.e. increase) inclusion of this exon can be used to boost expression of the gene.

In some embodiments of the present disclosure, it may be desirable to up-regulate the SMN2 gene in spinal muscular atrophy (SMA). There are no potential target exons proximal to the promoter as the first intron in SMN2 is more than 10 kb long. One possible strategy is to create splice sites 1 kb downstream of the promoter that will add an exogenous internal exon. Splice sites that promote inclusion of this exon would boost expression of the gene.

As used herein, the term "contacting" refers to in vitro methods of contacting as well as in vivo methods of contacting. The in vitro methods of contacting cells with an ASO or small molecule involve transfection of the cells with an ASO or small molecules. As used herein, the term "transfection" refers to the artificial delivery and introduction of nucleic acids (e.g., SSOs), into a cell (e.g., eukaryotic cell). Methods of transfection are well established in the arts and range from chemical, to biological, and to physical methods. Chemical methods include, but are not limited to, calcium phosphate transfection, cationic polymer transfection, lipofection, and DEAE-Dextran-mediated transfection. Other methods of transfection include, but are not limited to, electroporation, sonoporation, cell squeezing, impalefection, optical transfection, protoplast fusion, Magnetofection™, and particle bombardment. Non-limiting examples of cells that can undergo transfection as described herein include NIH 3T3 fibroblast cells, HeLa cells, and CAD cells.

In some embodiments, the SSO is contacted to a cell by contacting the cell with a vector that codes for the SSO. This can be in vitro or in vivo. As used herein, a "vector" may be any of a number of nucleic acids into which a desired sequence or sequences may be inserted, for example, by restriction digestion and ligation or by recombination for transport between different genetic environments or for expression in a host cell. Vectors are typically composed of DNA, although RNA vectors are also available. Examples of vectors include, but are not limited to plasmids, fosmids, phage lambda, cosmids, single stranded phages, expression vectors, artificial chromosomes, adeno-associated virus (AAV) vectors, and retroviral vectors. These vectors can be cloned with a sequence that codes for the SSO.

Cloning, or molecular cloning, is known in the art (see, e.g., Current Protocols in Molecular Biology, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., Nature Methods 6(5):343-345 (2009); the teachings of which relating to molecular cloning are herein incorporated by reference).

In some embodiments, the term "contacting" refers to the administration of ASOs or small molecules to a tissue in a subject. For example, the ASOs or small molecules can be administered in vivo as an injection, using different deliver routes. The ASOs or small molecules of the present disclosure can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In some embodiments, to target the CNS, ASOs or small molecules can be administered into cerebral spinal fluid intracerebroventricularly or intrathecally.

In some embodiments, the ASOs or small molecules may be administered in the form of a drug. The drug would be a sterile composition comprising the ASOs or small molecules in inactive form and a pharmaceutically acceptable carrier. As used herein, the term "drug" requires that a compound or composition be nontoxic and sufficiently pure so that no further manipulation of the compound or composition is needed prior to administration to the subject. The term "carrier" denotes an organic or inorganic ingredient, natural or synthetic, with which the cells, nanoparticles and/or agent(s) are combined to facilitate administration. The components of the pharmaceutical compositions are combined in a manner that precludes interaction that would substantially impair their desired pharmaceutical efficiency. Moreover, for animal (e.g., human) administration, it will be understood that preparations should meet sterility, pyrogenicity, general safety and purity standards as required by the Food and Drug Administration (FDA) Office of Biological Standards. The compounds are generally suitable for administration to humans or mammals.

As used herein, the term "pharmaceutically acceptable carrier" refers to one or more compatible solid or liquid filler, diluents or encapsulating substances which are suitable for administration to a human or other subject contemplated by the disclosure. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Pharmaceutical compositions and carriers for the administration of ASOs are disclosed in U.S. Pat. Nos. 6,133,246 and 6,080,580, the relevant disclosures of which are herein incorporated by reference for the purpose and subject matter referenced herein. Except insofar as any conventional carrier is incompatible with the active ingredient, its use in the therapeutic or pharmaceutical compositions is contemplated.

In some embodiments the subject is a human. In some embodiments, the subject is an animal (e.g., animal model).

In other embodiments the subject is a mouse or rat. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., rats, rabbits, etc.), and the like.

In some embodiments, the animal model is a model of cancer. The cancer can be a carcinoma, a sarcoma or a melanoma. Carcinomas include, but are not limited to, basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Impacts of pre-mRNA processing on mRNA stability are well known, but effects on transcription are less understood. Alternative start and termination sites drive a substantial portion of transcript isoform differences between human tissues. Recent analyses of full-length mRNAs suggest that transcription starts and splicing may be coordinated. However, whether exon splicing commonly impacts transcription start site (TSS) location and activity remains unknown.

Herein a phenomenon called "exon-mediated activation of transcription starts" (EMATS) is described in which the splicing of internal exons, especially those near gene 5' ends, alters gene expression by influencing which TSSs are used. The results demonstrate that exon splicing activates transcription initiation locally in thousands of mammalian genes, including many involved in brain development. The findings also indicate that activation or repression of gene expression for research or therapeutic purposes may commonly be achievable by manipulation of splicing.

Herein, it was observed that evolutionary gain of new internal exons is associated with gain of nearby transcription start sites. Inhibition of specific splicing events reduces the use of nearby transcription start sites and suppresses gene expression, suggesting that splicing impacts nearby transcription initiation. Furthermore, creation of a new splice site can be sufficient to activate usage of a cryptic transcription start site nearby. These effects act locally as transcription start sites most impacted by splicing are located proximal and upstream of the location of splicing. These findings support an unanticipated evolutionary and regulatory impact of splicing on the spectrum of promoters used by a gene and on expression level.

Materials and Methods

RNA-Seq and genome builds. The RNA-seq data from 9 tissues from mouse and rat associated with Merkin et al., 2012, submitted to NCBI Gene Expression Omnibus (accession no. GSE41637), were mapped to mm9 and rn4 respectively, and processed using TopHat and Cufflinks. Alternative splicing and PSI values were analyzed using MISO. Exons were defined as in Merkin et al., 2012 as having FPKM≥2 and meeting splice site junction read requirements implicit in the TopHat mapping. Exons with 0.05%<PSI<97% in at least one tissue and two individuals were categorized as skipped exons (SE). Exons with PSI>97% in all expressed tissues were defined as constitutive exons (CE), if the gene was expressed in at least three tissues and two individuals. Genomic and splicing ages were defined as in Merkin et al., 2015 by the pattern of species with genomic regions aligned to the exon or with an expressed region in the orthologous gene overlapping the aligned region, respectively. Open reading frames (ORFs) were annotated as in Merkin et al., 2012 and used to classify exons as located in the 5' UTR, 3' UTR or coding region.

Cell lines, cell culture, and treatments. NIH3T3 and HeLa cells were grown in DMEM, with high glucose and pyruvate (Gibco), supplemented with 10% fetal bovine serum (FBS). CAD cells were grown in DMEM/F12 (Gibco) supplemented with 10% FBS. For treatment with morpholinos (MO) (Gene Tools), 20 uM of morpholino targeting 5' or 3' splice site or MO control was added with endoporter (Gene Tools) to cells plated at low confluence and left for 24 hs.

CRISPR sgRNA design, genetic deletions with CRISPR/Cas9 and genotyping by PCR. CRISPR-Cas cell lines to knock out the 5' splice site of Stoml1 were generated using the protocol described in Ran et al., 2013. The single-guide RNA was design to target the 5' splice site in silico via the CRISPR Design Tool (http://tools.genorne-engineering.org) and clone in the Cas9 expression plasmid (pSpCas9). After transfecting CAD cells with the plasmid expressing Cas9 and the correct sgRNA, clonal cell lines were isolated and indel mutations detected by the SURVEYOR nuclease assay. Positive clones detected were then amplified by PCR, subcloned into TOPO-TA plasmids, and individual colonies were sequenced to reveal the clonal genotype.

RNA Extraction, RT-PCR and qPCR. Total RNA was extracted using the RNA-easy kit (Quiagen) according to the manufacturer's protocol. Reverse transcription using M-MLV reverse transcriptase (Invitrogen) and random primers was performed according to the provider's instructions. All PCR conditions and primer sequences are available upon request. For nascent RNA extraction, RNA was metabolically labeled with 4-Ethynil Uridine for 10 minutes using click-it (Invitrogen) and labeled RNA was extracted and amplifies according to the provider's instructions.

ChIP and antibodies. Chromatin immunoprecipitation was performed using ChIP kit (invitrogen) according to the manufacturer's recommendations. Each immunoprecipitation used 10 μg of H3K4me3 (PA5-17420) antibody from Invitrogen, 10 μg of RNA polymerase II (ab817) antibody from Abcam, 10 μg of Transcription Factor IIFI (GTFIIFI) (PA5-30050) antibody from Invitrogen and 10 μg of Rabbit IgG antibody from Invitrogen as a negative control. DNA was purified and quantitative PCR analysis was performed using SYBR green. Immunoprecipitated chromatin was normalized to input chromatin and control IgG antibody. All primer sequences and real time PCR conditions are available upon request.

5' RACE. 5' RACE experiments were performed with 5' RACE System for Rapid Amplification of cDNA Ends (Invitrogen) using three gene-specific primers (GSP) that anneals to the known region and an adapter primer that targets the 5' end. Products generated by the 5' RACE procedures were subcloned into TOPO-TA vectors and individual colonies were sequenced.

Plasmids and luciferase activity assay. Rat Tsku genomic region and mutants were cloned in the psiCHECK backbone. For transfection assays, 1 µg plasmid was transfected into each well of a 6-wells culture plate using Lipofectamine 2000 reagent (Life Technologies) according to the manufacturer's recommendations and cells were harvest after 24 hours. The Dual-Luciferase® Reporter Assay System (Promega) was used to measure luciferase activity.

Definition of new exons. Data of evolutionarily new exons is available in Merkin et al., 2015 as well as here in Tables 1 and 2. Evolutionarily new exons were identified as in Merkin et al., to 2015. Genomic mappings of mouse and rat RNA-seq data were combined with whole-genome alignments to classify exons as species-specific. Only internal and unique exons were analyzed. Alternative first and last new exons were excluded as new exons because they are not primarily regulated by the splicing machinery and thousand exons that aroused from intra-genic duplications were excluded because they are not unique. 1,089 mouse exons were classified as mouse-specific exons and 1,571 rat exons were classified as rat-specific exons, as they were detected in RNA-seq data from mouse or rat respectively, but not from any other species (Table 1 and Table 2). Only 159 mouse genes and 276 rat genes contain more than 1 novel exon, indicating that most genes that contained new exons had only one.

Transcription start sites annotation. TSSs in mouse were identify using Start-seq data from Scruggs et al., 2015 from GEO (accession number GSE62151) in which high-throughput sequencing of nascent capped RNA species from the 5'-end allows for precise definition of TSSs at nucleotide resolution. TSSs were defined within 2,000 nucleotide search windows centered on RefSeq-annotated TSSs, using the location to which the largest number of Start-RNA reads aligned. Very closely spaced TSSs with a distance of less than 50 nucleotides were considered a single TSS in FIG. 8G. To identify TSSs in the same RNA-seq data used to classify new exons, data from Merkin et al., 2012 (GEO accession no. GSE41637) mapped with TopHat and Ensembl Release (Ensembl) annotations was used. As in Merkin et al., 2012, Cufflinks version 1.0.2 was used to identify novel transcripts. The set of TSSs from each library identified from novel transcripts as the start site of the first exon, along with the existing Ensembl annotations, were compiled into a single set of annotations using Cuffcompare. Cufflinks was then used on each library to quantitate the same set of transcripts (Table 3). Number of TSS were also approximated by the number of H3K4me3 peaks assigned to each gene with ChIP data from Yu et al., 2015 (GEO accession numbers GSE59896 and GSE59998).

New Exon Inclusion, usage of TSSs and Species-Specific Expression Changes. Genes with new exons were considered all genes with a new exon with PSI>0.05% in any given tissue of the 9 tissues sequenced. Genes were grouped as control genes with no new exons and genes with new exons divided by whether the exon was included or not in a given tissue. The number of TSSs used in each gene in each tissue was calculated and considered genes gaining TSSs in mouse, genes gaining TSSs in rat and genes with same number of TSSs in both species depending on the ratio of TSSs for each species in each gene in each tissue or counting all tissues at the same time. Gene expression in mouse was compared to that in rat by taking the ratio of mouse to rat expression.

Definition of new exon-proximal cleavage and polyadenylation sites. PolyA-seq data from five mouse tissues is available in Derti et al (Derti et al., 2012). Polyadenylation sites were identified using available polyA-seq data from the five mouse tissues (brain, liver, kidney, muscle, testis) (Derti et al., 2012). Only reads aligning to unique loci were retained and ends of reads within 25 nt of each other on the same strand were clustered. Polyadenylation sites were considered to be new exon-proximal cleavage and polyadenylation (nePCPA) sites if they were located within 2 kb upstream or downstream of a new exon, and as skipped exon-proximal cleavage and polyadenylation (sePCPA) sites if they were located within 2 kb upstream or downstream of skipped exons.

Software for data analysis, graphical plots and statistical analyses. For data analysis, R Bioconductor, BEDTools, SamTools, GenomicRanges and Integrative Genomics Viewer were used. All statistical analyses were performed in R (v.3.4.2) and graphical plots were made using the R package ggplot2. Lower and upper hinges of box plots correspond to the first and third quartiles (25th and 75th percentiles). The upper and lower whiskers extend from the hinge to the largest and lower value no further than 1.5×IQR (interquartile range) respectively. Notches give roughly 95% confidence interval for comparing the medians. Statistical significance is indicated by asterisks ($*p<0.05$, $p<0.01$, $*p<0.001$, $**p<0.0001$, $***p<0.00001$).

Figure 8A:
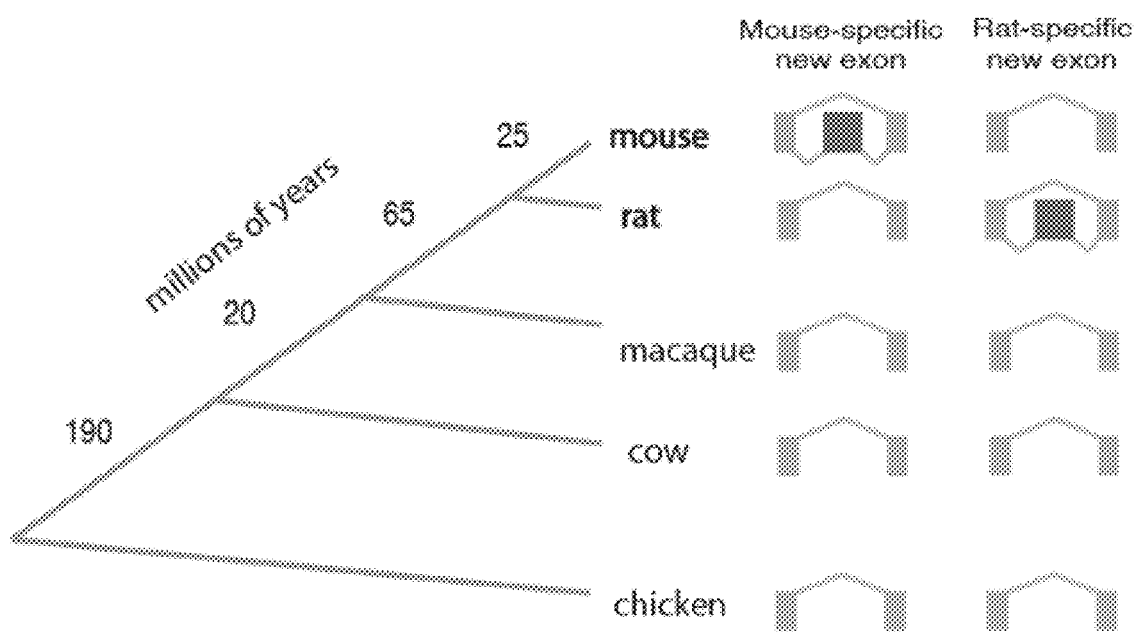
FIGS. 8A-8I include diagrams demonstrating that splicing enhances gene expression in the presence of multiple TSS.
Figure 8B:
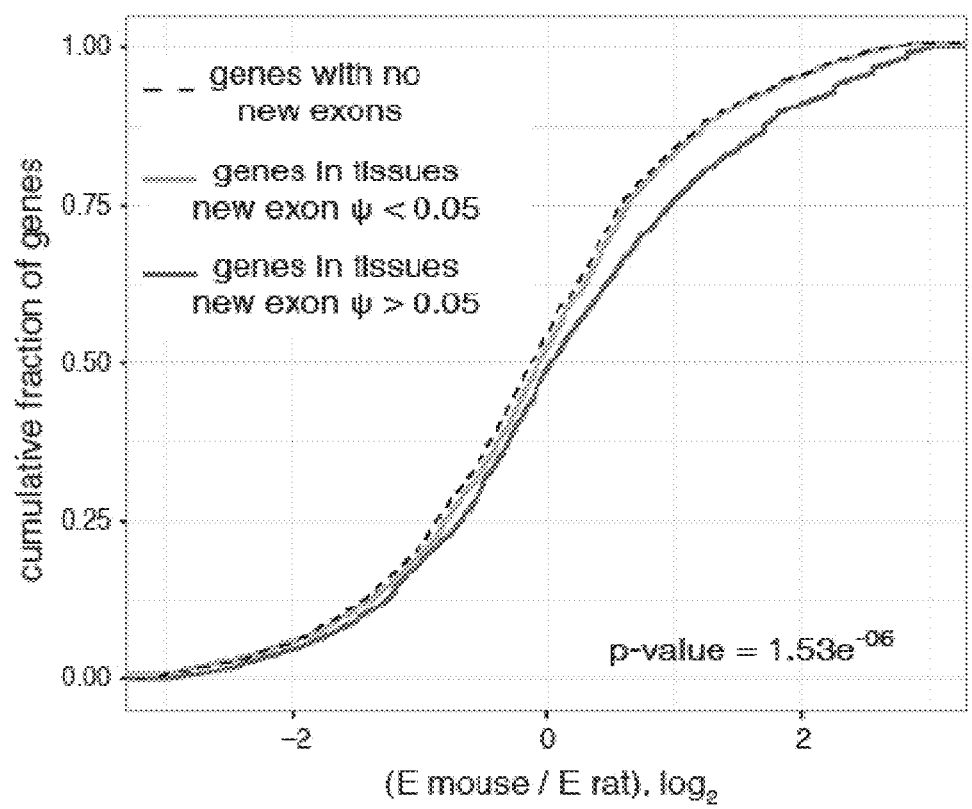
Figure 8C:
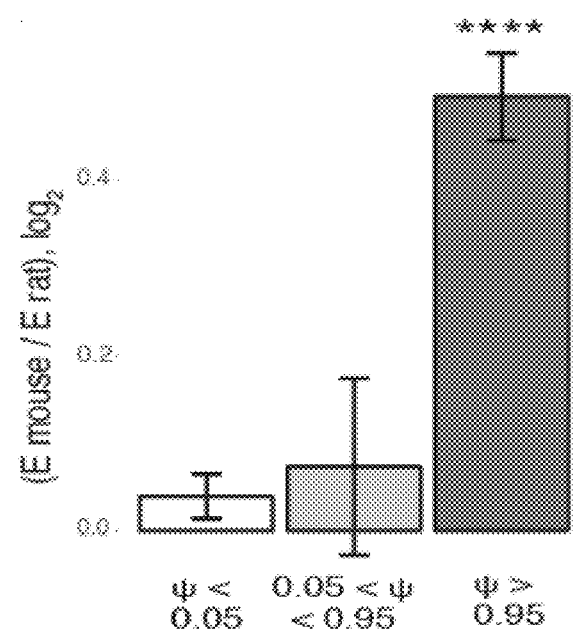
Figure 9A:
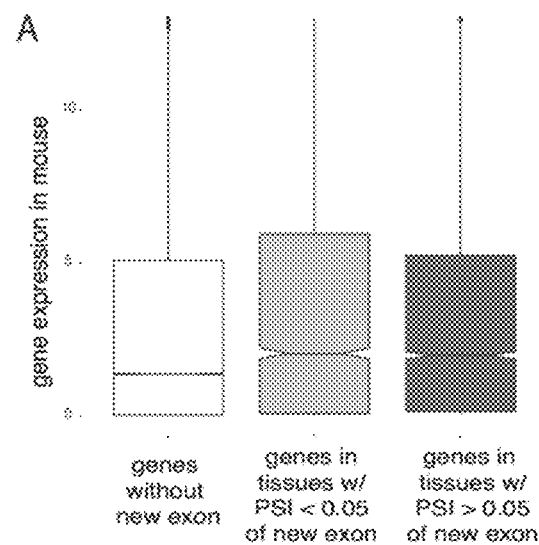
FIGS. 9A-9C include diagrams showing that splicing enhances transcription initiation.

Results i) Increased Exon Splicing is Associated with Increased Gene Expression and Alternative TSS Usage A comparative approach was used to explore potential connections between splicing and TSS usage, examining transcript patterns in orthologous genes of mouse and rat that differed by the presence/absence of an internal exon (i.e. a non-terminal exon flanked by introns). Previously, over one thousand such exons that were unique to the mouse transcriptome and not detected in RNA-seq data from diverse organs/tissues of other mammals including rat, macaque, cow, etc., and therefore likely arose recently in the mouse lineage were identified. Additionally, a similar number of exons that are unique to the rat were identified and leveraged within a similar number of genes (FIG. 8A). Most such evolutionarily new exons are located in 5' untranslated regions (UTRs) and are spliced in an alternative and tissue-specific fashion (Merkin et al., 2015). Comparing closely related species, it has been observed that genes with evolutionarily new internal exons tend to have increased gene expression, but only in those tissues where the new exons are included in mRNAs (FIG. 8A, FIG. 8B, FIG. 9A, and Table 1) (Merkin et al., 2015). This trend was stronger for genes with highly included exons-exons that were efficiently spliced—assessed by "percent spliced in" (PSI or y) values >0.95, indicating that more than 95% of mRNAs from the gene include the exon (FIG. 8C)—suggesting an association between the extent of exon splicing and level of gene expression and suggesting that the enhancement in gene expression depends on the inclusion levels of the new exon.

Figure 8D:
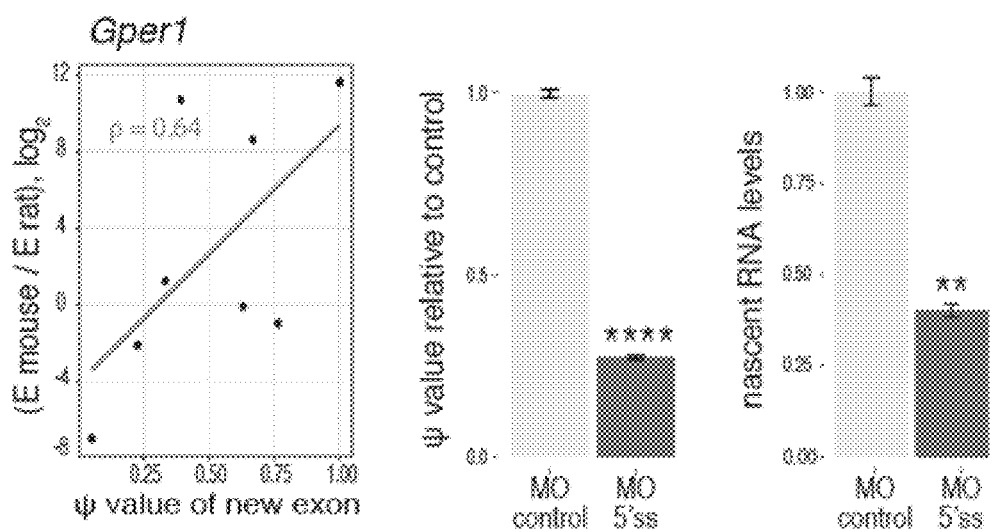
Figure 8E:
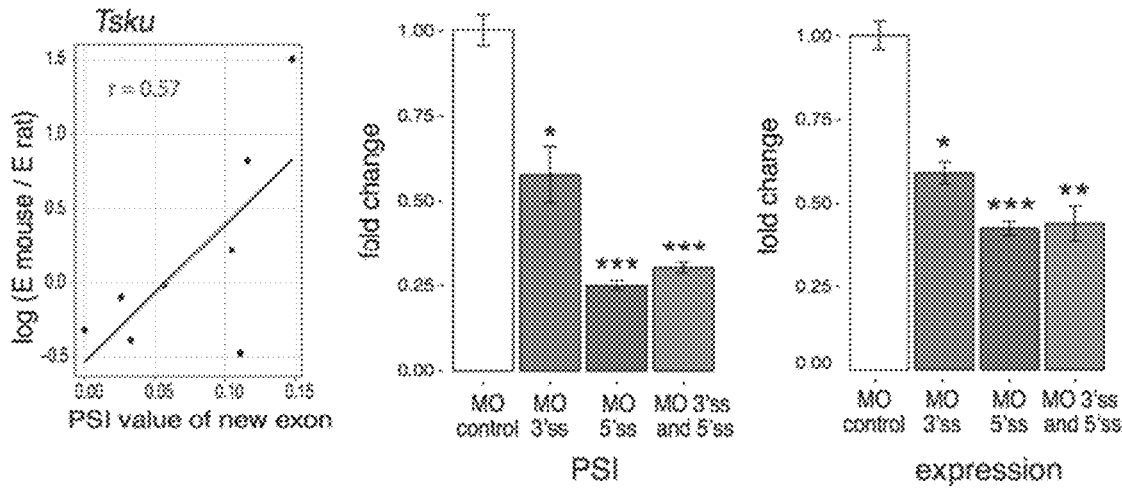
Figure 8F:
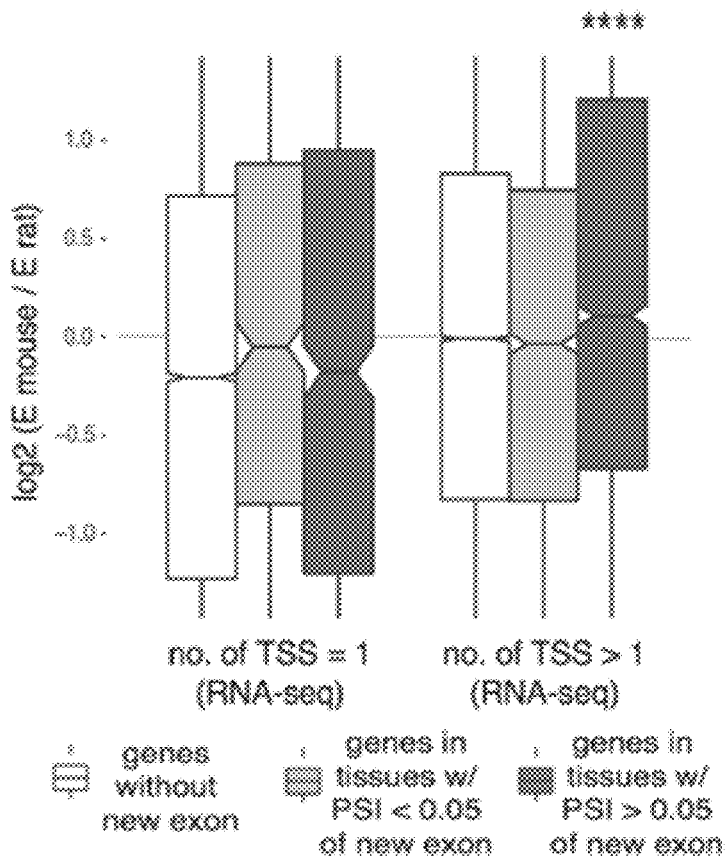
Figure 8G:
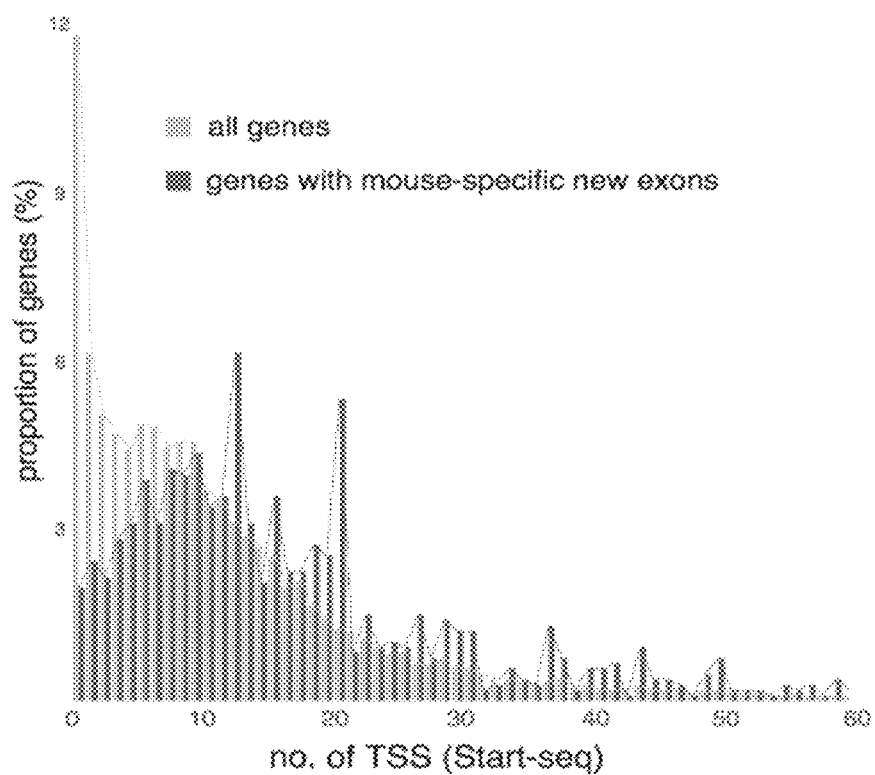
Figure 8H:
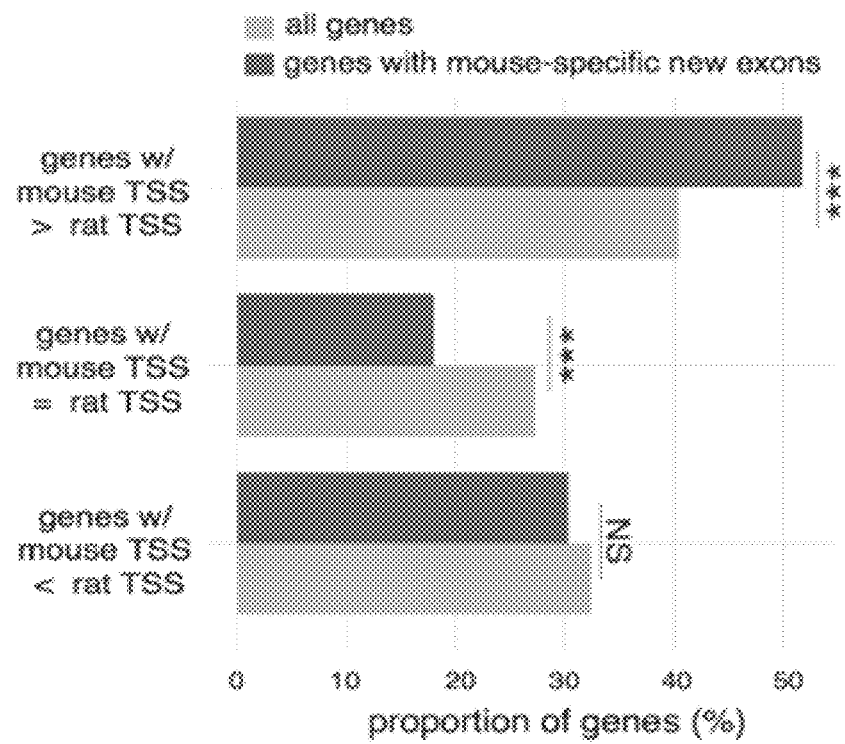
Figure 10A:
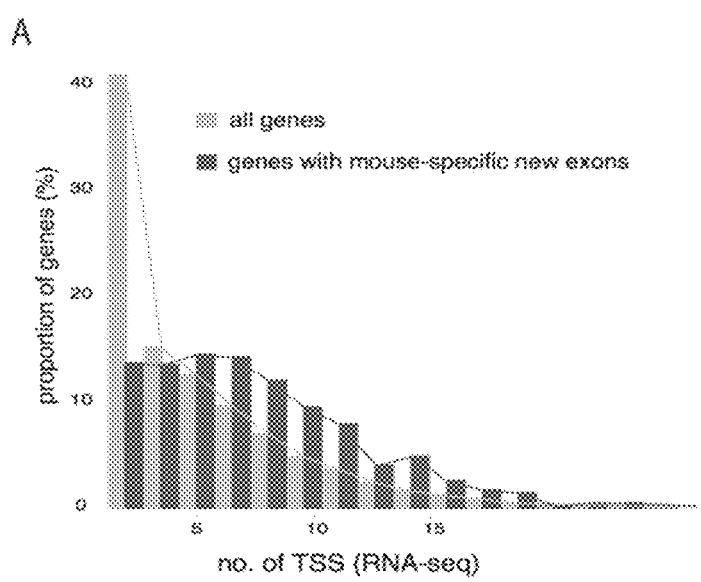
FIGS. 10A-10E include charts showing that genes with evolutionarily new exons are enriched in multiple TSSs.
Figure 10B:
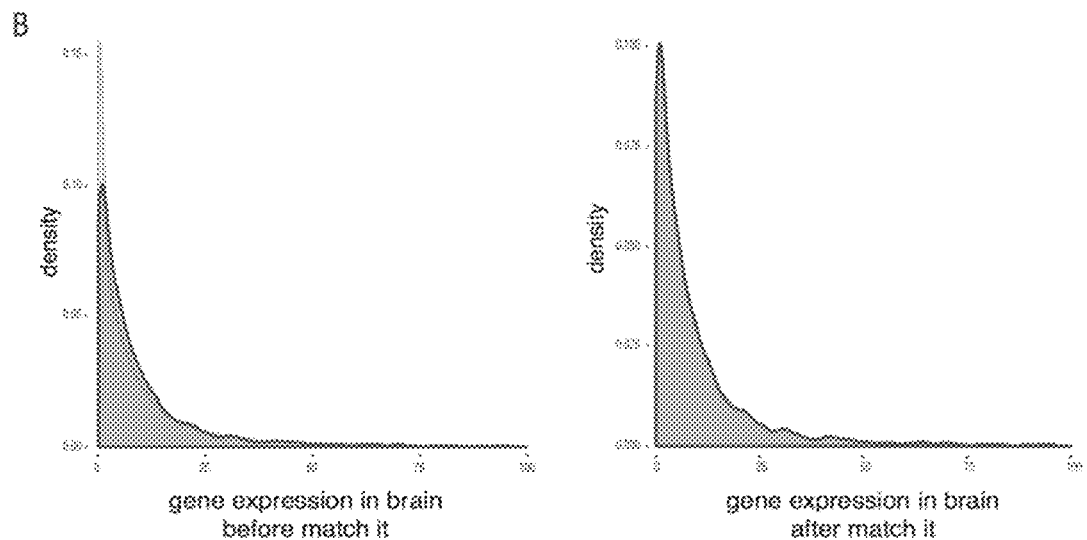
Figure 10C:
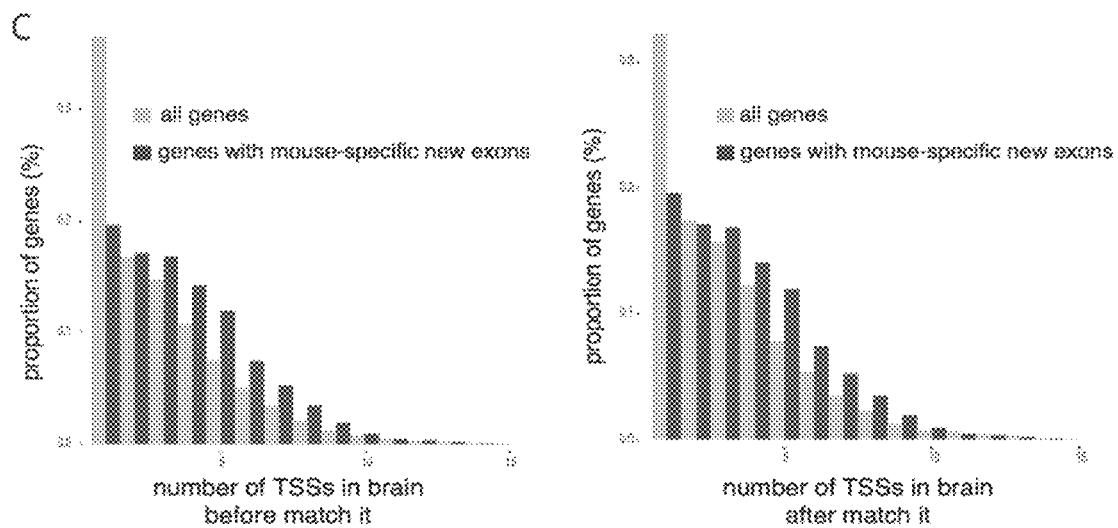
Figure 10D:
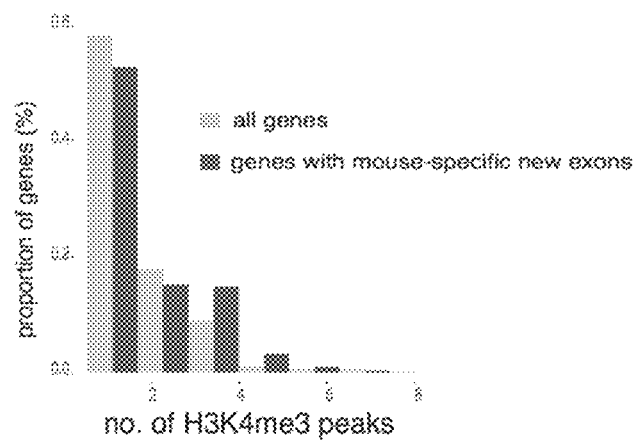
Figure 10E:
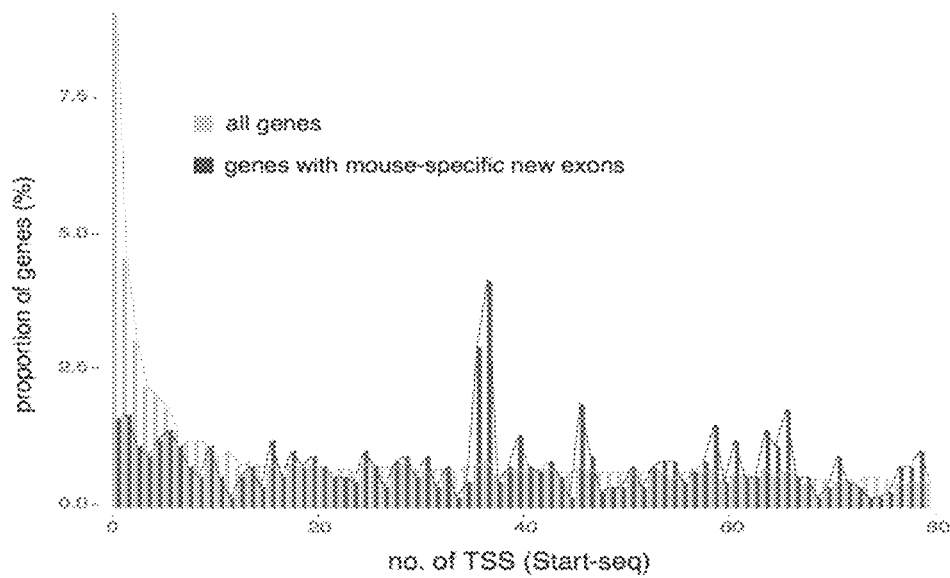
Figure 11A:
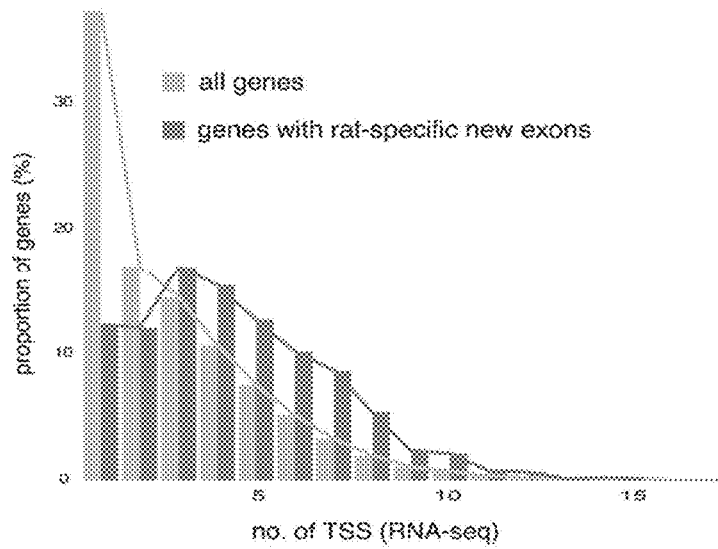
FIGS. 11A-11B include charts showing the evolutionary gain of internal exons and TSSs are associated across species.
Figure 11B:
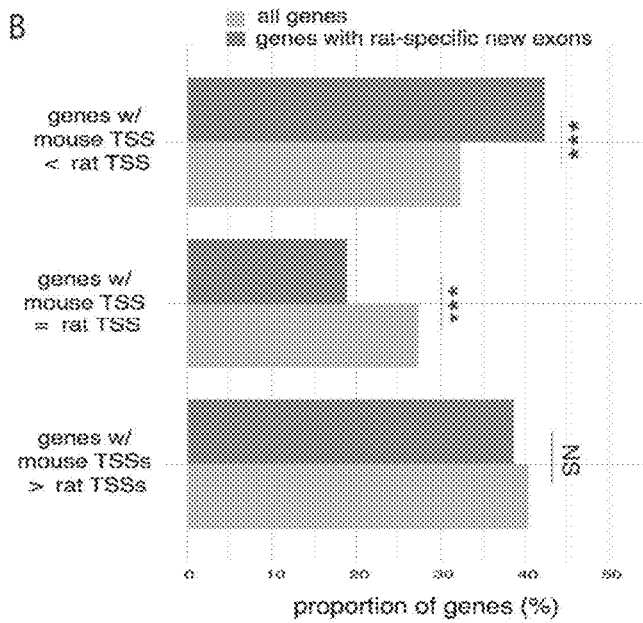

Herein, it was hypothesized that splicing could be modulating where transcription initiates. Grouping genes by their promoter structure, a positive association between inclusion of new exons and gene expression for genes with multiple TSSs was found, while this association was not observed for genes with only one TSS (FIG. 8F). Furthermore, the RNA-seq data (from (Merkin et al., 2012)) showed that genes with mouse-specific new exons were significantly more likely to have multiple TSSs compared to all expressed genes in mouse (FIGS. 10A-10C). It was confirmed that genes with new mouse-specific exons are more likely to have multiple TSSs, using other methods to define TSS locations, including H3K4me3 ChIP-seq peaks (Yu et al., 2015) and data from high-resolution sequencing of polymerase-associated RNA (Start-seq) (Scruggs et al., 2015) (FIG. 8G, FIGS. 10D-10E, Table 2). Genes with rat-specific new exons also had more TSSs per gene than rat genes overall (FIG. 11A). Furthermore, genes that gained new species-specific exons were more likely to have gained TSSs in the same species, suggesting that the evolutionary gain of an internal exon is connected to evolutionary gain of TSSs in a locus (FIG. 8H and FIG. 11B).

Figure 12A:
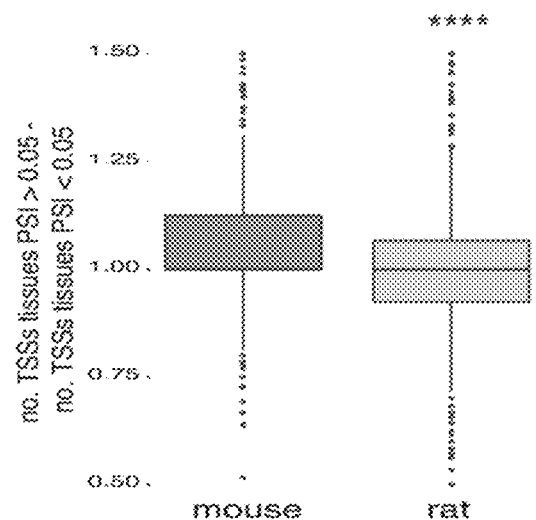
FIGS. 12A-12F include diagrams showing that splicing of new exons is associated with increased usage of multiple TSSs.
Figure 13A:
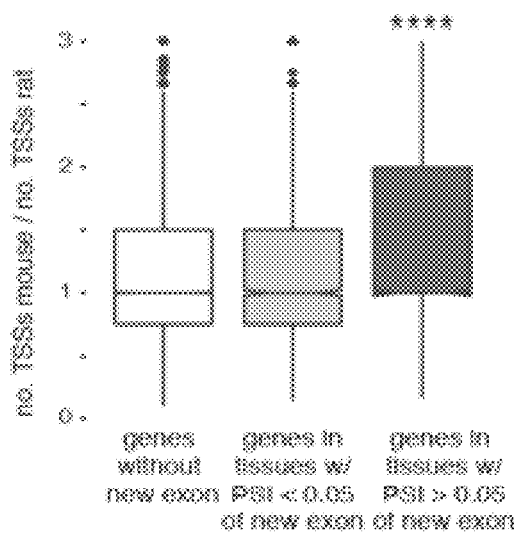
FIGS. 13A-13F include diagrams showing that Splicing of new exons is associated with usage of proximal and upstream TSS.

To investigate this connection further, the usage of new exons and TSSs used by a gene in different tissues was examined. It was observed that genes containing mouse-specific exons used more distinct TSSs than their rat orthologs (FIG. 12A), and that this association was specific to mouse tissues where the new exon was included with PSI>0.05, showing a connection between splicing and TSS use in different mammalian organs (FIG. 13A).

Figure 12B:
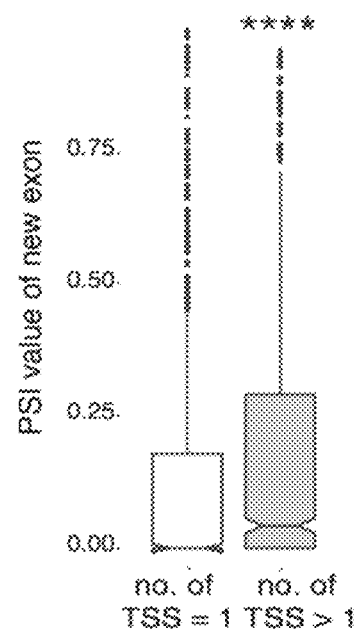
Figure 12C:
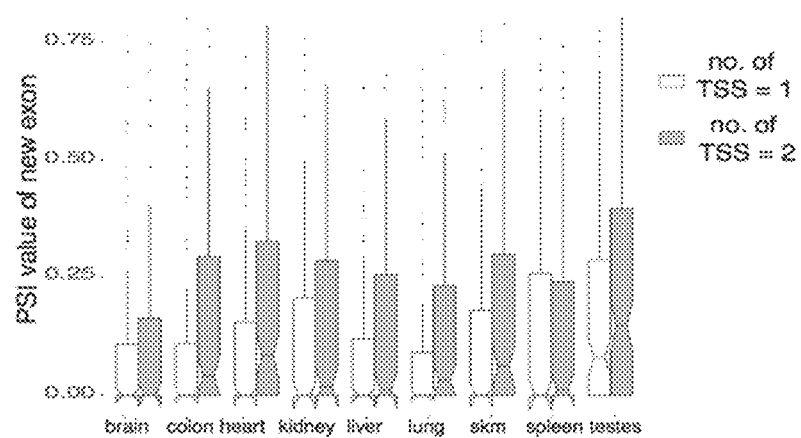
Figure 12F:
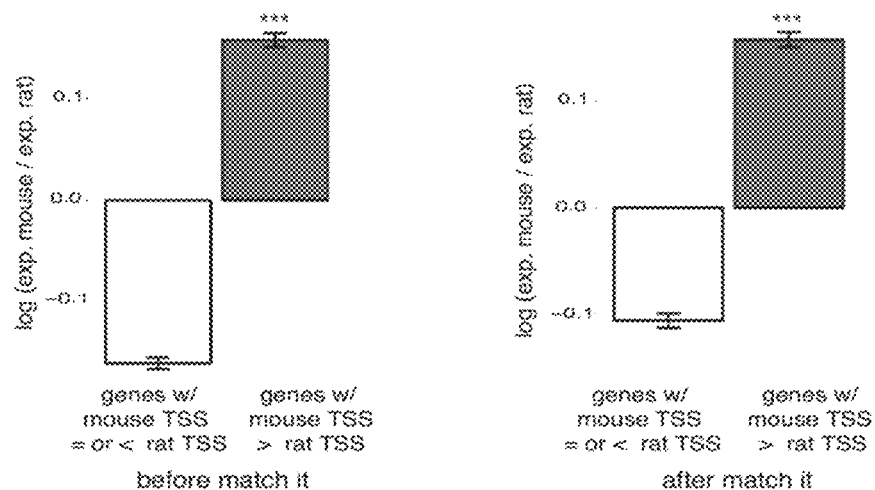
Figure 13B:
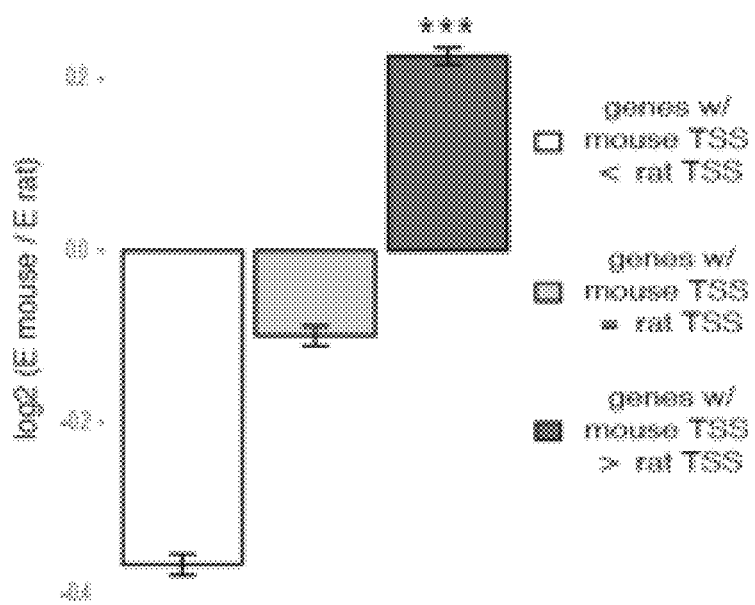

Higher PSI values for new exons in genes with multiple alternative TSSs relative to genes with a single TSS were also observed, with the largest difference being between genes with one and two TSSs (FIGS. 12B-12C). Furthermore, the increased gene expression levels in mouse relative to rat in genes with new mouse exons was restricted to those genes that gained TSSs in mouse (FIG. 13B and FIG. 12F). Together, these observations indicate that the usage of new TSSs and the splicing of new internal exons tend to occur in the same genes, tissues, and species, suggesting an intimate connection between splicing, increased gene expression and activation of new TSSs.

Figure 12D:
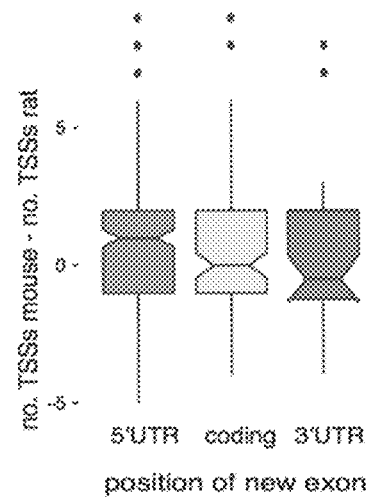
Figure 12E:
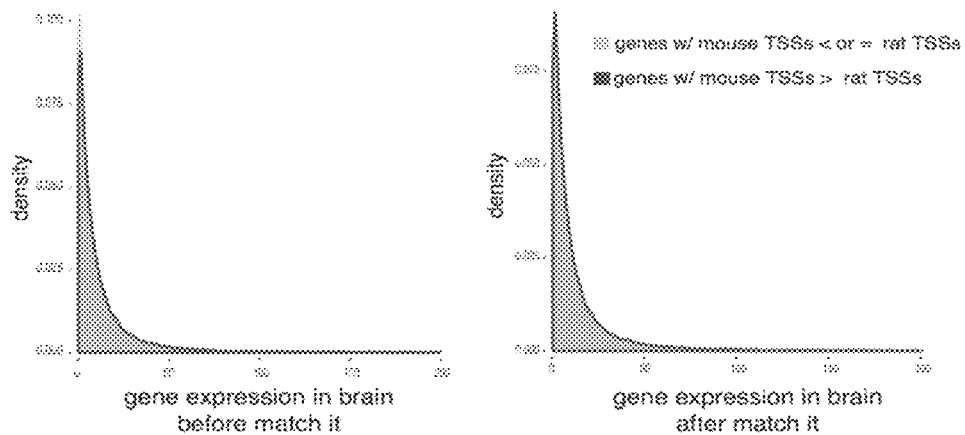
Figure 13C:
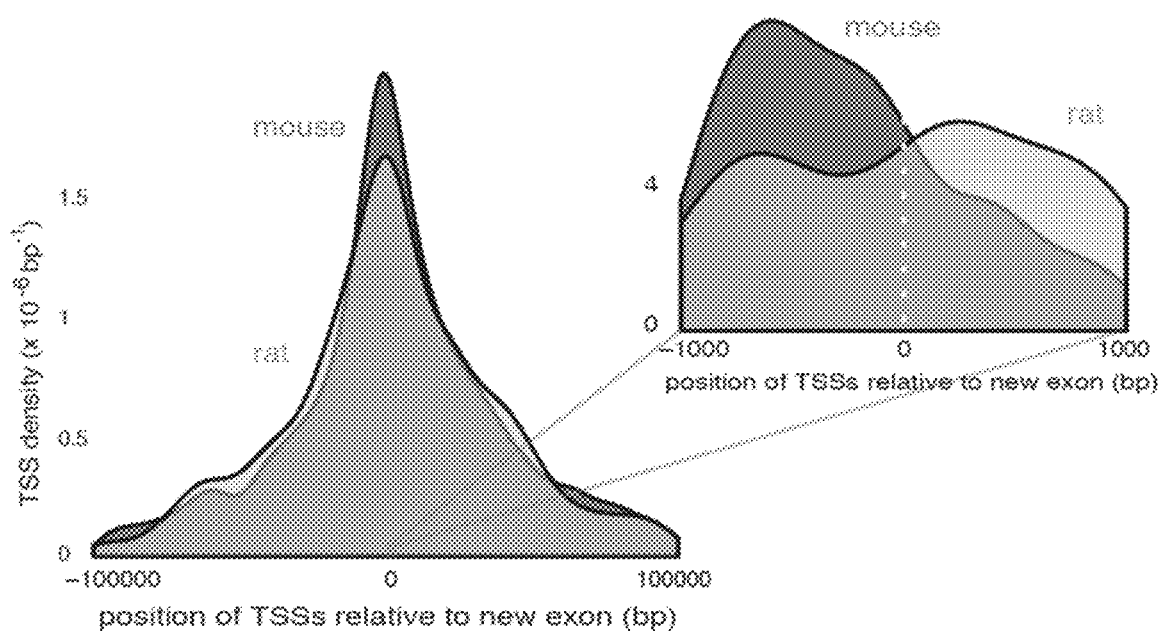
Figure 14A:
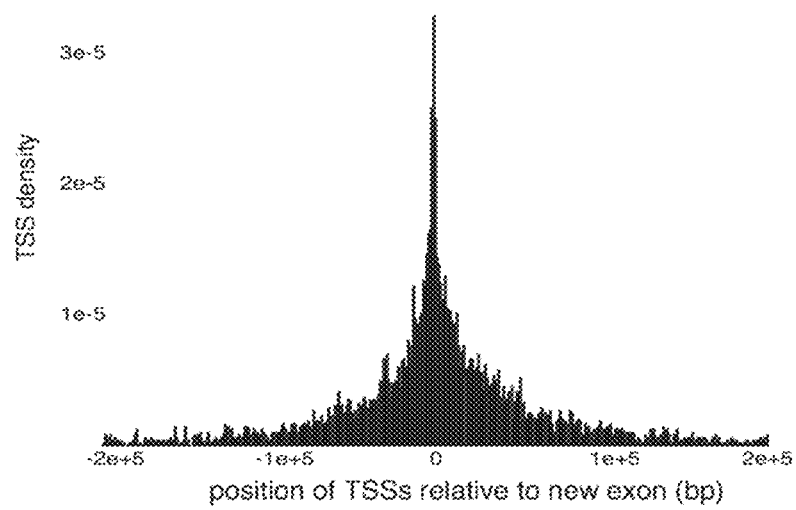
FIGS. 14A-14C include charts showing that TSSs preferentially arise proximal and upstream of new exons.
Figure 14B:
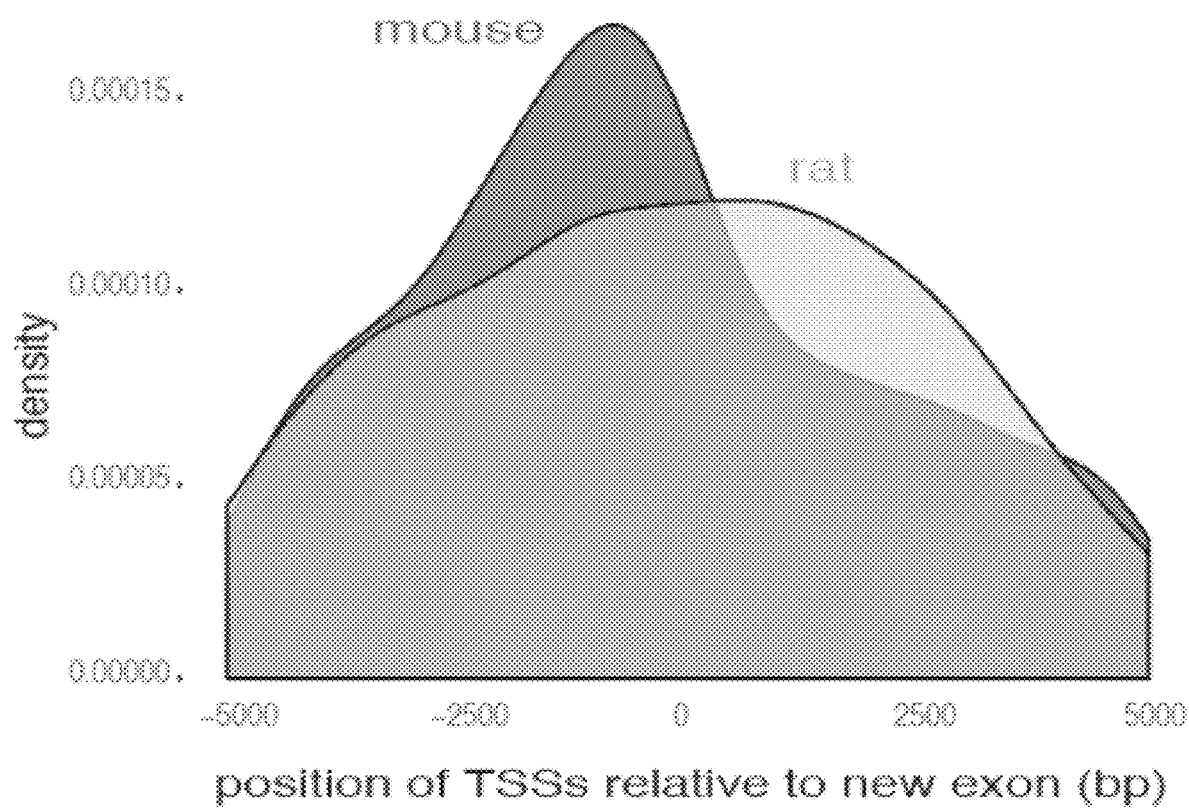

The results also showed a positional effect in which the increase in TSS counts per gene was associated predominantly with new exons located in 5' UTRs rather than those in 3' UTRs or coding regions was observed (FIG. 12D).

ii) Splicing of New Exons Enhances Gene Expression by Activation of Transcription at an Additional TSS and the Usage of TSSs and Splicing of Exons is Dependent on Relative Position As the results suggest that enhancement of gene expression is linked to splicing through the usage of multiple TSSs, it was hypothesized that genes that gain TSSs should have concomitant increases in gene expression. Indeed, the results showed significant increases in gene expression levels in mouse compared to rat, but only in genes that gained TSSs in mouse (FIG. 13B and FIGS. 12E-12F). Together, these data suggest that the splicing of new exons enhances gene expression by activating transcription at additional TSS. To establish the relative position of TSSs, the location of all TSSs used in mouse in genes with mouse-specific new exons relative to the start coordinate of the new exon was analyzed (FIG. 14A). To analyze the positional changes of newly-associated TSSs between species, the distribution of TSSs in mouse was compared to the distribution of TSSs in rat, aligning the homologous coordinate of the mouse-specific exon in rat as zero. The distribution of the locations of all mouse TSSs relative to the locations of mouse-specific new exons was examined (FIG. 14A), and compared to the distribution of rat TSSs relative to sites homologous to the mouse-specific exons. This comparison showed an enrichment of TSSs in mouse within one or two kilobases (kb) upstream of new exons. TSSs in mouse become more centered around the new exons compared to rat and, closer to the position of new exons, TSSs in mouse peak proximal and upstream of new exons within a window of 1 kb (FIG. 13C and FIG. 14B). Thus, evolutionary gain of new internal exons was specifically associated with gain of proximal, upstream TSSs.

Figure 13D:
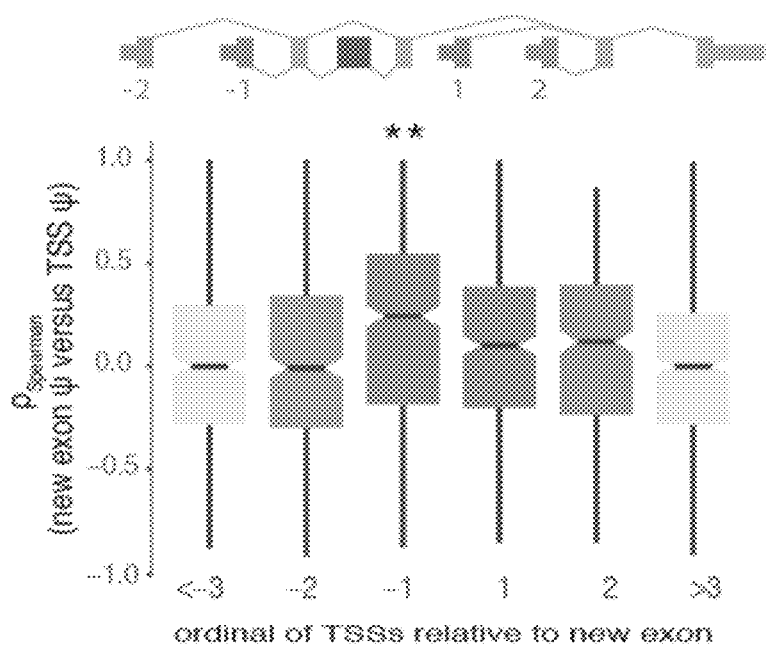
Figure 13E:
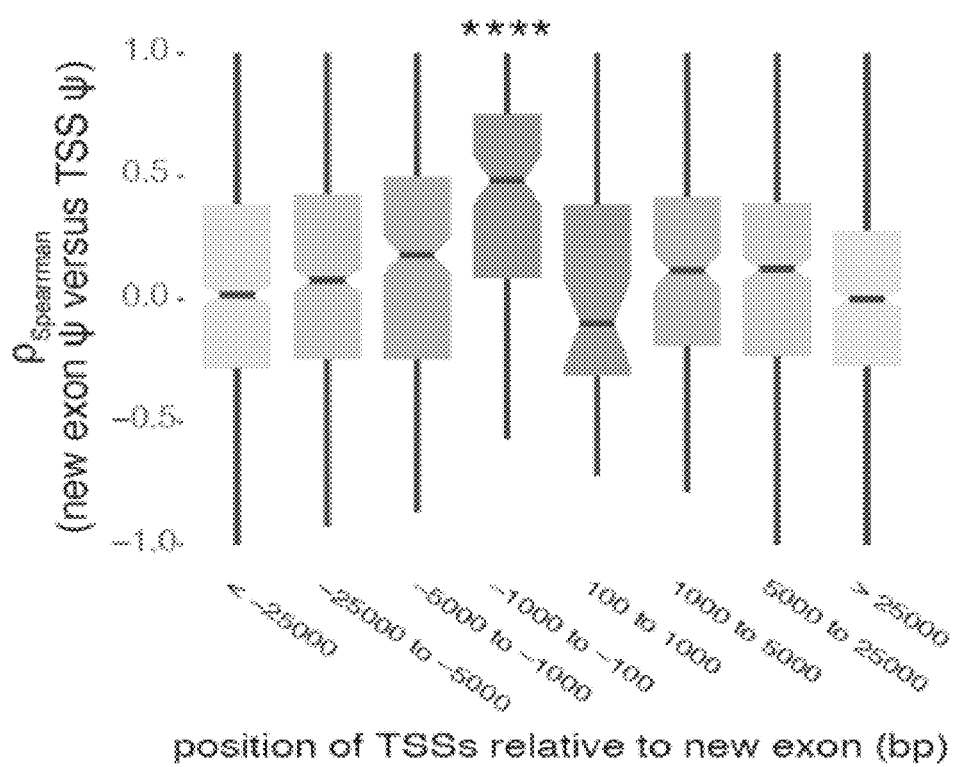
Figure 13F:
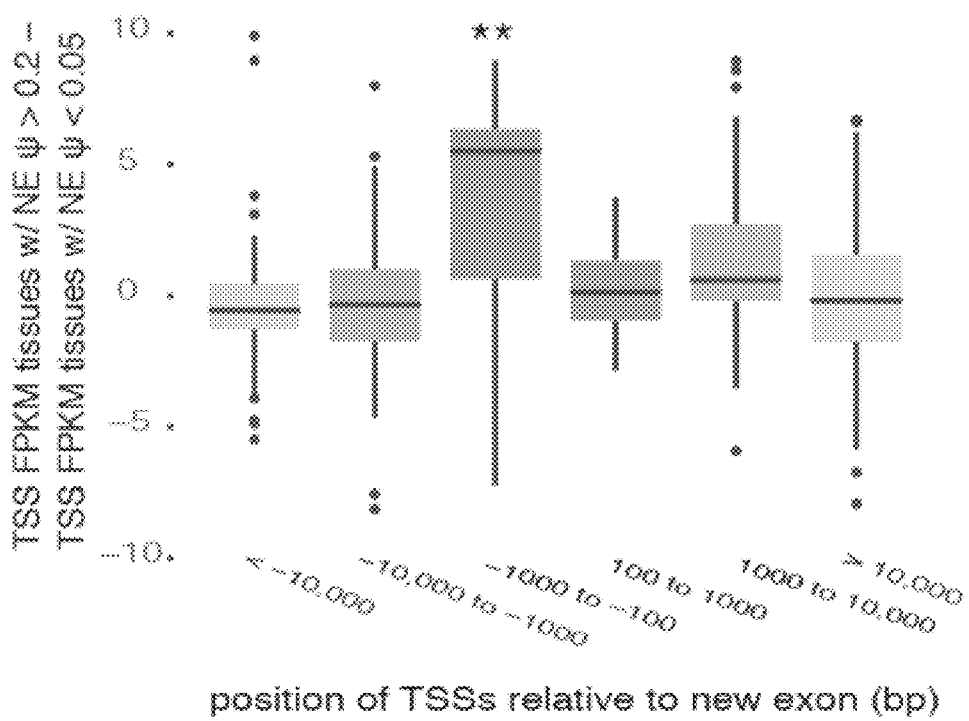
Figure 14C:
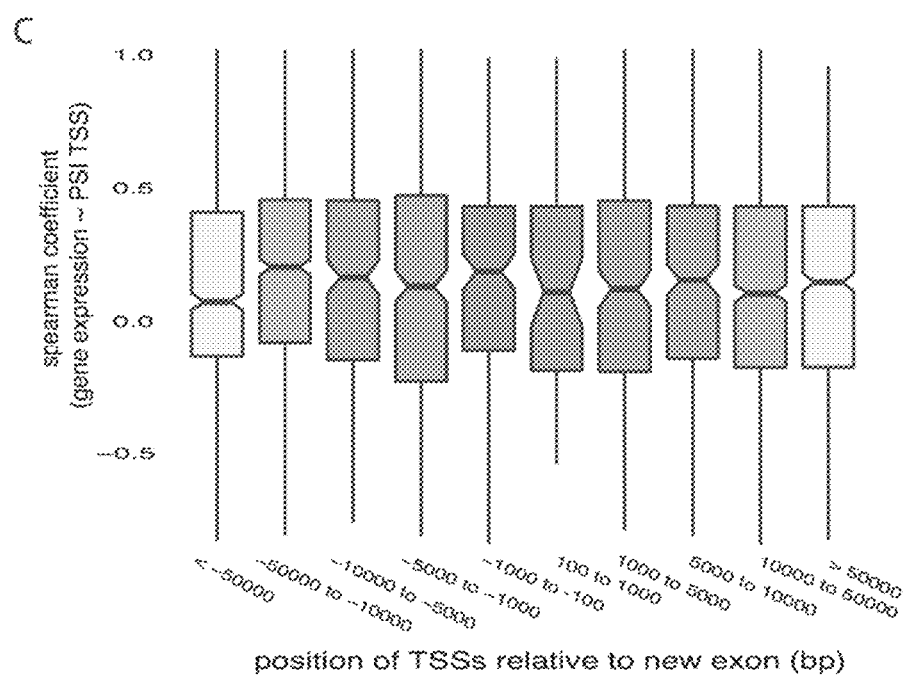

It was then determined if the correlation across tissues between the usage of a particular TSS and the PSI value of new exons changes depending on their relative position. The relationship between splicing levels and usage of alternative TSS within the same gene was examined. Considering relative TSS use ("TSS PSI", representing the fraction of transcripts from a gene that derive from a given TSS) it was found that use of the most proximal upstream TSS (designated TSS-1) was positively correlated with new exon inclusion, especially for TSSs located within about 1 kb upstream of the new exon (FIG. 13E and FIG. 13D). Furthermore, absolute expression of transcripts from nearby TSSs increased (FIG. 14C) specifically in tissues where new exons were included at moderate or high levels (FIG. 13F). These results suggest a positive influence of splicing on nearby transcription (or possibly vice versa). These results suggest that proximal and upstream new TSSs are associated with the inclusion of new exons either because splicing of new exons in some way activates transcription from proximal TSSs or because use of proximal TSSs favors the inclusion of these exons.

iii) Manipulation of Exon Splicing Impacts Upstream Transcription Initiation

Figure 8I:
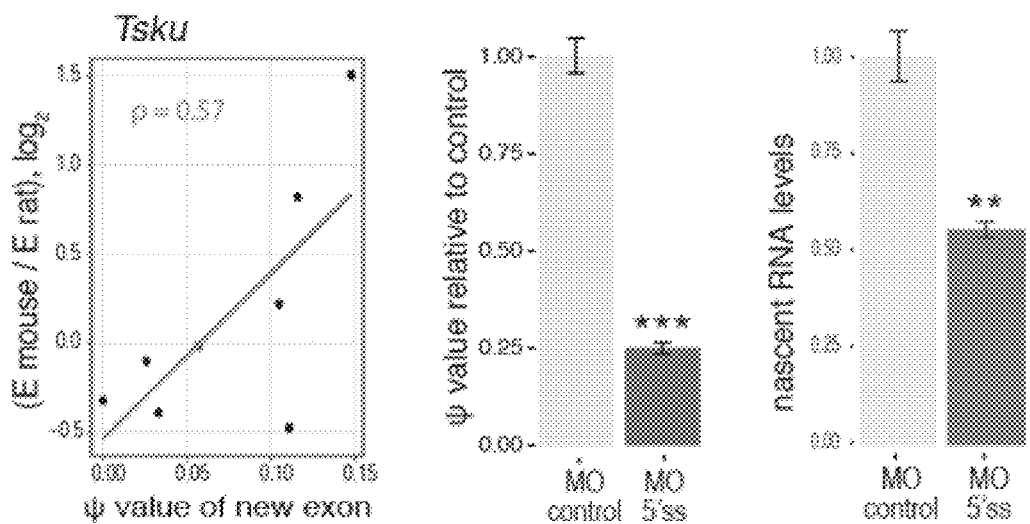
Figure 9B:
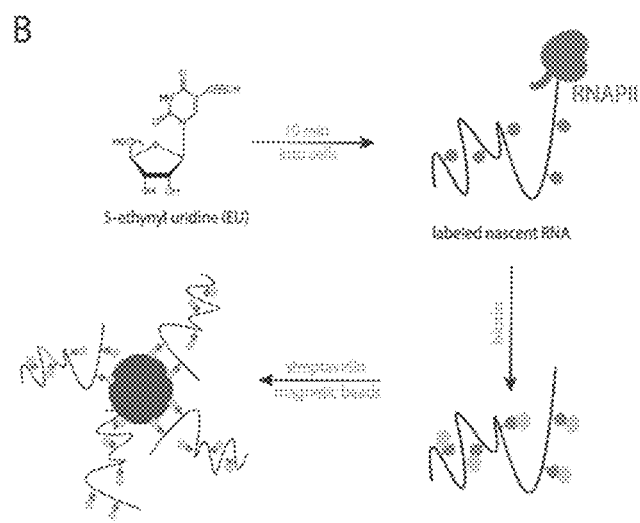
Figure 9C:
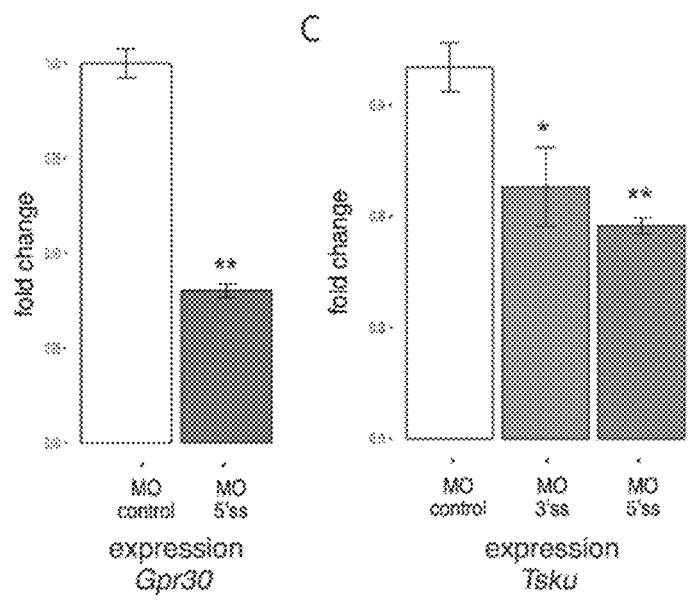

To directly test whether splicing impacts nearby transcription and inhibiting new exon inclusion leads to a decrease in gene expression, two candidate mouse genes, Gper1 (G protein-coupled estrogen receptor 1; also referred to as GPR30 (G protein-coupled receptor 30)), and Tsku (Tsukushi, small leucine rich proteoglycan) were chosen. These genes both have widespread, moderate expression and contain a mouse-specific 5' UTR internal exon whose splicing is positively correlated with the expression of the gene across mouse tissues (Spearman p=0.64 and 0.57, respectively; FIG. 9C and FIG. 8I left panels). When cultured mouse fibroblasts were treated with morpholino antisense oligonucleotides (MO) targeting splice sites of the new exons, exon inclusion decreased by about 4-fold in both Gper1 (FIG. 8D) and Tsku (FIG. 8I). Moreover, gene expression levels of these two genes were depressed to a similar extent (FIG. 9B), consistent with a positive effect of exon inclusion on gene expression. Gene expression levels and PSI values of new exons decreased to a similar extent in the two candidate genes when cells were treated with morpholino oligonucleotides (MO) that blocked the recognition of the new exons' splice sites (FIGS. 8D-8E), demonstrating a role of splicing in enhancement of gene expression. Since steady-state mRNA levels are determined by synthesis and degradation, metabolically labeled nascent RNA was analyzed to confirm that the effect is occurring at the transcriptional level (FIGS. 9B-9C). Similar levels of repression when assaying metabolically labeled nascent RNA (FIG. 9B) were observed as with total mRNA, indicating that the effect is primarily at the level of transcription rather than mRNA stability (FIG. 9C and FIG. 8I). These results support an enhancing effect of splicing on transcription initiation and support the idea that exon splicing positively impacts nearby transcription.

a) Effects on Nascent and Steady State RNA Levels

Figure 15A:
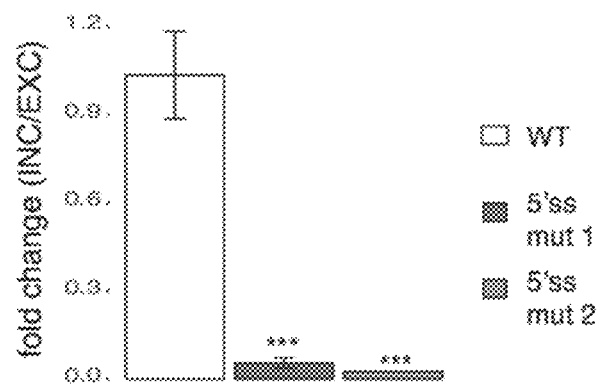
FIGS. 15A-15C include diagrams showing that splicing perturbations of an exon regulate the usage of alternative TSSs.
Figure 15B:
Figure 15B:
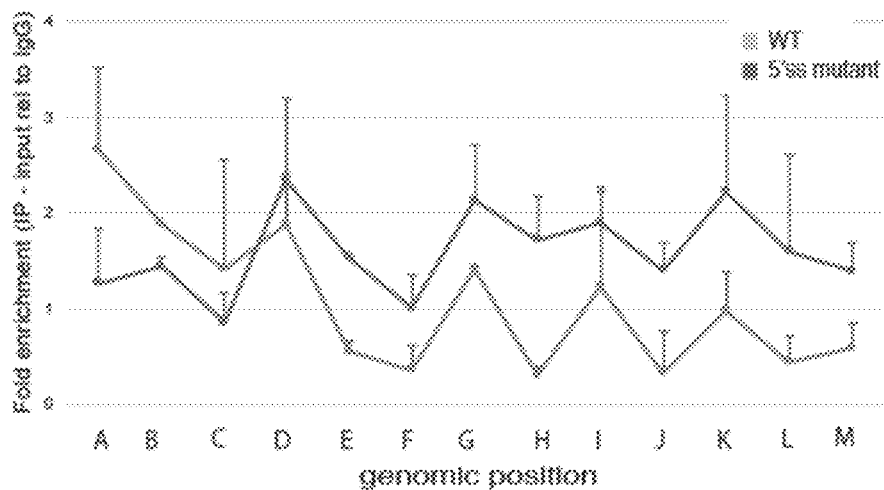
Figure 16A:
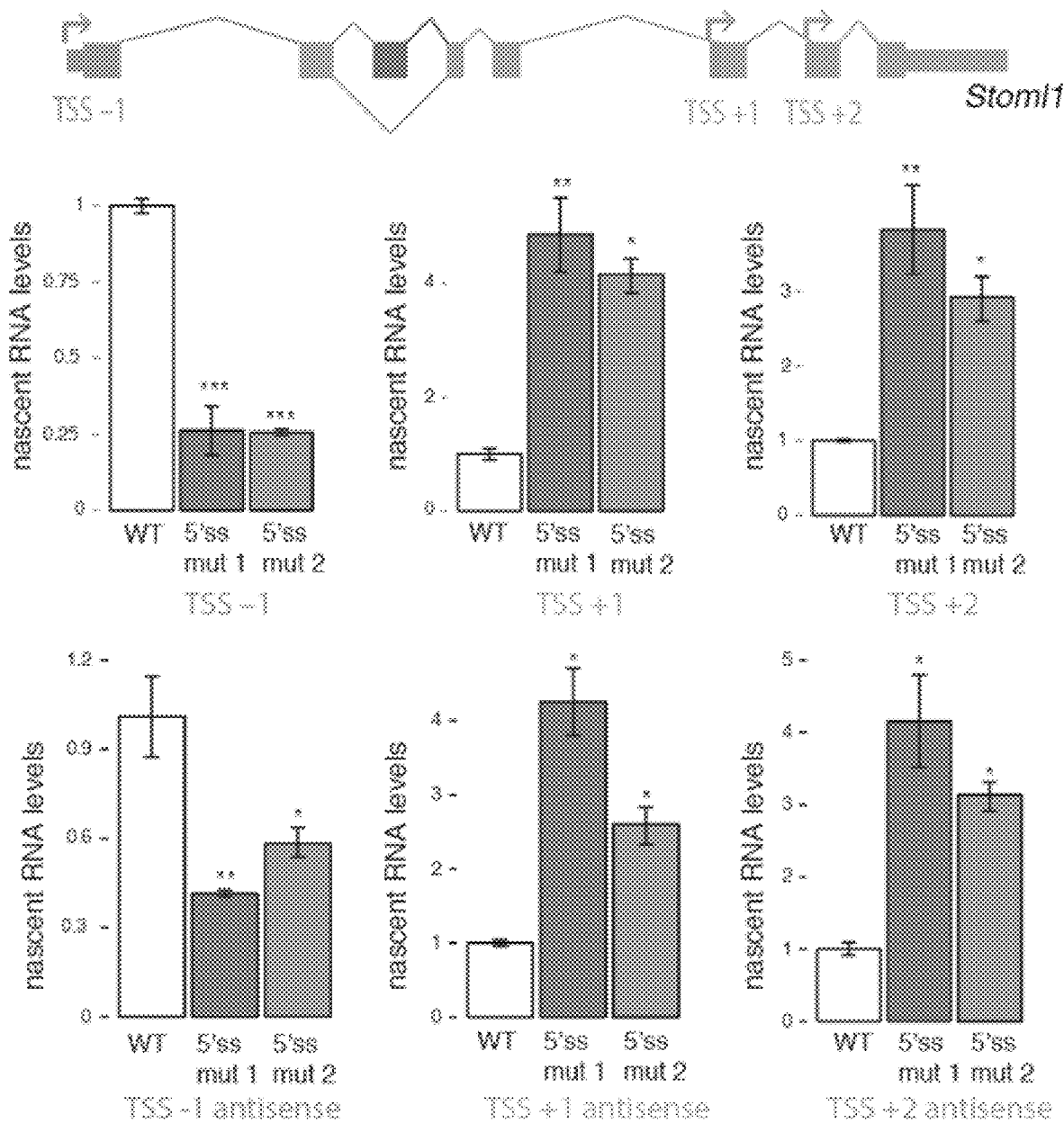
FIGS. 16A-16G include diagrams showing that genetic manipulation of the splicing of an exon alters upstream transcription.
Figure 16B:
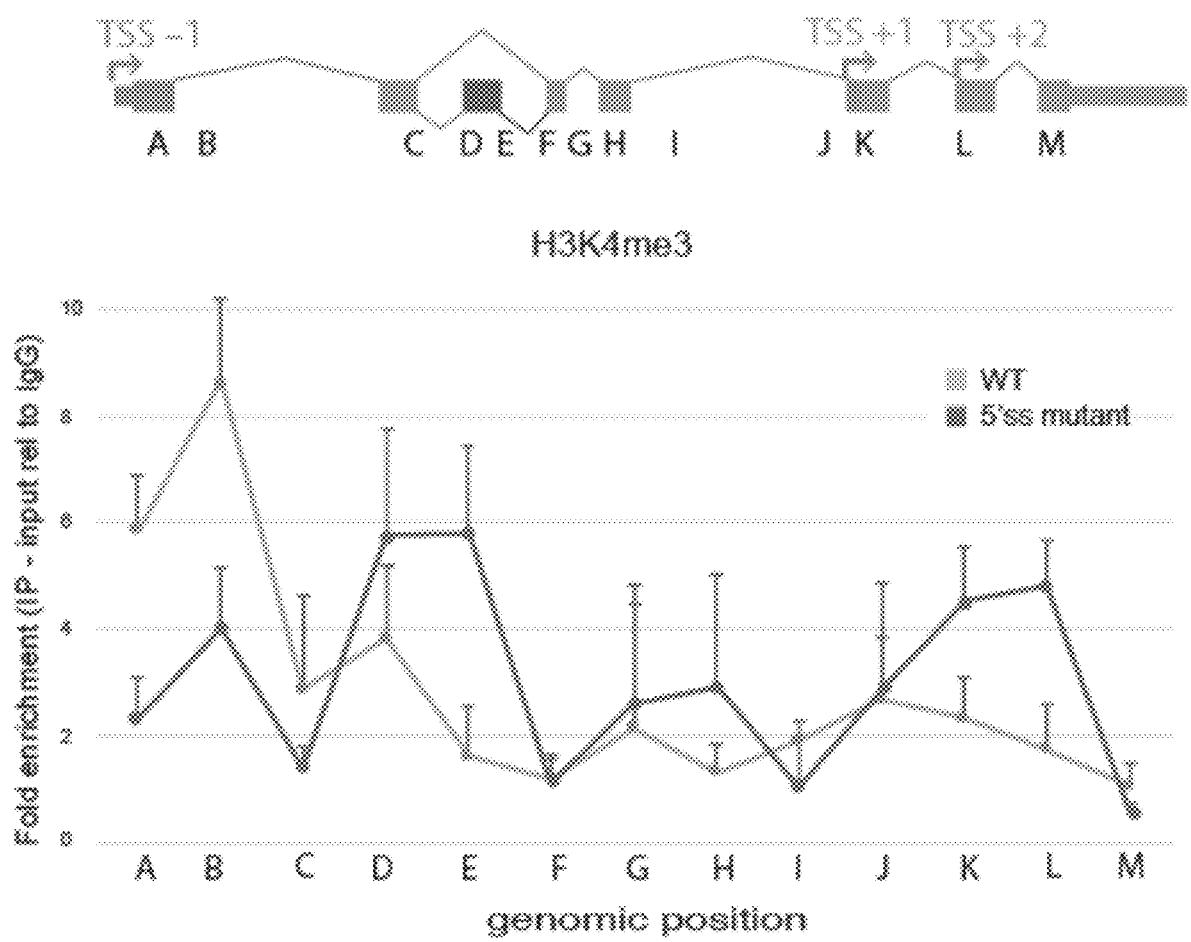

Effects on transcription initiation should be reflected in nascent RNA, while effects on RNA stability would only be visible in steady state mRNA. In the Tsku gene, nascent RNA levels were reduced to a similar extent as steady state mRNA (FIG. 15A, FIG. 19C, FIGS. 19E-19F, and FIG. 24A), in both sense and antisense orientations. For other genes studied here, Stoml1 and Gper1, similar effects on nascent RNA in sense and antisense directions were observed (FIG. 13F, FIG. 15A, FIG. 17A, and FIGS. 17C-17E). Furthermore, the model invoking inhibition of PCPA involves U1 snRNP binding at a 5' splice site, but increased gene expression from creation of a 3' splice site was observed. Thus, observations are consistent with splicing-dependent regulation of transcription initiation but not with models involving PCPA.

iv) The Inclusion of New Exons Enhances Transcription from the Upstream Promoter in Both Directions To test the directionality of this effect, determine how splicing of new exons impacts the use of different TSSs, and investigate whether the splicing of new exons can regulate the usage of multiple TSSs and specifically promote upstream TSSs, CRISPR-Cas cell lines were generated with mutations that abolished the inclusion of the new exon in Stoml1 gene (FIG. 15A). The mouse Stoml1 (Stomatin Like 1) gene was chosen, because it has three alternative TSSs as well as a new exon, all of which are used in mouse fibroblasts (FIG. 15B). Notably, the three alternative TSSs of the Stoml1 gene responded differently to inhibition of splicing of the new exon. Using CRISPR/Cas9 mutagenesis to generate cell lines with mutations abolishing the inclusion of a new exon, it was observed that the three alternative TSSs of the gene responded differently to inhibition of splicing of the new exon. The upstream—1 TSS was down-regulated by 4-fold, while downstream +1 and +2 TSSs were up-regulated to a similar extent in the mutant cell lines as measured by qPCR of nascent RNA (FIG. 16A). Effects on antisense transcription in these mutant cell lines mirrored those observed for sense transcription (FIG. 16A), suggesting that inclusion of the new exon enhances transcription from the upstream promoter in both directions. This pattern is distinct from a report of intron-mediated enhancement in which sense-oriented introns specifically inhibited antisense transcription (Agarwal and Ansari, 2016), but is consistent with reported impacts on transcription initiation resulting from changes in the position of an intron in a reporter gene (Gallegos and Rose, 2017). The increase in downstream promoter activity was not observed in other genes studied and may reflect some sort of locus-specific (e.g., homeostatic) regulation of Stoml1 expression. Levels of H3K4me3 and RNAPII decreased in the upstream TSS and increased in the downstream TSSs in the mutant cell lines, consistent with the observed effects on nascent transcript production (FIGS. 16B and 15B).

v) Exon-Mediated Activation of Transcription Starts Impacts Transcription

Figure 15C:
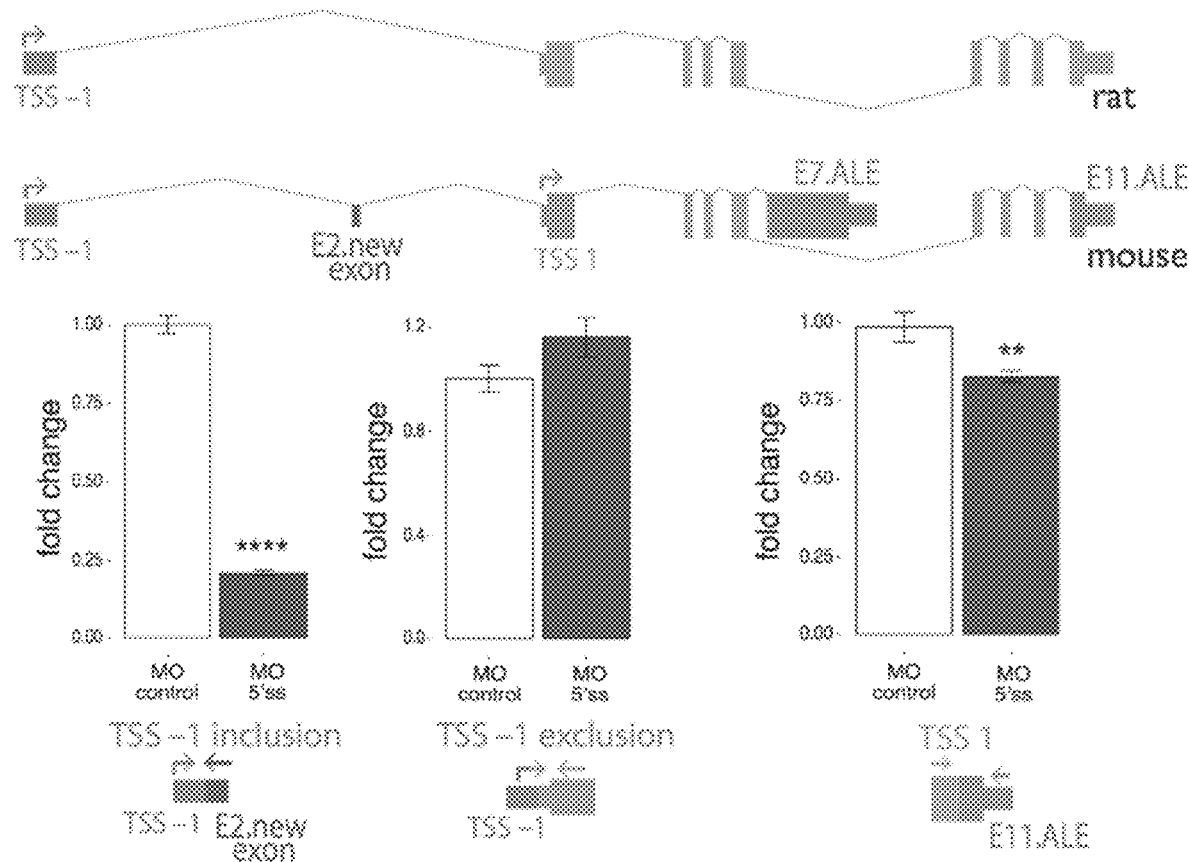
Figure 16C:
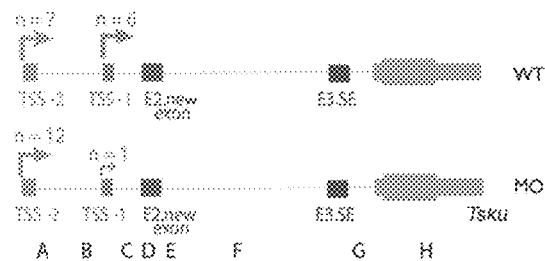
Figure 16D:
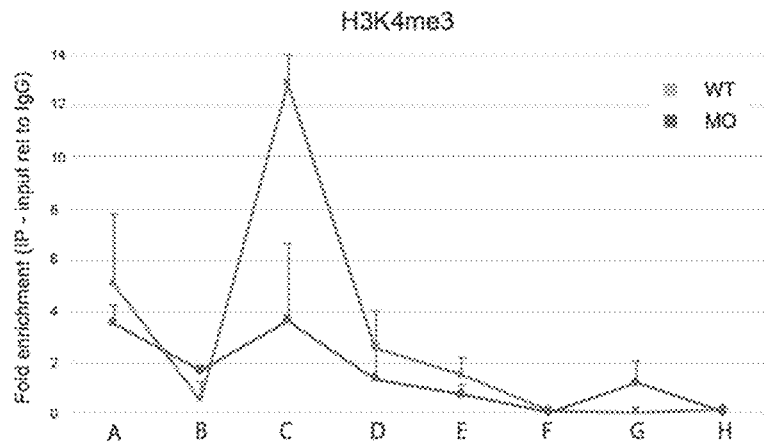
Figure 16E:
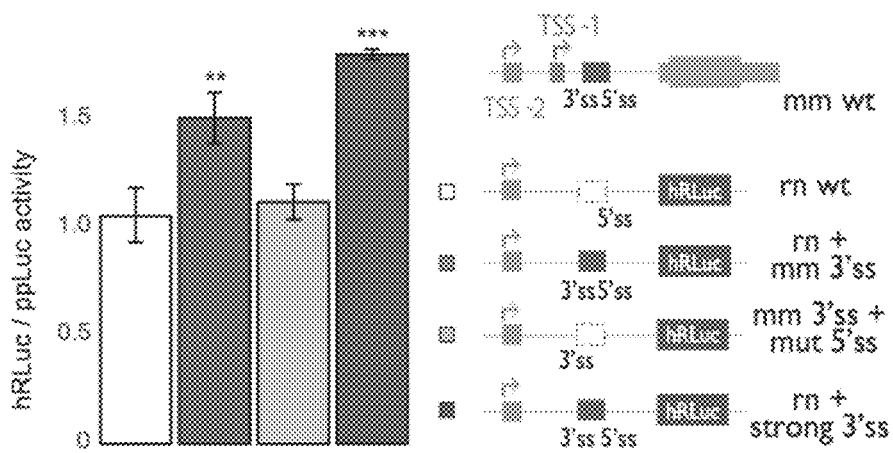
Figure 16F:
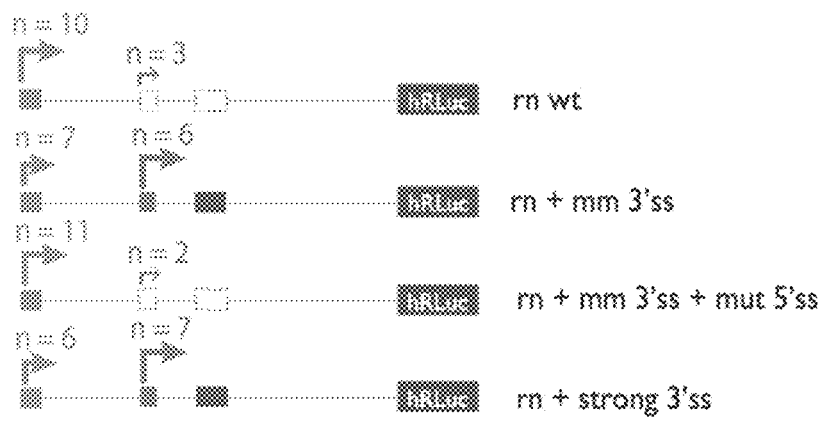
Figure 17A:
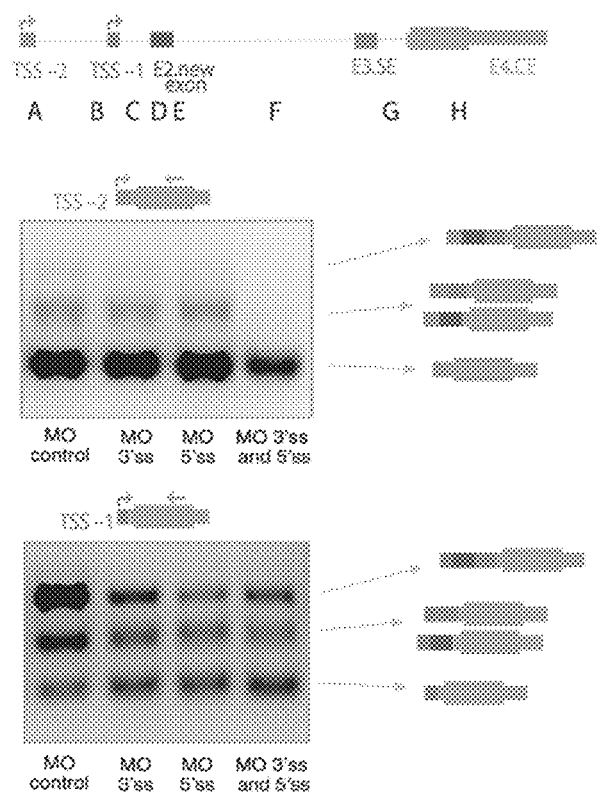
FIGS. 17A-17E include diagrams showing that splicing of new exons affects transcription from upstream and proximal TSSs.
Figure 17B:
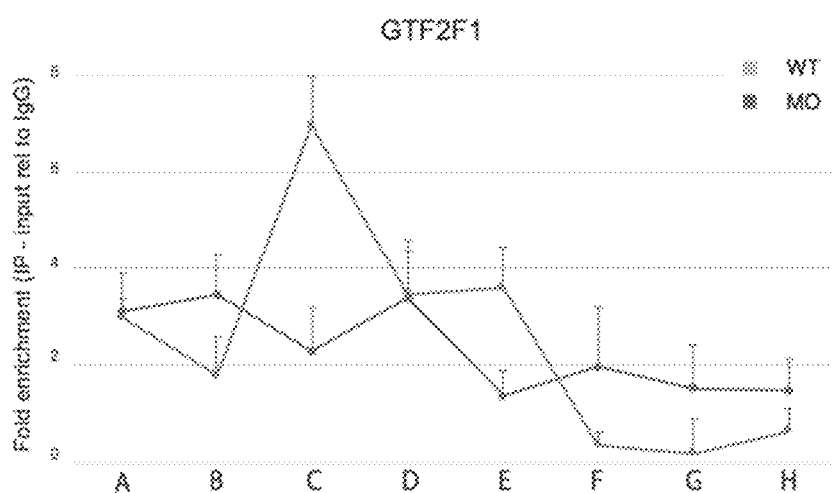
Figure 17C:
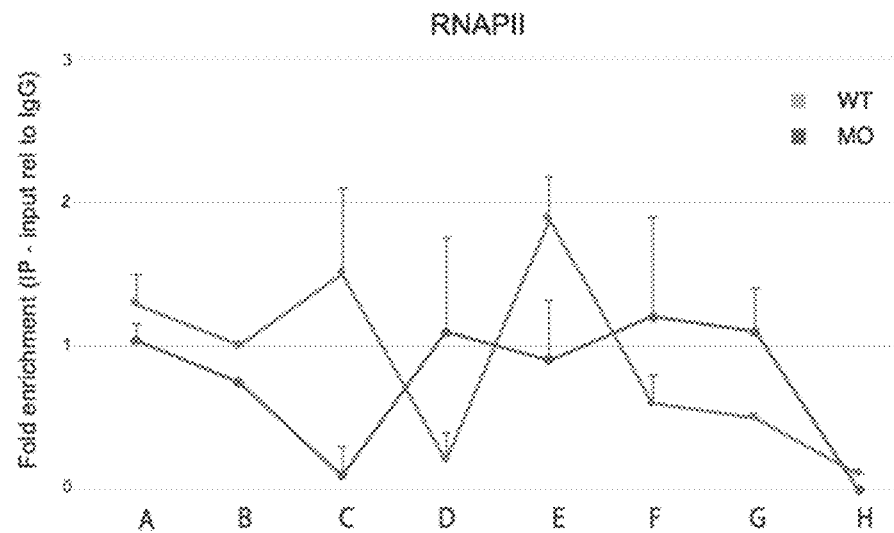
Figure 17D:
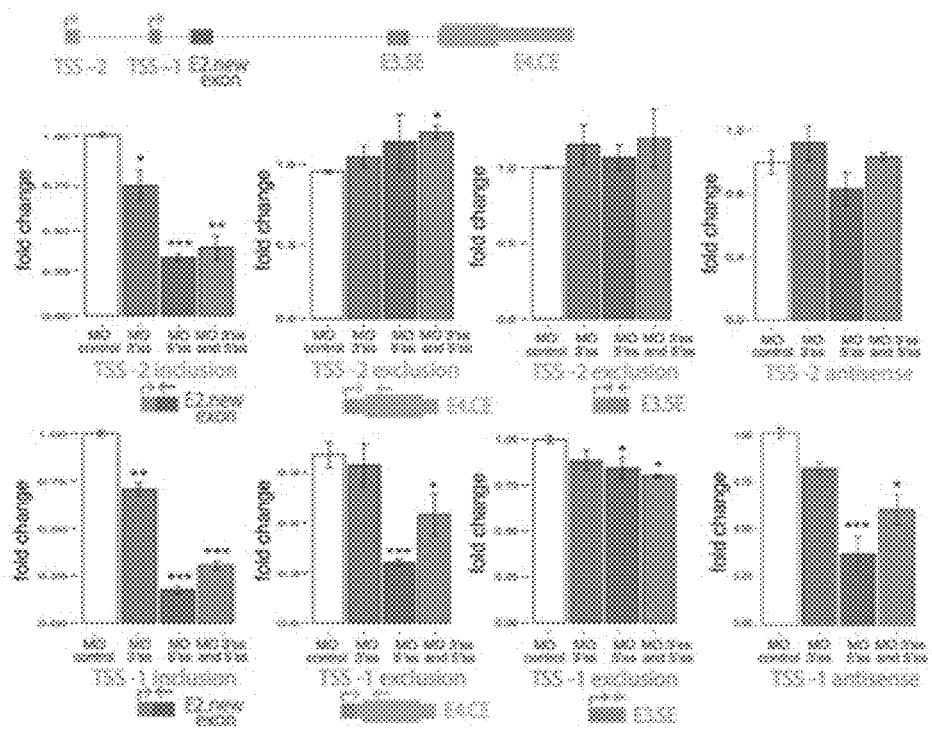
Figure 17E:
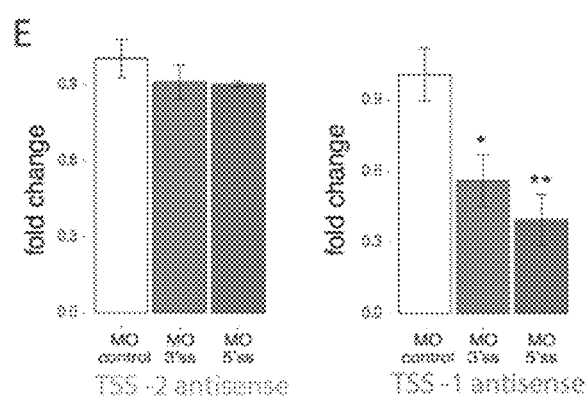
Figure 18B:
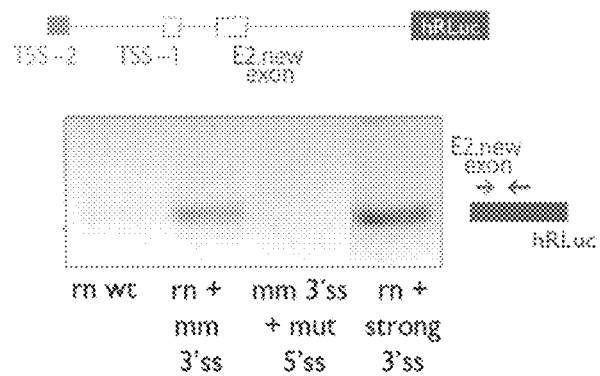
Figure 18C:
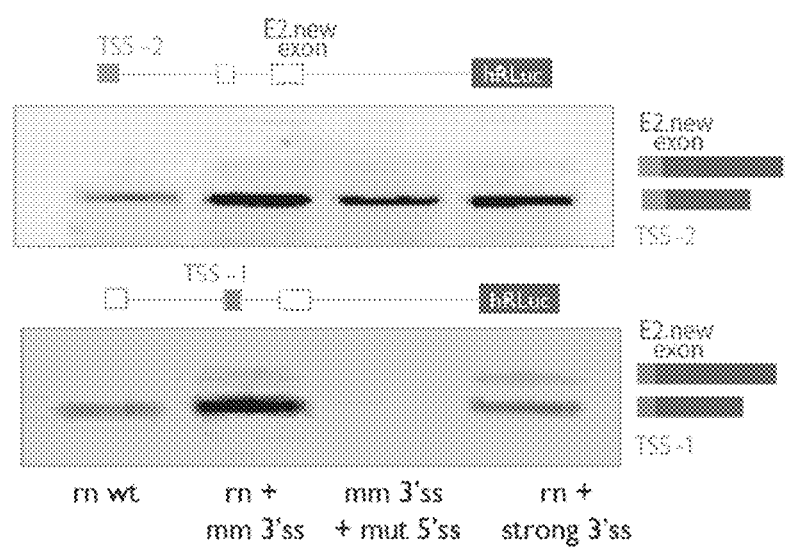
Figure 23A:
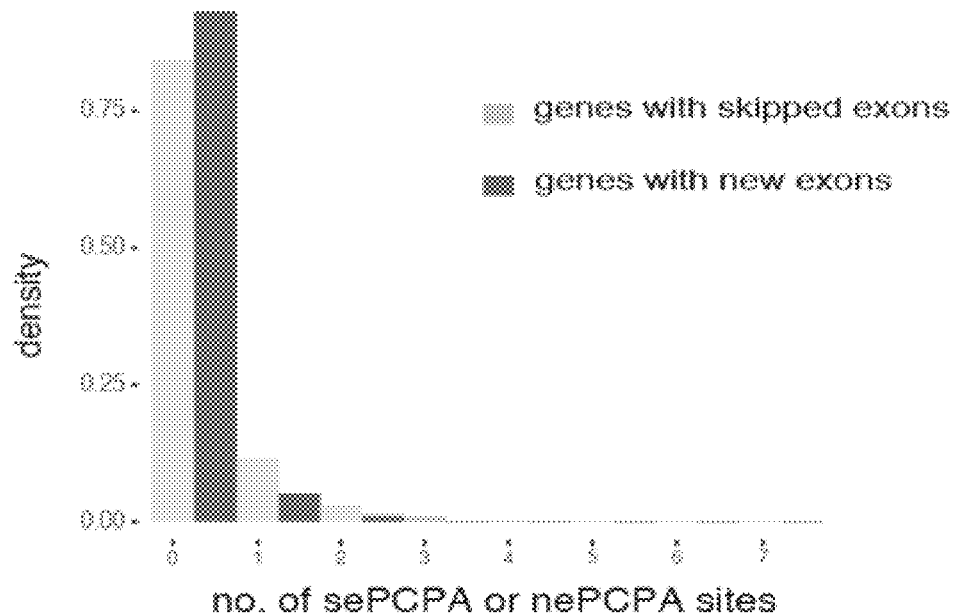
FIGS. 23A-23D includes diagrams showing that manipulation of exon splicing impacts upstream transcription initiation.
Figure 23B:
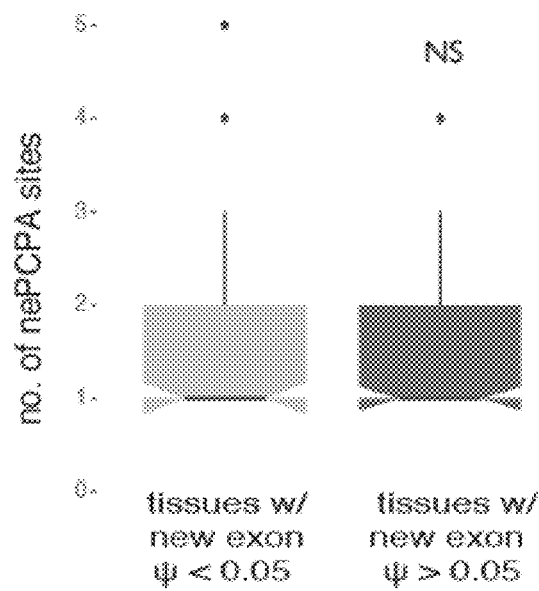
Figure 23C:
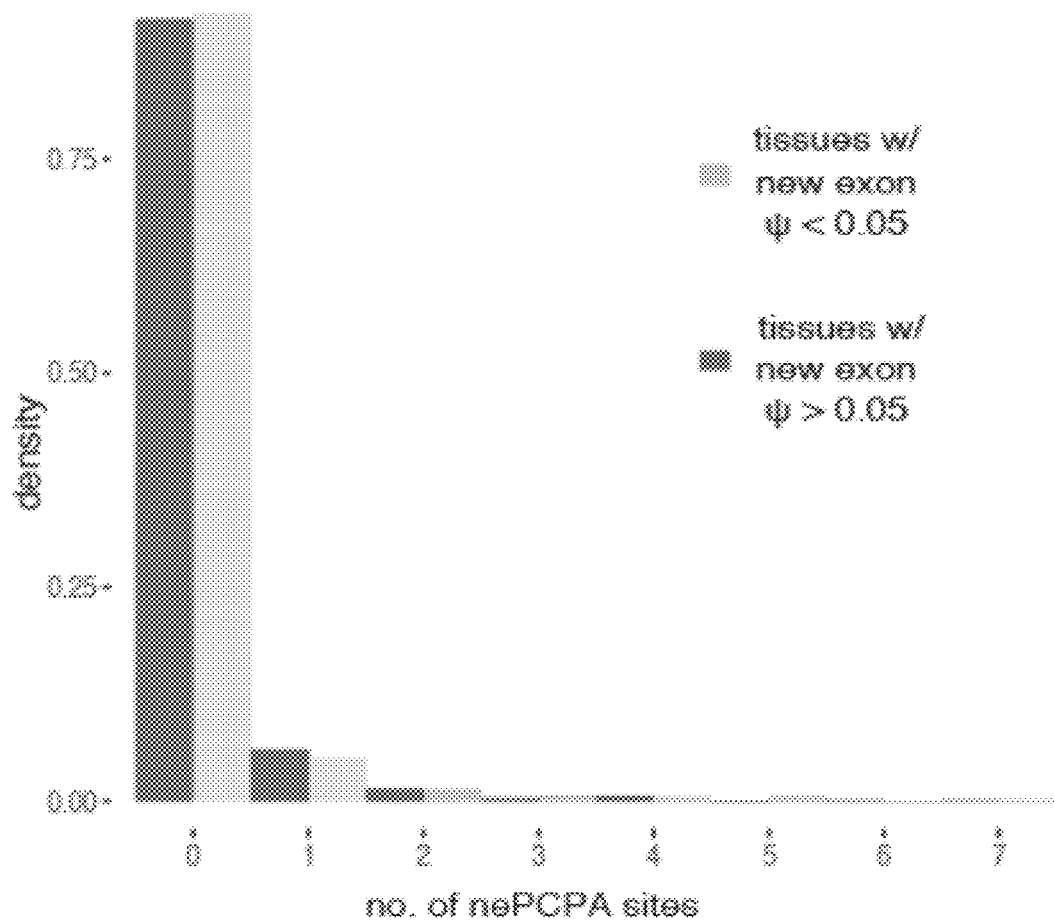
Figure 23D:
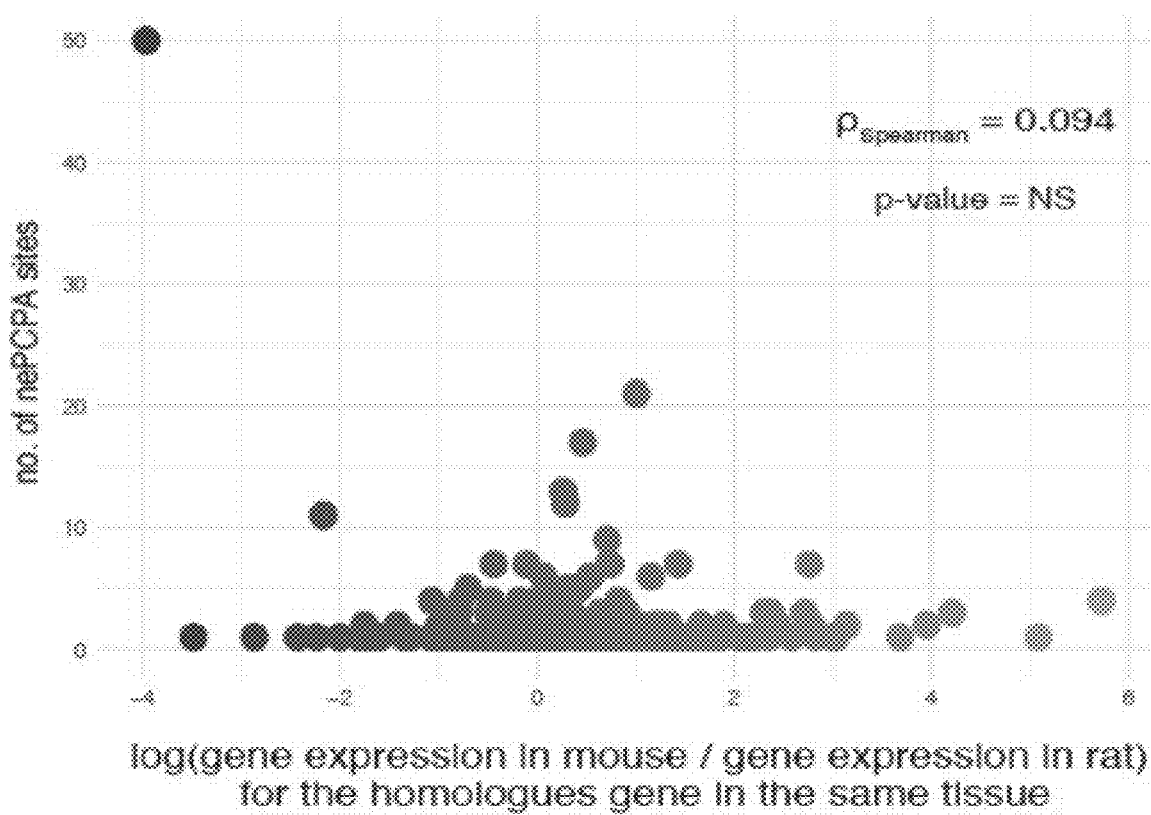

Premature cleavage and polyadenylation can produce truncated, unstable transcripts, but can be inhibited by binding of U1 snRNP near of a PCPA site (Gunderson et al., 1998; Kaida et al., 2010). If the observations above reflected effects of U1 snRNP or other splicing machinery on PCPA rather than on transcription, this would require the presence of new exon-proximal PCPA ("nePCPA") sites in affected genes. Using available polyA-seq data from five mouse tissues (Methods), it was observed that only 8.6% of genes with new exons had evidence of a nePCPA site, slightly lower than in a control set of genes (FIG. 23A). And for the subset of genes that contain nePCPA site(s), no differences in usage of the site between tissues where the new exon was spliced in and those where it was spliced out were observed (FIG. 23B and FIG. 23C). Furthermore, no relationship between the number of nePCPA sites and gene expression changes between mouse and rat was shown (FIG. 23D). Thus no evidence was found that effects on PCPA contribute significantly to exon-mediated activation of transcription starts (EMATS). Since similar effects were observed on nascent RNA (in both sense and antisense orientations) as on total mRNA levels, the results imply that EMATS impacts transcription initiation rather than later steps.

vi) Splicing of New Exons Primarily Affects Transcription Starting from the Most Proximal Upstream TSS Inhibition of new exon splicing with MO also regulated the usage of TSSs in the Gatad2b gene, mostly affecting the upstream TSS (FIG. 15C). The splicing-dependent regulation of TSSs in a gene with multiple upstream TSSs was then explored. In the Tsku gene, the mouse-specific TSS in position −1 is located within 1 kb upstream of the mouse-specific exon, while the conserved −2 promoter is located further upstream. Analysis by 5' RACE showed that both TSSs are normally used at similar levels. However, blocking inclusion of the new exon inclusion produced a shift towards the usage of TSS−2 (FIG. 16C, FIG. 17A). The down-regulation in transcription from TSS−1 was also confirmed by a decrease in H3K4me3 levels (FIG. 16D). As GTF2F1 is a core transcription factor that regulates the Tsku gene in humans, its recruitment to the mouse genome was examined. Levels of GTF2F1 and RNAPII were not impaired near TSS−2, but significantly decreased near TSS−1 in MO treated cells (FIGS. 17B-17C). The loss of signal of GTF2F1 and RNAPII near the new exon in MO treated cells suggests that the inclusion of the new exon is associated with recruitment of transcription factors and higher levels of RNAPII. Sense and antisense transcript levels (FIG. 12A), as well as nascent RNA levels (FIGS. 17D-17E) confirmed that total usage of TSS−2 does not significantly change, while TSS−1 levels are almost completely impaired in MO treated cells. These observations demonstrate that splicing of new exons can regulate the usage of alternative TSS and primarily affects transcription starting from the upstream TSS located most proximal to the splicing event.

vii) The Creation of a 3' Splice Site Promoted the Inclusion of the Mouse-Specific Exon Only in Constructs with the Wild Type 5' Splice Site If genes with mouse-specific new exons have increased gene expression because they activate TSSs, promoting the inclusion of a cryptic exon in the rat genome by creating a splice site should activate proximal TSS. Rat Tsku transcripts only use the ancestral TSS−2; however, the homologous regions of TSS−1 and mouse-specific new exon have high sequence identity with the mouse genome including the presence of both 5' splice sites (FIG. 18A). The regulatory region of the rat Tsku gene upstream of the coding sequence of Renilla luciferase was cloned and the 3' splice site from the mouse genome (rn+mm 3'ss), as well as a stronger 3' splice site (rn+strong 3'ss) was recreated to promote inclusion of the mouse-specific exon in the rat sequence, maintaining or mutating the wild-type 5' splice site (m+mm 3'ss+mut 5'ss). The creation of a 3' splice site promoted the inclusion of the mouse-specific exon only in constructs with the wild type 5' splice site (FIG. 18B), and increased gene expression levels measured by Renilla luciferase (hRLuc) activity normalized to firefly luciferase (ppLuc) (FIG. 16E). Although outside its endogenous context, TSS−1 is used at basal levels in the construct, the mouse-specific exon activates the usage of TSS−1 only in the presence of a wild-type 5' splice site, demonstrating that the effect depends on the inclusion of the mouse-specific exon rather than on the creation of the 3' splice site sequence per se (FIG. 16F and FIG. 18C). These results reveal a novel evolutionary mode of gene expression regulation in which the inclusion of a species-specific new exon enhances gene expression by activating a proximal and upstream TSS.

viii) Creation of a New Splice Site Activates the Use of a Cryptic Promoter Nearby Next, how splicing might affect use of different upstream TSSs was explored. In the Tsku gene, the mouse-specific TSS in position −1 is located within 1 kb upstream of the mouse-specific exon, while the conserved TSS-2 is located further upstream. Analysis by 5' RACE showed that both TSSs are normally used at similar levels in mouse fibroblasts. However, inhibiting splicing of the new exon by MO resulted in lower use of TSS-1 (FIG. 16C and FIG. 17A). The strong down-regulation of transcription from TSS-1 observed by 5' RACE was confirmed by qRT-PCR of nascent RNA, in both sense and antisense orientations (FIGS. 17D-17E). This shift was accompanied by a 3-fold decrease in H3K4me3 levels near TSS-1 in MO-treated cells (FIG. 16D). However, levels of 13K4me3 near TSS-2 were unchanged, confirming that TSS-2 transcription is not affected (FIG. 16D). In cells treated with MOs, levels of GTF2F1 and RNAPII decreased by almost 3-fold near TSS-1 but were unchanged near TSS-2 (FIG. 17B and FIG. 17C). These observations suggest that splicing of the new exon contributes to recruitment of core transcription machinery to the proximal TSS-1. Moreover, the loss of signal for GTF2F1 and RNAPII near the new exon following MO treatment suggests that inclusion of the new exon is associated with recruitment of transcription factors and higher levels of RNAPII, consistent with functional interactions between GTFs and splicing machinery observed previously (Damgaard et al., 2008; Das et al., 2007). These observations confirm that splicing of new exons can regulate the usage of alternative TSSs, with predominant effects on proximal upstream promoters, consistent with the correlations observed in FIGS. 13C, 13E, and 13F.

To dissect the impacts of individual splice sites and splicing levels, an exon corresponding to the mouse-specific new exon was created in the rat Tsku gene and assessed effects on transcription. In the rat Tsku locus, transcripts are predominantly transcribed from the distal TSS-2. However, the regions homologous to TSS-1 and the mouse-specific new exon have high sequence identity with the mouse genome: both 5' splice sites are present in rat, but no YAG is present in rat near the location of the mouse 3' splice site, likely preventing splicing (FIG. 18A). To introduce the desired mutations, the 5' end of the rat Tsku gene upstream of the coding sequence of Renilla luciferase was cloned and the 3' splice site that is present in the mouse genome (rn+mm 3'ss) was recreated, as well as a stronger 3' splice site (rn+strong 3ss), while either maintaining or mutating the native rat 5' splice site sequence (mm 3'ss+mut 5'ss). Strikingly, the creation of a 3' splice site promoted the inclusion of an exon analogous to that observed in mouse in constructs with an intact 5' splice site (FIG. 18B), indicating that this mutation is sufficient to create a new exon in the rat gene. In the presence of both 3' and 5' splice sites, but not when either splice site was absent, total gene expression levels increased, as measured by luciferase activity (FIG. 16E). By 5' RACE analysis, TSS-1 is used at basal levels in the minigene. However, the mouse-specific exon activates the usage of TSS-1 by 3-fold in the presence of a 5' splice site, demonstrating that the effect on TSS usage depends on splicing of the mouse-specific exon rather than merely the presence of a 3' splice site sequence (FIG. 16F and FIG. 18D).

Figure 16G:
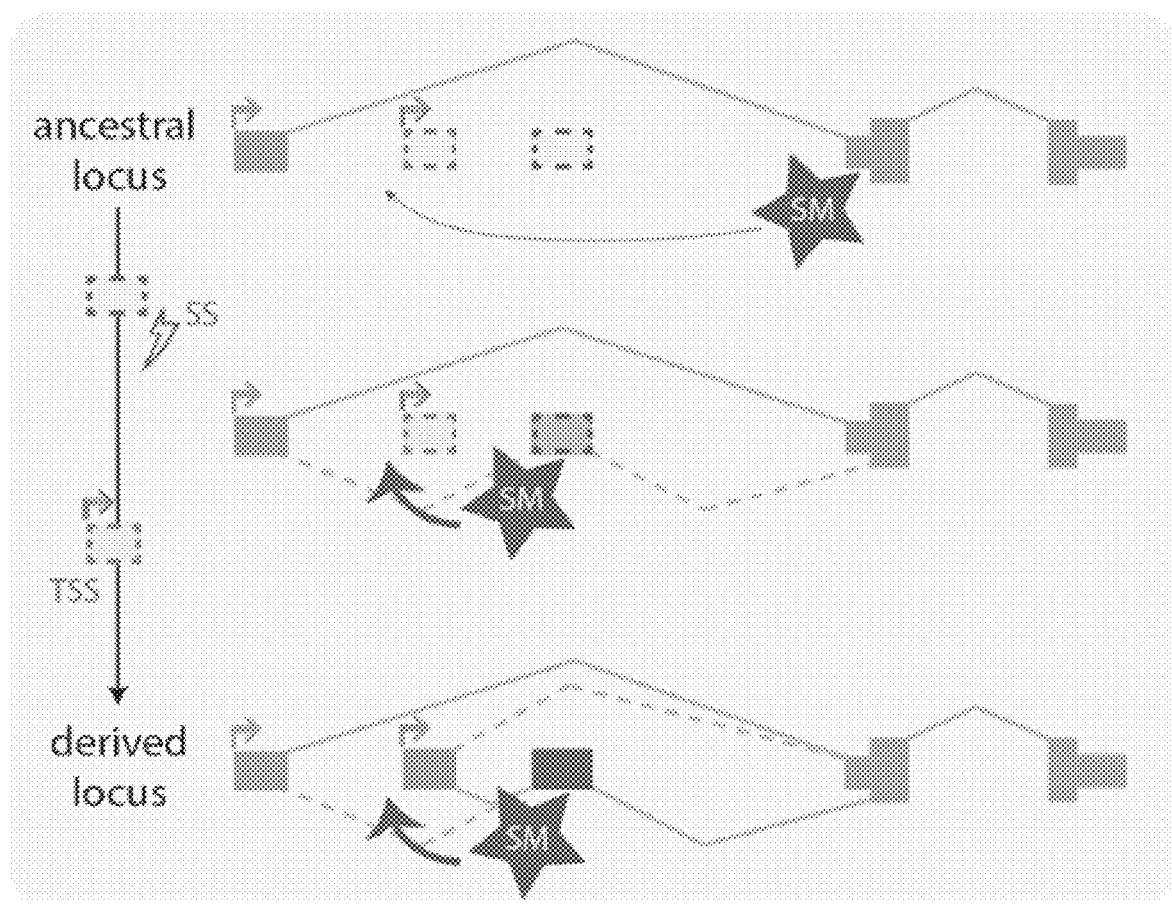
Figure 19B:
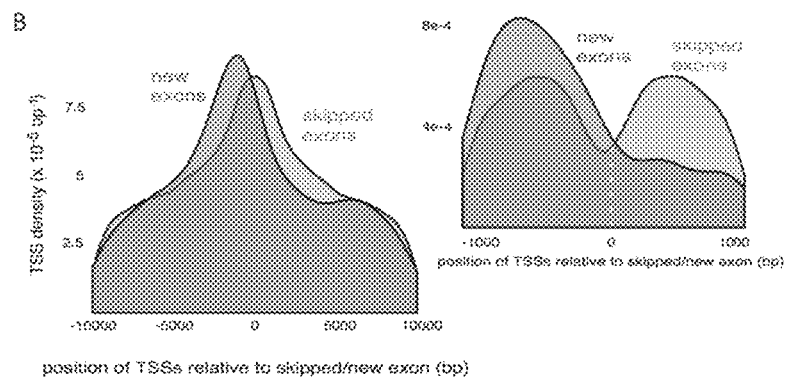
Figure 19C:
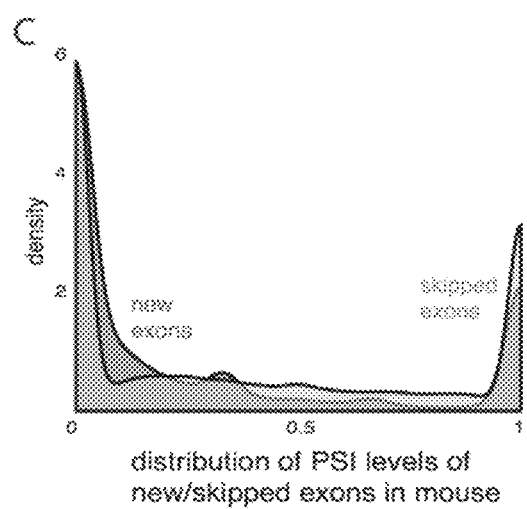

In some examples studied previously, species-specific alternative splicing alters protein function (Gracheva et al., 2011; Gueroussov et al., 2015). The observations support the existence of a distinct evolutionary pathway in which, following a mutation that generates a new internal exon, splicing of the new exon in transcripts from a distal upstream promoter activates a cryptic proximal upstream promoter; and transcripts from the new promoter also include the exon, further activating the new promoter in a sort of positive feedback loop. The resulting new TSS produces novel transcript isoforms and higher gene expression in tissues where the upstream promoter is active and the exon is included (FIG. 16G). Conversely, loss of an internal exon may result in loss of a weak upstream promoter that is dependent on splicing of the exon.

ix) TSSs have Similar Overall Distribution of PSI Values in Genes with New Exons and Genes with SEs in Mice; Efficiently Spliced Exons Activate Use of Weak Proximal TSSs To investigate the genomic scope of the relationship between splicing and alternative TSS usage, it was questioned whether the inclusion of alternative skipped exons (SE) in general—not just those that evolved recently—can influence start site selection. 49,488 SEs in mouse RNA-seq data, distributed across 13,491 genes were identified using conservative criteria (Table 3). Analyzing unique SEs with TSS-exon distances matching those of new exons, no significant association between SE inclusion and use of proximal upstream TSSs overall was observed (FIG. 19A). In addition, a symmetrical distribution of TSSs around the locations of SEs was observed, which was distinct from the upstream-biased distribution seen relative to new exons (FIG. 19B). These differences suggest that genes with new exons have distinct properties that favor linkage of splicing with transcription.

Figure 19D:
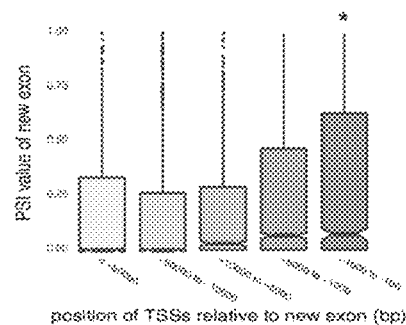
Figure 19E:
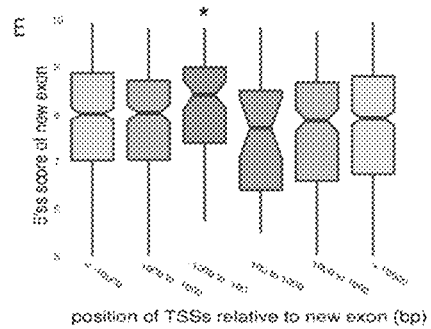
Figure 19F:
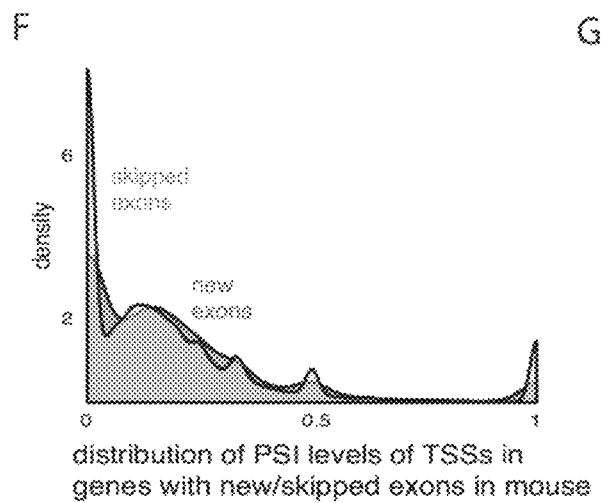
Figure 19G:
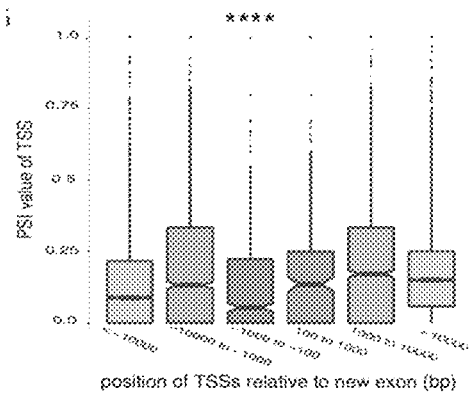
Figure 20A:
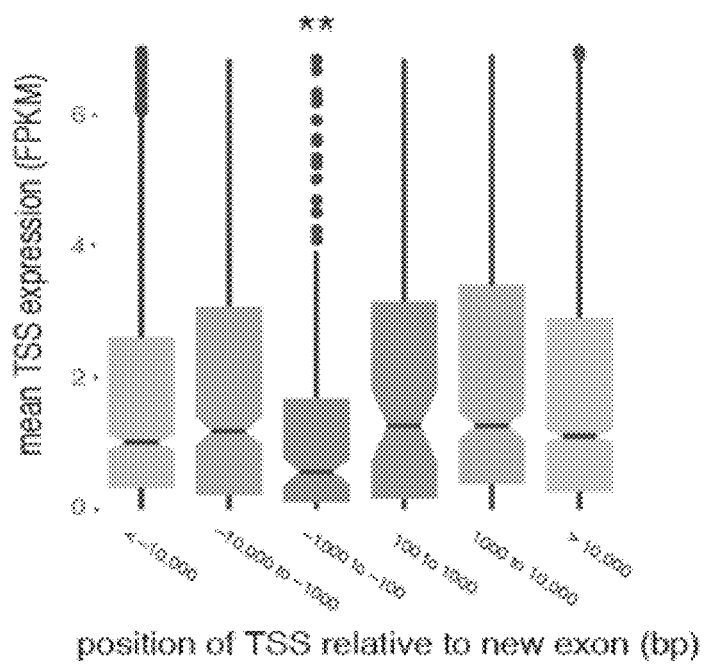
FIGS. 20A-20G include diagrams showing that inclusion of skipped exons favors the usage of weak TSSs.
Figure 20B:
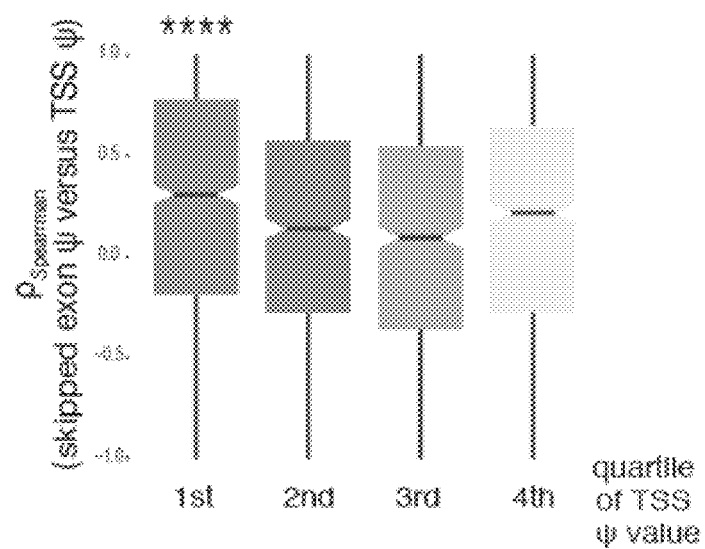
Figure 20C:
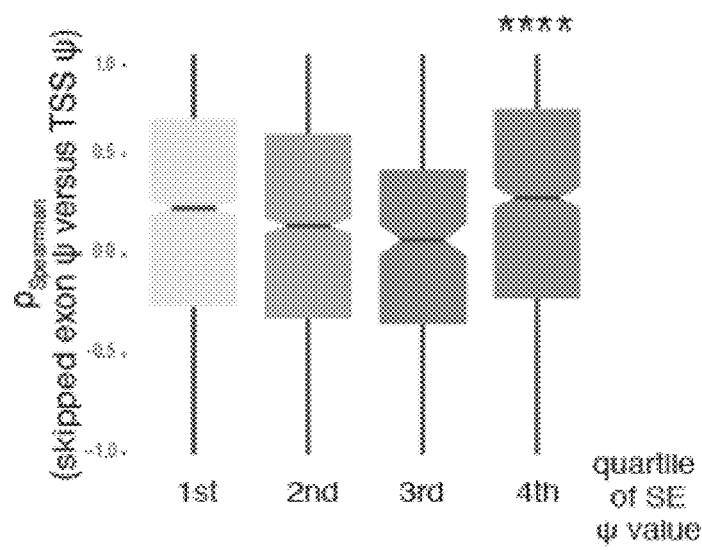
Figure 20D:
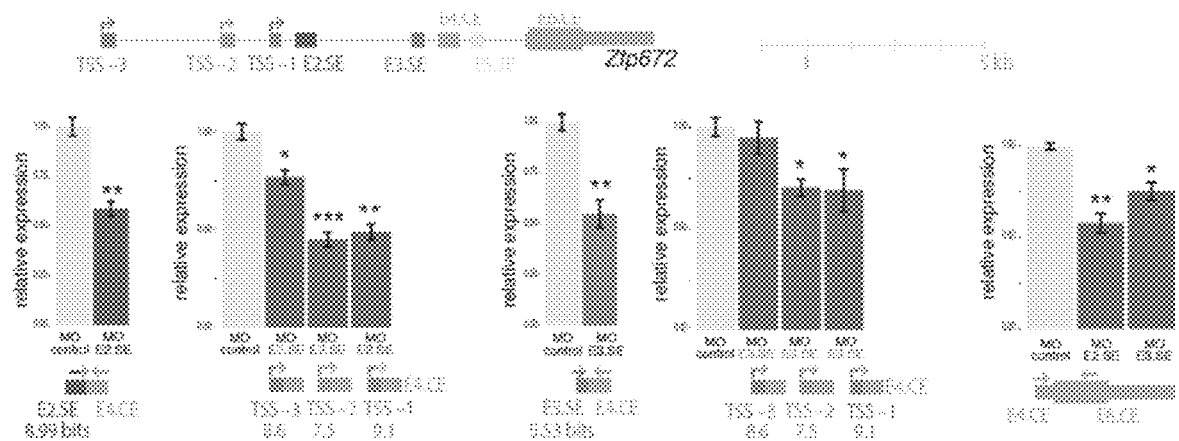
Figure 20E:
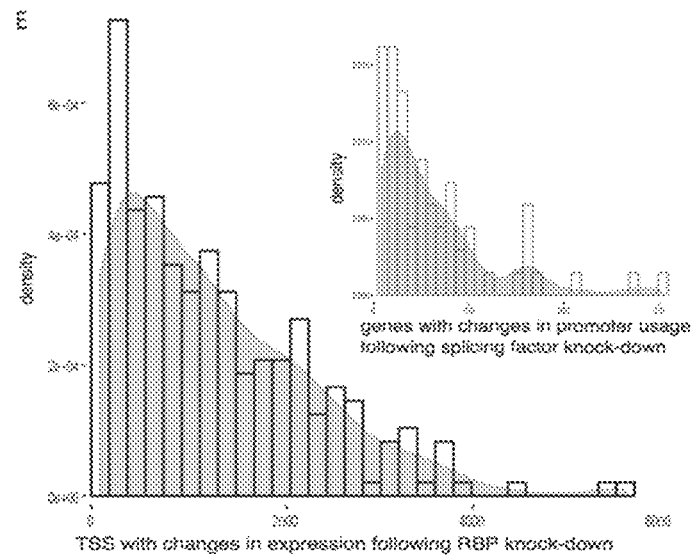
Figure 20F:
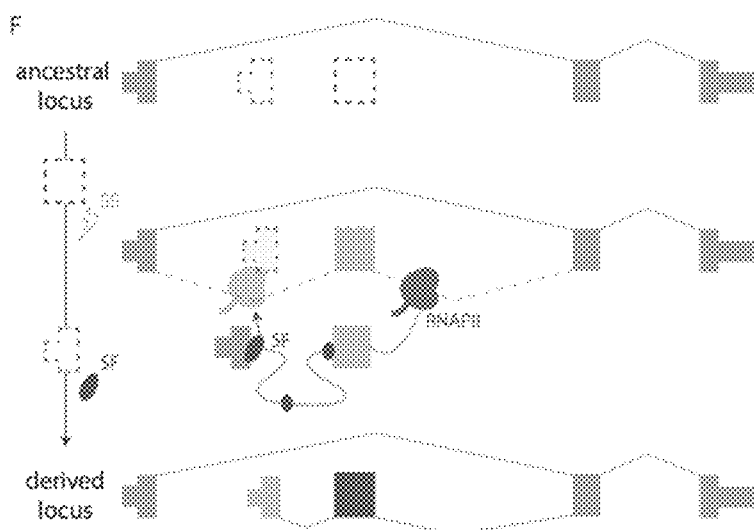
Figure 20G:
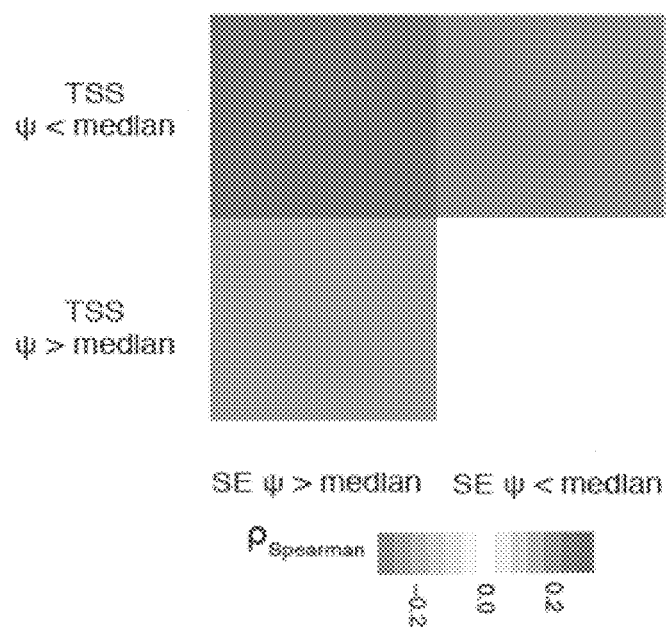
Figure 24A:
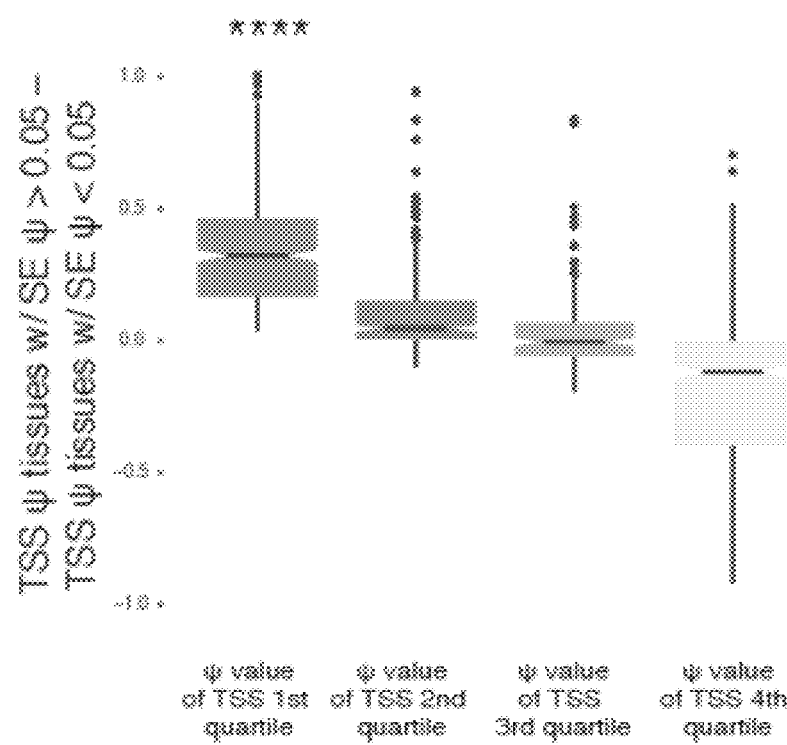
FIGS. 24A-24C include plots showing the differences in TSS usage in tissues with high vs low inclusion of skipped exons.
Figure 24B:
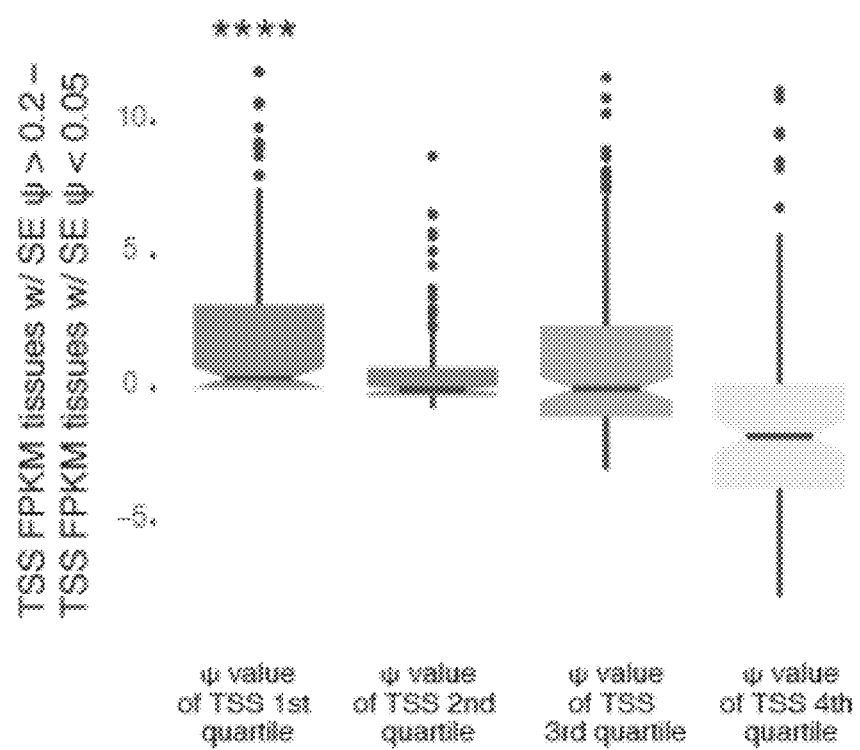
Figure 24C:
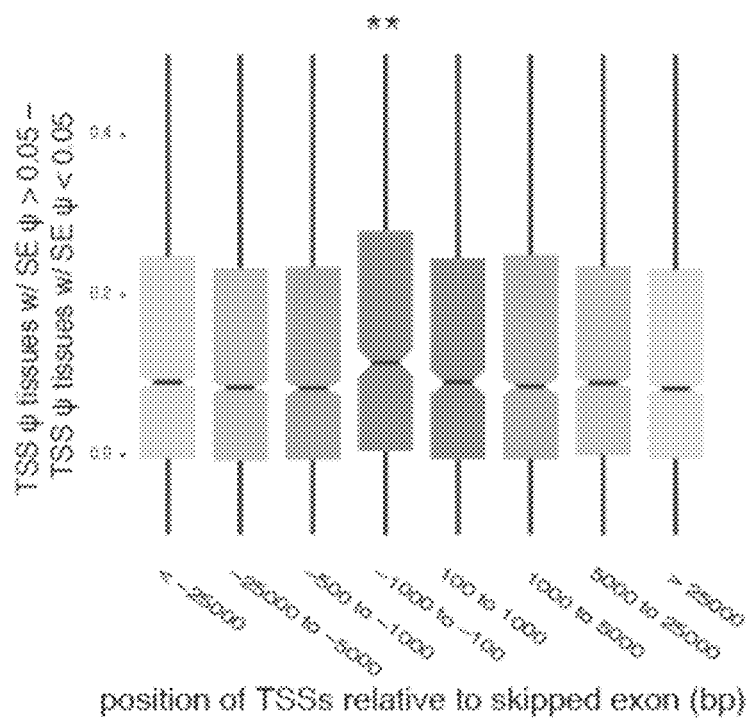

Examining other features of loci with new exons, it was observed that, although new exons tend to have lower PSI values than SEs overall (FIG. 19C), those new exons with proximal upstream TSSs tended to have higher PSI values and stronger 5' splice sites (FIGS. 19D-19E) when the TSSs are located within 1 kb upstream. Furthermore, although the distribution of TSS PSI values was similar in genes with new exons and genes with SEs generally (FIG. 19F), those TSSs located proximal and upstream of new exons had lower average expression levels across tissues than TSSs in other locations (FIG. 20A). Although the distribution of TSS PSI values was similar in genes with new exons and genes with SEs generally, the TSSs located proximal and upstream of the new exons have the lowest FPKMs and PSI levels (FIG. 20A and FIG. 19G). These observations suggested that the link between splicing and TSS usage is most pronounced when the promoter is intrinsically weak and splicing activity is high.

x) Intrinsic Transcriptional Strength of TSSs and Intrinsic Splicing Strength of Exons Modulate the Association Between Transcription Initiation and Splicing To investigate whether the intrinsic transcriptional activity or "strength" of the TSS and the intrinsic splicing activity or "strength" of the exon and their relative locations modulate the association between transcription initiation and splicing, SEs and their most proximal and upstream TSS were grouped into four bins from weak to strong on the basis of the TSS PSI value, and separately for the SE PSI value, and analyzed the correlation between TSS PSI and SE PSI separately for each bin. Notably, it was observed that TSS usage was most highly correlated with exon inclusion for the lowest quartile of TSS PSI values (FIGS. 20B, 24A, and 24B) and for the highest quartile of SE PSI (FIGS. 20C and 24C). As was shown for intron-mediated enhancement that weaker promoters tend to prompt stronger enhancement by introns, weak TSSs showed a significantly higher correlation with inclusion of SE (FIG. 20B). Moreover, strong SE are highly associated with usage of TSS (FIG. 20C), suggesting that weak TSSs can be activated when located proximal and upstream of a strong splicing event. Thus, evidence was found that the EMATS observed for new exons occurs for a subset of general SEs. Robust effects were observed when a weak promoter is located upstream of a highly included SE, which occurred in 3,833 mouse genes, with the strongest effects seen for proximal weak promoters, which occurred in 1777 mouse genes (FIG. 20G and Table 3). In humans, 3548 genes with EMATS organization and 1098 genes with EMATS structure in which the weak promoter is also proximal to the SE (within 2 kb) were identified. Considering constitutive exons the number of identified genes increases by 3-fold.

Figure 21:
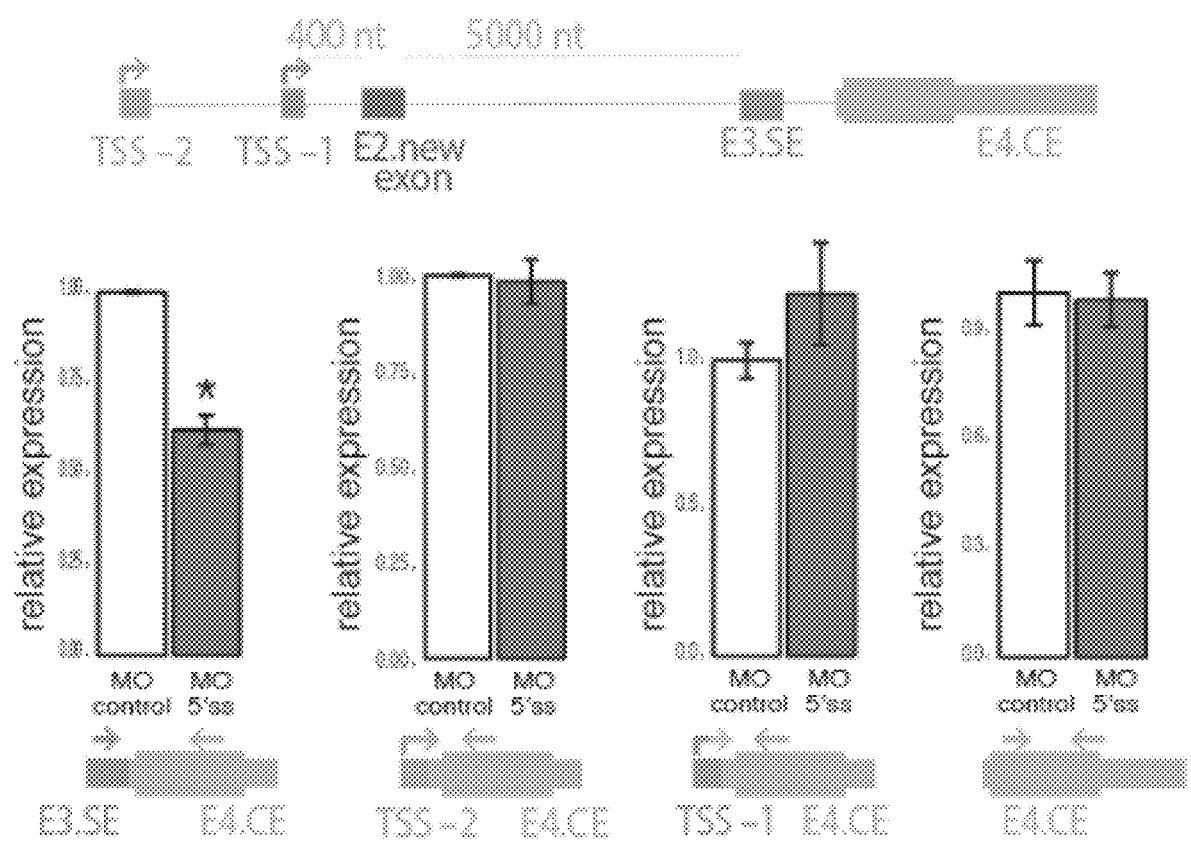
FIG. 21 includes charts showing that splicing perturbations of skipped exons affect proximal TSSs. Fold change in inclusion (left), exclusion levels (middle) and total levels (right) of the skipped exon in Tsku gene (E3.SE) from both TSSs measured by isoform-specific qPCRs. Exclusion levels are measured from both alternative first exons to the following constitutive exon downstream the skipped exon. NIH3T3 cells were transfected with control MO or MO targeting the 5' splice site of the skipped exon. Mean±SEM of displayed distributions. n=3 biological replicates. Statistical significance indicated by asterisks corresponds to one-way ANOVA, Tukey post hoc test.

To further investigate the distance dependence of splicing effects on TSS use, changes in TSS usage when inhibiting the inclusion of a SE in the mouse Tsku locus located more than 6 kb downstream of the TSSs was analyzed. Perturbations of the splicing of this exon caused no detectable changes in TSS usage (FIG. 21), consistent with a requirement for proximity of spliced exon to TSS for EMATS activity. Considering another mouse gene, Zfp672 (Zinc Finger Protein 672)—chosen because it contained multiple TSSs and SEs expressed in mouse fibroblasts—it was observed that inhibition of the stronger upstream SE in the locus affected the usage of TSSs more dramatically than inhibition of the weaker downstream SE in the same gene (FIG. 20D). A weaker distal TSS (TSS–2) was impacted to similar degrees as a stronger proximal TSS (TSS–1) by splicing perturbations of these SEs (FIG. 20D). Together, these observations confirm that splicing of SEs can impact TSS use, particularly when the TSS is intrinsically weak, the SE is highly included, and the TSS is located proximal and upstream of the SE. The generalization of EMATS to SEs more broadly implies that gene expression may commonly be regulated through effects on splicing of promoter-proximal exons. These results demonstrate that splicing of SEs in mouse can regulate the usage of TSSs. This effect is stronger when (i) SEs and TSSs are located more proximally; (ii) SEs are more highly included; and (iii) TSSs are weaker.

xi) In Human, Splicing Regulators Also Play Important Roles in Selecting TSSs

Figure 22A:
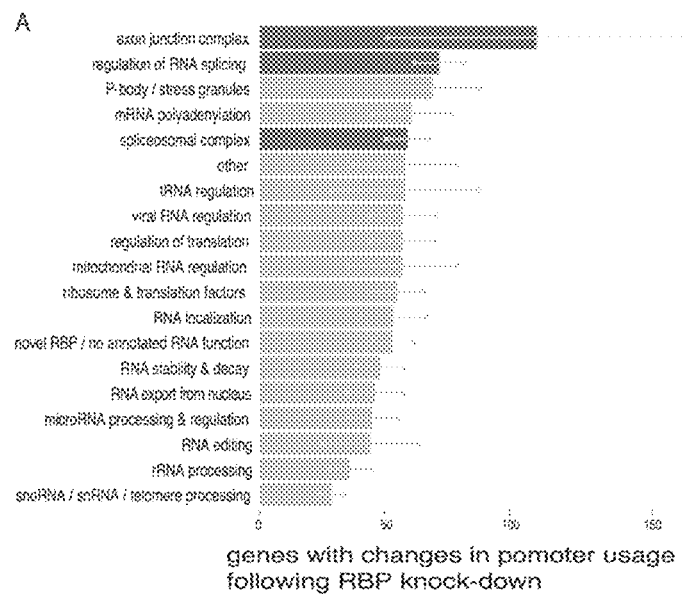
FIGS. 22A-22B include charts showing that splicing regulators play important roles in TSS choice.
Figure 22B:
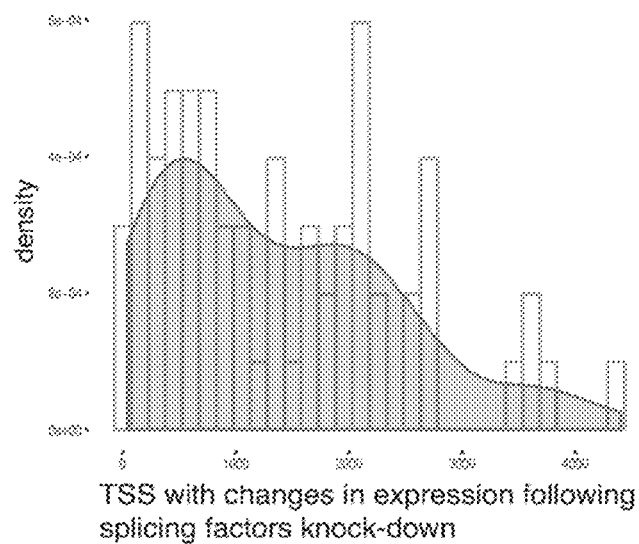

To investigate the extent to which splicing patterns regulate TSS usage, human RNA-sequencing data generated from the ENCODE project was analyzed to assess the transcriptome-wide changes in TSS expression by depletion of 250 RNA binding proteins (RBPs) including 67 splicing factors. Nearly all RBPs affected the expression of TSSs (FIG. 20E). Greater change in TSSs usage per gene was associated with depletion of splicing factors (FIG. 20E and FIGS. 22A-22B) suggesting that, also in humans, splicing regulators play important roles in choosing the TSSs. These findings suggest the existence of mechanisms that coordinate splicing choices with the usage of TSSs. A possible mechanism consistent with the data herein (FIG. 20F) proposes that the creation of a splice site during evolution promotes the inclusion of a new exon. The new splicing event recruits the spliceosome complex and splicing factors. These splicing factors co-associate with the transcription machinery as previously described, and could create a high concentration of RNAPII and core transcription factors at a new site. The recruitment of RNAPII and other components of the pre-initiation complex could activate weak TSSs located proximal and upstream of the splicing event. While transcripts at the ancestral locus start from a single TSS, the inclusion of a new splicing event at the derived locus triggers the usage of alternative TSSs to fine tune gene expression. Taken together, the results demonstrate that splicing controls gene expression by regulating transcription initiation sites and reveal an unexpected role for splicing in activating weak proximal TSSs.

xii) Splicing Factors Impact TSS Use and EMATs Connection to Neurogenesis

Figure 25A:
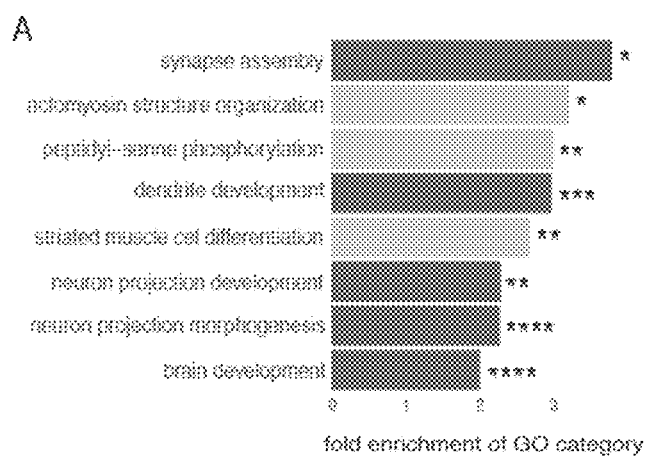
FIGS. 25A-25I include diagrams showing that a subset of splicing factors impact TSS use and interact with transcription machinery.
Figure 25B:
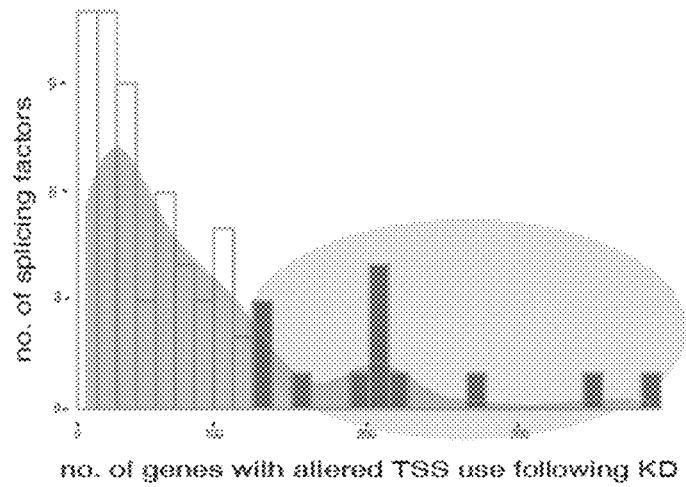
Figure 25C:
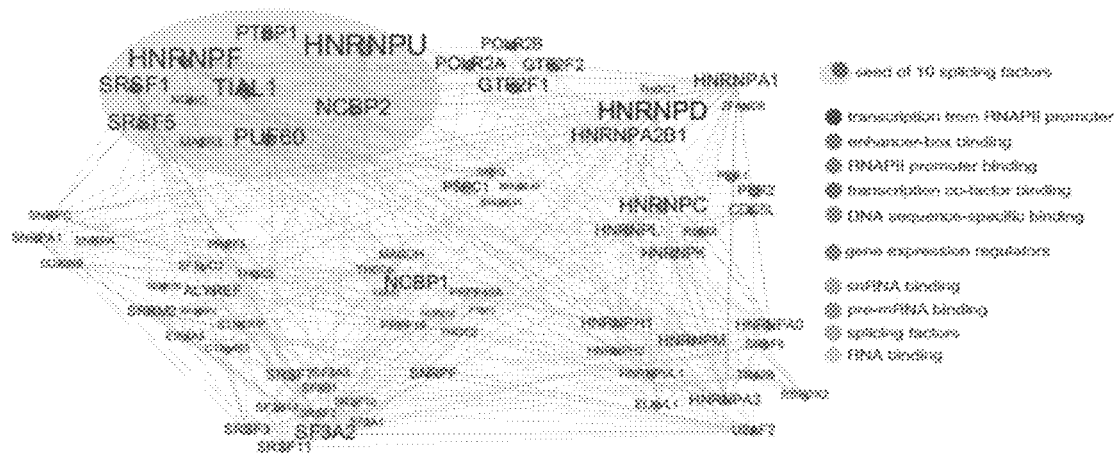
Figure 25D:
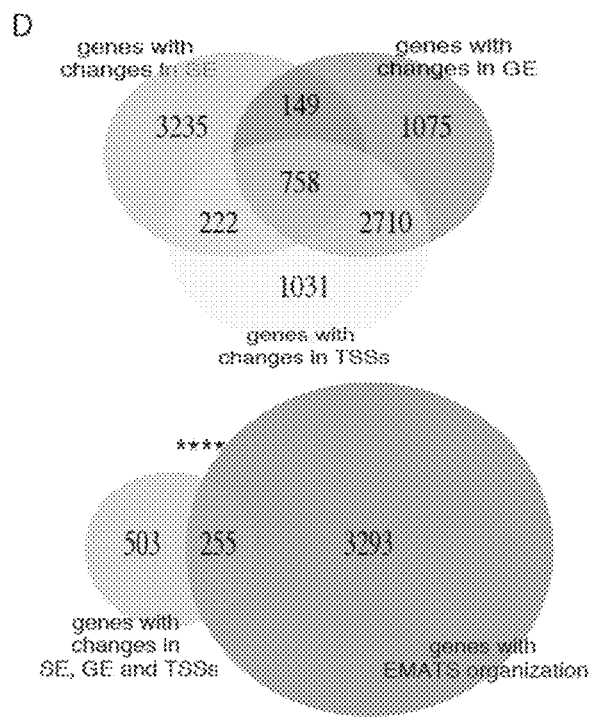

To investigate the potential biological role of regulation of gene expression via EMATS, the functions of genes with EMATS structure were analyzed. Interestingly, the 1777 mouse genes and the 1098 human genes with the strongest EMATS potential are enriched for functions in brain development, neuron projection, synapse organization and related functions (FIG. 25A and FIG. 25F). This observation suggests that regulation via EMATS may contribute to neuronal differentiation, i.e. that splicing changes resulting from neuron-specific changes in splicing factor activity might trigger expression changes via EMATS that contribute to neuronal gene expression programs.

The mechanistic link between splicing and TSS usage could be mediated by splicing machinery, splicing factors, or exon junction complex components, particularly those factors that interact with transcription machinery, transcription factors or chromatin. To explore potential links between splicing factors and TSS use, transcriptome-wide changes in alternative TSS usage following knockdown of RNA-binding proteins (RBPs) using data from a recent ENCODE project (Van Nostrand et al., 2019) was analyzed. This analysis detected large numbers of TSS changes (FIG. 25F). Depletion of factors involved in RNA splicing generally impacted larger numbers of TSSs than did depletion of other RBPs (FIG. 25B and FIG. 20E). The ten splicing factors associated with the largest numbers of changes in TSS usage (FIG. 22A) included PTBP1, whose downregulation plays a central role in neurogenesis. Using protein-protein interaction (PPI) data from the STRING database (Szklarczyk et al., 2015), it was observed that these ten splicing factors interact with 65 other proteins, including subunits of RNA-PII and GTFs (FIG. 25C). Compared with the PPI partners of the ten splicing factors whose depletion affected the fewest TSSs, these 65 proteins were enriched for functions in enhancer binding, transcription factor activity and promoter proximal binding (FIGS. 25C, 25G, and 25H). Together, these observations indicate that some splicing factors have wider impacts on promoter choice than previously recognized, and identify extensive interactions of these factors with core transcription machinery.

To investigate whether neuron-related splicing factors could regulate expression via EMATS, transcriptome-wide changes following PTBP1 knockdown using the ENCODE data (Van Nostrand et al., 2019) was analyzed. Following PTBP1 knockdown, 758 genes had significant changes in SE splicing, TSS usage and gene expression, including 255 genes with EMATS organization; the latter represents a 1.7-fold enrichment over the background frequency of EMATS genes (FIG. 25D). Among these 255 genes, the majority (165) also contained a PTBP1 eCLIP peak and had changes in TSS usage and gene expression that matched the direction expected from EMATS based on the direction of the change in splicing. For example, in the human BMF (Bcl2 Modifying Factor) gene reduced exon inclusion accompanied by decreased use of upstream proximal TSSs and decreased gene expression following PTBP1 knockdown (FIG. 25I) was observed. The results above suggest that splicing factors, including a key factor involved in neuronal differentiation, contribute to gene expression programs via EMATS regulation downstream of their effects on splicing.

Discussion

Here, it has been shown that creation of a new internal exon in a gene—during evolution, by directed mutation or by altered regulation—can activate transcription from an upstream TSS and thereby boost gene expression levels, a phenomenon which we refer to as EMATS. The study highlights several features of this relationship: (i) it requires exon splicing, not merely presence of a 5' or 3' splice site; (ii) it is more potent when the exon is highly included and (iii) when the promoter is intrinsically weak: (iv) it is sensitive to genomic distance, occurring most robustly when exon and promoter are within 1-2 kilobases; and (v) the above features occur in thousands of mammalian genes (Table 3).

Figure 25E:
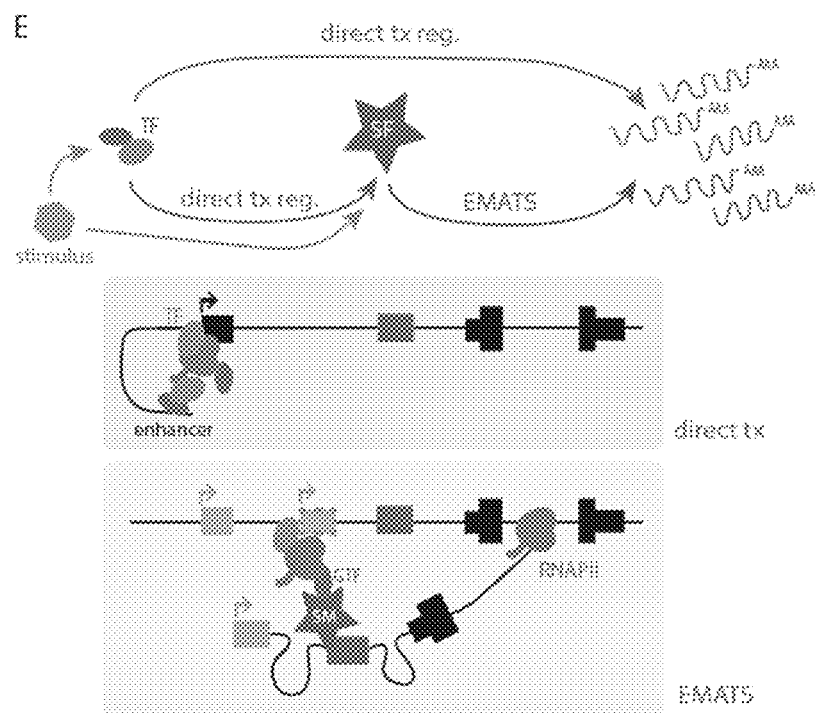
Figure 25F:
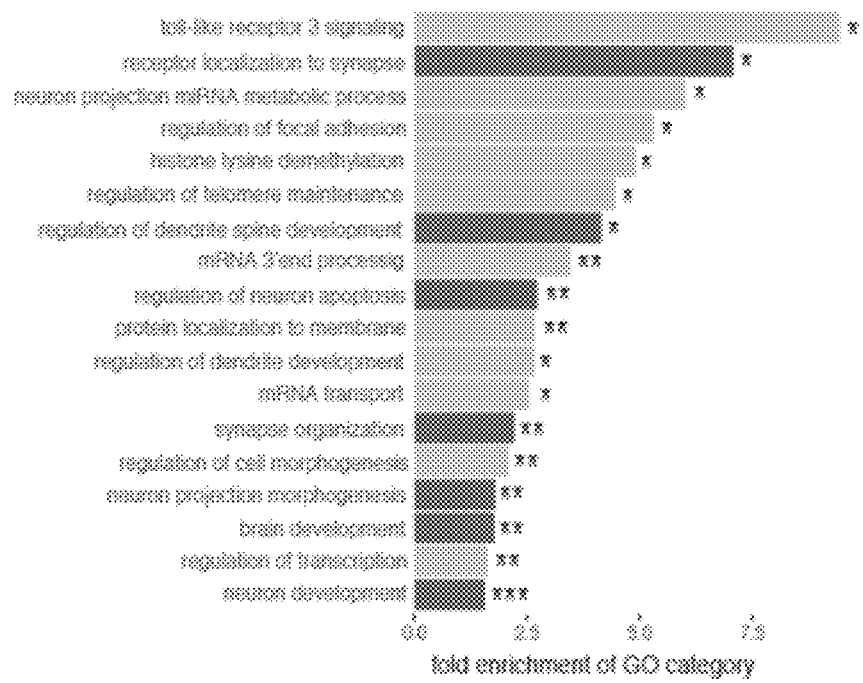
Figure 25G:
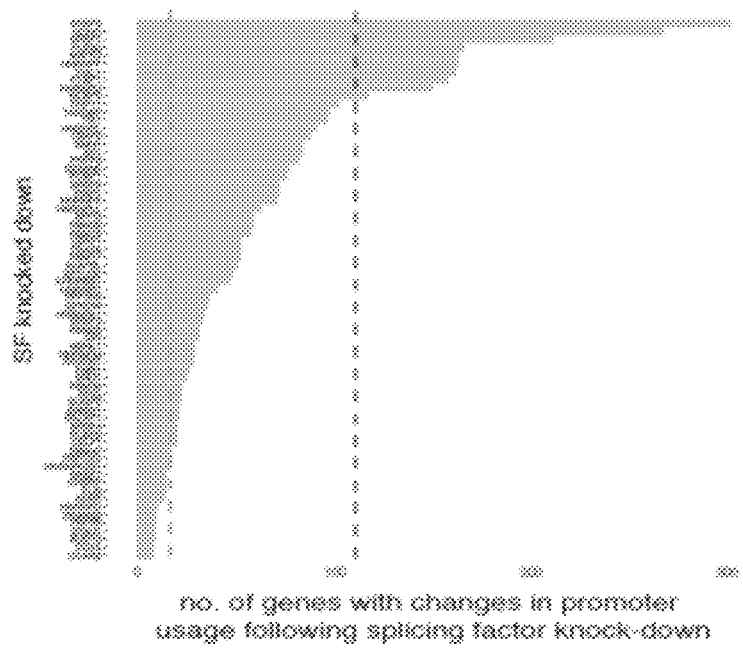
Figure 25H:
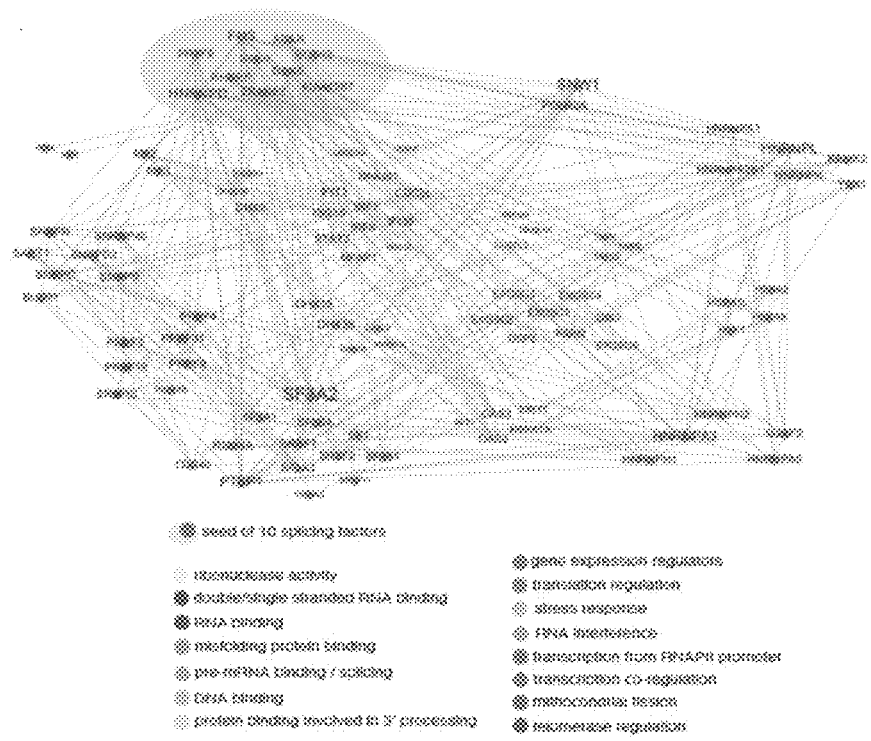
Figure 25I:
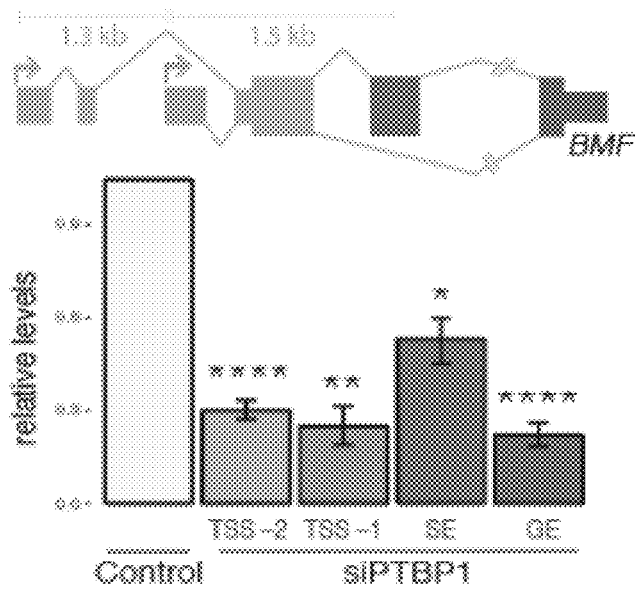

The most straightforward model to explain the above features (among other possible models) would involve direct positive effects of splicing components recruited to transcripts during transcription on recruitment of transcription machinery to nearby upstream promoters (FIG. 25E). Splicing often occurs cotranscriptionally, and it is clear that splicing machinery and splicing factors are often recruited to nascent transcripts which are being transcribed and are therefore tethered to the gene locus. The splicing of exons can directly recruit core transcription machinery to the local vicinity, which may increase local concentration and occupancy of RNAPII at nearby promoters to increase transcription initiation. The involvement of splicing machinery or proteins deposited on the transcript in connection with splicing would explain feature (i) above, while the more efficient recruitment of splicing machinery to more efficiently spliced exons would explain feature (ii). Recruitment of RNAPII or GTFs might be expected to activate transcription more effectively at weaker promoters where RNAPII recruitment is limiting than at strong promoters with higher intrinsic RNAPII occupancy, explaining feature (iii). A requirement for direct physical interaction between splicing machinery and RNAPII or GTFs might constrain the genomic distances involved, feature (iv). However, the varied chromatin conformations of different gene loci— which, in some cases, might involve chromatin loops between promoters and alternative exons—might alter distance requirements for different genes. Frequent occurrence of the evolutionary path outlined in FIG. 16G and/or selection gene architectures that enable alternative 5' UTRs, may explain the widespread occurrence of EMATS organization in mammalian genomes, feature (v).

The EMATS phenomenon has both evolutionary and regulatory implications. It is proposed that emergence of new internal exons and of new TSSs are linked (FIG. 16G). Once so activated, the new TSS produces new transcript isoforms and higher overall expression of the gene in specific tissues, providing a substrate for the regulatory evolution of the gene. The most obvious regulatory role for EMATS would be as a means for splicing factors to contribute to gene expression programs involved in differentiation or cellular responses to stimuli (FIG. 25E). Specifically, it is proposed that external stimuli such as growth factors or changes in cellular environment trigger gene expression changes not only via direct effects on TF activity but also by effects on splicing factor activity or changes in splicing factor levels downstream of affected TFs, yielding additional gene expression changes via EMATS. An additional implication of the findings is that targeted activation (or repression) of the expression of a gene for research or therapeutic purposes may be achievable by use of compounds such as antisense oligonucleotides or small molecules that enhance or inhibit the splicing of an appropriately located promoter-proximal exon. Here, EMATS involving alternative exons are focused on because of its endogenous regulatory potential, but such intervention could target appropriately positioned constitutive exons as well, roughly triplicating the number of potentially targetable genes. Recent studies have broadened the definition of enhancers, showing that some gene promoters also function as enhancers; the findings herein support further broadening of this definition to include some exons as well.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

REFERENCES

S. Gueroussov et al., An alternative splicing event amplifies evolutionary differences between vertebrates. Science. 349, 868-873 (2015).

G. Yeo, C. B. Burge, Maximum entropy modeling of short sequence motifs with applications to RNA splicing signals. J. Comput. Biol. 11, 377-394 (2004).

Agarwal, N., and Ansari, A. (2016). Enhancement of Transcription by a Splicing-Competent Intron Is Dependent on Promoter Directionality. PLoS Genet. 12, e1006047.

Damgaard, C. K., Kahns, S., Lykke-Andersen, S., Nielsen, A. L., Jensen, T. H., and Kjems, J. (2008). A 5' splice site enhances the recruitment of basal transcription initiation factors in vivo. Mol. Cell 29, 271-278.

Das, R., Yu, J., Zhang, Z., Gygi, M. P., Kramer, A. R., Gygi, S. P., and Reed, R. (2007). SR proteins function in coupling RNAP II transcription to pre-mRNA splicing. Mol. Cell 26, 867-881.

Derti, A., Garrett-Engele, P., Macisaac, K. D., Stevens, R. C., Sriram, S., Chen, R., Rohl, C. A., Johnson, J. M., and Babak, T. (2012). A quantitative atlas of polyadenylation in five mammals. Genome Res. 22, 1173-1183.

Gallegos, J. E., and Rose, A. B. (2017). Intron DNA Sequences Can Be More Important Than the Proximal Promoter in Determining the Site of Transcript Initiation. Plant Cell 29, 843-853.

Gracheva, E. O., Cordero-Morales, J. F., Gonzalez-Carcacia, J. A., Ingolia, N. T., Manno, C., Aranguren, C. I., Weissman, J. S., and Julius, D. (2011). Ganglion-specific splicing of TRPV1 underlies infrared sensation in vampire bats. Nature 476, 88-91.

Gunderson, S. I., Polycarpou-Schwarz, M., and Mattaj, I. W. (1998). U1 snRNP Inhibits Pre-mRNA Polyadenylation through a Direct Interaction between U1 70K and Poly(A) Polymerase. Mol. Cell 1, 255-264.

Kaida, D., Berg, M. G., Younis, I., Kasim, M., Singh, L. N., Wan, L., and Dreyfuss, G. (2010). U1 snRNP protects pre-mRNAs from premature cleavage and polyadenylation. Nature 468, 664-668.

Merkin, J. J., Chen, P., Alexis, M. S., Hautaniemi, S. K., and Burge, C. B. (2015). Origins and impacts of new mammalian exons. Cell Rep 10, 1992-2005.

Merkin, J., Russell, C., Chen, P., and Burge, C. B. (2012). Evolutionary dynamics of gene and isoform regulation in Mammalian tissues. Science 338, 1593-1599.

Scruggs, B. S., Gilchrist, D. A., Nechaev, S., Muse, G. W., Burkholder, A., Fargo, D. C., and Adelman, K. (2015). Bidirectional Transcription Arises from Two Distinct Hubs of Transcription Factor Binding and Active Chromatin. Mol. Cell 58, 1101-1112.

Szklarczyk, D., Franceschini, A., Wyder, S., Forslund, K., Heller, D., Huerta-Cepas, J., Simonovic, M., Roth, A., Santos, A., Tsafou, K. P., et al. (2015). STRING v10: protein-protein interaction networks, integrated over the tree of life. Nucleic Acids Res. 43, D447-D452.

Van Nostrand, E. L., Freese, P., Pratt, G. A., Wang, X., Wei, X., Xiao, R., Blue, S. M., Chen, J.-Y., Cody, N. A., Dominguez, D., et al. (2019). Nature, in press.

TABLE 1

Mouse genes ID with new internal exons and their splice sites, coding status, length, gene expression, PSI values and homologue genes in rat with gene expression.

| Mouse gene ID | Locus of newexon | Splice site | Locs6 on of new exon | Exon length | Mouse brain gene expression | Mouse brain PSI | Rat gene ID | Rat brain gene expression |
|---|---|---|---|---|---|---|---|---|
| ENSMUSG00000038866 | 1:107913164:107913264:+ | GTAG | utr5 | 101 | 4.954 | 0.202 | ENSRNOG00000002882 | 3.617 |
| ENSMUSG00000009907 | 1:108682358:108682605:− | GTAG | noncoding | 248 | 14.898 | 0 | ENSRNOG00000002705 | 10.615 |
| ENSMUSG00000036312 | 1:111894273:111895400:+ | CCAG | unknown | 1128 | 2.543 | 0.475 | ENSRNOG00000032490 | 2.202 |
| ENSMUSG00000036962 | 1:121832851:121833349:− | GTAG | utr5 | 499 | 0.148 | 0.192 | ENSRNOG00000025479 | 0.025 |
| ENSMUSG00000036155 | 1:129169384:129169440:+ | GTAG | utr5 | 57 | 11.296 | 0 | ENSRNOG00000003614 | 9.339 |
| ENSMUSG00000036104 | 1:129820768:129820942:+ | GTAG | utr5 | 175 | 26.352 | 0 | ENSRNOG00000003953 | 27.994 |
| ENSMUSG00000036104 | 1:129824807:129824961:+ | GCAG | utr5 | 155 | 26.352 | 0 | ENSRNOG00000003953 | 27.995 |
| ENSMUSG00000056211 | 1:130102753:130102825:+ | GTAG | utr5 | 73 | 87.475 | 0.698 | ENSRNOG00000004099 | 24.898 |
| ENSMUSG00000026354 | 1:107913164:130173555:− | GTAG | utr3 | 103 | 0.961 | 1 | ENSRNOG00000003681 | nan |
| ENSMUSG00000016528 | 1:132959085:132959118:− | GTAG | coding | 34 | 6.601 | 0.487 | ENSRNOG00000004726 | 69.132 |
| ENSMUSG00000042207 | 1:136459827:136459921:+ | GTAG | utr5 | 95 | 12.979 | 0 | ENSRNOG00000004433 | 8.047 |
| ENSMUSG00000042207 | 1:136477911:136477963:+ | GTAG | utr5 | 53 | 12.979 | 0 | ENSRNOG00000004433 | 8.047 |
| ENSMUSG00000026418 | 1:137679812:137680007:+ | GTAG | noncoding | 196 | 1.066 | 1 | ENSRNOG00000009073 | 0 |
| ENSMUSG00000051985 | 1:137881581:137881643:− | GTAG | utr5 | 63 | 3.806 | 0.359 | ENSRNOG00000026087 | 0.175 |
| ENSMUSG00000051985 | 1:137894344:137894468:− | GTAG | utr5 | 125 | 3.806 | 0.641 | ENSRNOG00000026087 | 0.175 |
| ENSMUSG00000051985 | 1:137895165:137895265:− | GTAG | utr5 | 101 | 3.806 | 0.641 | ENSRNOG00000026087 | 0.175 |
| ENSMUSG00000026395 | 1:139974279:139974293:− | GTAG | coding | 15 | 0.516 | 0.089 | ENSRNOG00000000655 | 1.417 |
| ENSMUSG00000032649 | 1:154351448:154351505:+ | GTAG | unknown | 58 | 1.744 | 0.054 | ENSRNOG00000028207 | 2.726 |
| ENSMUSG00000032649 | 1:154351627:154351720:+ | GTAG | unknown | 94 | 1.744 | 0.187 | ENSRNOG00000028207 | 2.726 |
| ENSMUSG00000026469 | 1:157187423:157187527:− | GTAG | utr5 | 105 | 20.509 | 0 | ENSRNOG00000000042 | 8.833 |
| ENSMUSG00000026601 | 1:158341119:158341174:− | GTAG | noncoding | 56 | 0 | 0 | ENSRNOG00000024694 | 0.016 |
| ENSMUSG00000033557 | 1:158630301:158630471:− | GTAG | coding | 171 | 20.611 | 0 | ENSRNOG00000004337 | 14.746 |
| ENSMUSG00000040297 | 1:163749223:163749294:− | GTAG | coding | 72 | 8.703 | 0 | ENSRNOG00000026542 | 7.4 |
| ENSMUSG00000025920 | 1:16417627:16417738:− | GTAG | utr5 | 112 | 36.849 | 0 | ENSRNOG00000042458 | 20.79 |
| ENSMUSG00000025920 | 1:16502011:16502092:− | GTAG | utr5 | 82 | 36.849 | 0 | ENSRNOG00000042458 | 20.79 |
| ENSMUSG00000040848 | 1:167112997:167113184:− | GTAG | utr5 | 188 | 3.711 | 0 | ENSRNOG00000003038 | 0.804 |
| ENSMUSG00000026571 | 1:167263783:167263912:− | GTAG | utr3 | 130 | 24.285 | 0 | ENSRNOG00000003078 | 31.081 |
| ENSMUSG00000040723 | 1:167584814:167584926:− | GTAG | coding | 113 | 0.867 | 0 | ENSRNOG00000003283 | 11.505 |

Column A and H show the homologues ID for mouse and rat for genes with mouse-specific new exons, column B shows the locus of the new exon in mouse while column D has the position of the new exon in the gene. Columns F and I show the average gene expression levels in brain for 3 individuals in mouse or rat, respectively. Column G shows the average PSI values in the mouse brain for 3 individuals.

TABLE 2

ID of mouse and rat genes with the number of TSSs used in both species and the number of mouse-specific new exons.

| Mouse gene ID | # TSSs in mouse | # mouse-specific new exons | Rat gene ID | # TSSs in rat |
|---|---|---|---|---|
| ENSMUSG00000000001 | 5 | 0 | ENSRNOG00000019465 | 5 |
| ENSMUSG00000000037 | 6 | 0 | ENSRNOG00000003726 | 2 |
| ENSMUSG00000000049 | 2 | 0 | ENSRNOG00000003566 | 1 |

TABLE 2-continued

ID of mouse and rat genes with the number of TSSs used in both species
and the number of mouse-specific new exons.

| Mouse gene ID | # TSSs in mouse | # mouse-specific new exons | Rat gene ID | # TSSs in rat |
|---|---|---|---|---|
| ENSMUSG00000000056 | 4 | 0 | ENSRNOG00000036664 | 2 |
| ENSMUSG00000000078 | 1 | 0 | ENSRNOG00000016885 | 3 |
| ENSMUSG00000000085 | 15 | 0 | ENSRNOG00000032183 | 6 |
| ENSMUSG00000000088 | 3 | 0 | ENSRNOG00000018816 | 2 |
| ENSMUSG00000000093 | 1 | 0 | ENSRNOG00000003517 | 1 |
| ENSMUSG00000000094 | 4 | 0 | ENSRNOG00000003544 | 5 |
| ENSMUSG00000000120 | 4 | 0 | ENSRNOG00000005392 | 2 |
| ENSMUSG00000000125 | 2 | 0 | ENSRNOG00000003845 | 2 |
| ENSMUSG00000000126 | 1 | 0 | ENSRNOG00000003066 | 2 |
| ENSMUSG00000000131 | 6 | 0 | ENSRNOG00000016722 | 7 |
| ENSMUSG00000000134 | 2 | 0 | ENSRNOG00000009605 | 1 |
| ENSMUSG00000000142 | 9 | 0 | ENSRNOG00000003612 | 8 |
| ENSMUSG00000000148 | 2 | 0 | ENSRNOG00000001236 | 4 |
| ENSMUSG00000000149 | 2 | 0 | ENSRNOG00000001235 | 3 |
| ENSMUSG00000000154 | 8 | 2 | ENSRNOG00000020562 | 3 |
| ENSMUSG00000000159 | 3 | 0 | ENSRNOG00000028216 | 5 |
| ENSMUSG00000000167 | 1 | 0 | ENSRNOG00000009965 | 2 |
| ENSMUSG00000000168 | 5 | 0 | ENSRNOG00000009994 | 1 |
| ENSMUSG00000000171 | 3 | 0 | ENSRNOG00000022980 | 2 |
| ENSMUSG00000000184 | 1 | 0 | ENSRNOG00000019939 | 2 |
| ENSMUSG00000000194 | 5 | 0 | ENSRNOG00000023589 | 1 |
| ENSMUSG00000000202 | 1 | 0 | ENSRNOG00000003109 | 1 |
| ENSMUSG00000000214 | 3 | 0 | ENSRNOG00000020410 | 5 |
| ENSMUSG00000000216 | 1 | 0 | ENSRNOG00000017842 | 1 |
| ENSMUSG00000000223 | 2 | 0 | ENSRNOG00000026704 | 1 |

Column B and E show the number of TSSs used in mouse and rat respectively in a specific gene pooling all nine sequenced tissues together.

TABLE 3

Numbers of SE, TSS, SE-TSS pairs, and genes expressed across tissues.

| | mouse SE, TSS | SE ψ > median | TSS ψ < median | TSS located upstream | TSS <2 kb upstream |
|---|---|---|---|---|---|
| no. of SE | 49488 | 24744 | 13237 | 9621 | 3333 |
| no. of TSS | 58095 | 37266 | 18633 | 9510 | 2991 |
| no. of SE-TSS pairs | 223568 | 103801 | 42528 | 21326 | 4284 |
| no. of genes | 13491 | 9363 | 4973 | 3833 | 1777 |

Column A shows the number of SE expressed in the nine tissues sequenced in mouse and the number of genes in which they are distributed. Column B shows the number of these SE in which the average of PSI values across tissues is above the median of all SE and column C the TSS paired with those SE with an average PSI across tissues below the median. Columns D and E reflect the subset of SE-TSS pairs and genes from previous columns in which the TSS is located upstream or proximal and upstream of the SE.

---

What is claimed is:

1. A method comprising inhibiting or activating transcription in a gene of a cell by:
   identifying a gene having an exon-mediated activation of transcription starts (EMATS) structure, wherein the EMATS structure comprises a weak transcription start site within 5 kb upstream of a highly included alternative internal exon, wherein the weak transcription start site has an average activity that is less than a median activity of a human transcription start site, and wherein the highly included internal exon comprises an exon flanked by introns whose average inclusion level, measured as percent spliced in (PSI), is greater than a median PSI of alternative internal exons;
   selecting an antisense oligonucleotide or small molecule that is targeted to the highly included alternative internal exon; and
   contacting the cell with the antisense oligonucleotide or small molecule to inhibit transcription from the weak transcription start site or to activate transcription from the weak transcription start site.

2. The method of claim 1, wherein the antisense oligonucleotide (ASO) is a morpholino oligonucleotide, a phosphorothioate ASO, a 2'-O-methyl (2'-OMe) ASO, 2'-O-methoxyethyl (2'MOE) ASO, a locked nucleic acid (LNA) ASO, a peptide-conjugated phosphorodiamidate morpholino (PMO) ASO or a Vivo-linked phosphorodiamidate morpholino (VPMO).

3. The method of claim 1, wherein the antisense oligonucleotide or small molecule is targeted for the 3' splice site or 5' splice site of the internal exon.

4. The method of claim 1, wherein transcription from the weak transcription start site is inhibited and the gene is HTT, NOTCH2 gene, MEN1 gene, dystrophin gene or p53 gene.

5. The method of claim 1, wherein the gene is associated with myotonic dystrophy type I or with Huntington's disease.

6. The method of claim 1, wherein the gene is an oncogene or an antioncogene.

7. The method of claim 6, wherein the oncogene is c-myc, Ras, STAT3, or bcl-2.

8. The method of claim 1, wherein the antisense oligonucleotide- or small molecule is targeted to an intronic silencing element.

9. The method of claim 1, wherein the gene encodes a therapeutic protein.

10. The method of claim 9, wherein the therapeutic protein is p53, pRb, PTEN, pVHL, APC, BRCA1, BRCA2, CD95, ST5, YPEL3, ST7, or ST14.

11. The method of claim 1, wherein the antisense oligonucleotide is a splice switching oligonucleotide.

12. The method of claim 1, wherein transcription from the weak transcription start site/promoter is activated and the gene is MLH3 gene, dystrophin gene or utrophin gene.

13. The method of claim 1, wherein the antisense oligonucleotide- or small molecule is targeted to a silencing element that is downstream or upstream of a skipped exon.

14. The method of claim 1, wherein the antisense oligonucleotide- or small molecule is targeted to an exonic silencing element on a skipped exon.

* * * * *